United States Patent [19]
Wilson et al.

[11] Patent Number: 6,001,557
[45] Date of Patent: Dec. 14, 1999

[54] ADENOVIRUS AND METHODS OF USE THEREOF

[75] Inventors: James M. Wilson, Gladwyne, Pa.; Krishna J. Fisher, New Orleans, La.; Shu-Jen Chen, Aldan, Pa.; Matthew Weitzman, La Jolla, Calif.

[73] Assignee: The Trustees of the University of Pennsylvania, Philadelphia, Pa.

[21] Appl. No.: 08/836,022

[22] PCT Filed: Oct. 27, 1995

[86] PCT No.: PCT/US95/14017

§ 371 Date: Aug. 25, 1997

§ 102(e) Date: Aug. 25, 1997

[87] PCT Pub. No.: WO96/13597

PCT Pub. Date: May 9, 1996

Related U.S. Application Data

[63] Continuation-in-part of application No. 08/331,381, Oct. 28, 1994.

[51] Int. Cl.$^6$ .............................. C12Q 1/70; C12N 15/86; C12N 15/64

[52] U.S. Cl. ................................. 435/5; 435/6; 435/91.4; 435/320.1; 435/325; 435/239; 435/366; 435/367; 435/368; 435/369; 530/300

[58] Field of Search .................................... 435/5, 6, 325, 435/366, 320.1, 367, 368, 369, 239, 91.4; 424/93.2, 93.6; 530/300

[56] References Cited

U.S. PATENT DOCUMENTS

| | | | |
|---|---|---|---|
| 5,166,320 | 11/1992 | Wu et al. | 530/395 |
| 5,240,846 | 8/1993 | Collins et al. | 435/371 |
| 5,252,479 | 10/1993 | Srivastava | 435/235.1 |
| 5,543,328 | 8/1996 | McClelland | 435/320.1 |
| 5,652,224 | 7/1997 | Wilson et al. | 514/44 |

FOREIGN PATENT DOCUMENTS

| | | |
|---|---|---|
| WO91/18088 | 11/1991 | WIPO. |
| WO93/03769 | 3/1993 | WIPO. |
| WO93/19191 | 9/1993 | WIPO. |
| WO94/08026 | 4/1994 | WIPO. |
| WO94/12649 | 6/1994 | WIPO. |
| WO94/17832 | 8/1994 | WIPO. |
| WO94/28152 | 12/1994 | WIPO. |
| WO94/28938 | 12/1994 | WIPO. |
| WO95/00655 | 1/1995 | WIPO. |
| WO95/02697 | 1/1995 | WIPO. |
| WO95/27071 | 10/1995 | WIPO. |
| WO95/29993 | 11/1995 | WIPO. |
| WO95/34671 | 12/1995 | WIPO. |
| WO96/13596 | 5/1996 | WIPO. |
| WO96/14061 | 5/1996 | WIPO. |
| WO96/18418 | 6/1996 | WIPO. |

OTHER PUBLICATIONS

Y. Watanabe, "Serial Inbreeding of Rabbits with Hereditary Hyperlipidemia (WHHL–Rabbit)", *Atherosclerosis*, 36:261–268 (1980).

K. Tanzawa et al., "WHHL–Rabbit: A Low Density Lipoprotein Receptor–Deficient Animal Model for Familial Hypercholesterolemia", *FEBS Letters*, 118(1):81–84 (Aug., 1980).

J. Goldstein et al, "Defective Lipoprotein Receptors and Atherosclerosis—Lessons form an Animal Counterpart of Familial Hypercholesterolemia", *New Eng. J. Med.*, 309(5):288–296 (Aug. 4, 1983).

S. Ishibashi et al, "Hypercholesterolemia in Low Density Lipoprotein Receptor Knockout Mice and its Reversal by Adenovirus –mediated Gene Delivery", *J. Clin. Invest.*, 92:883–893 (Aug., 1993) [Ishibashi I].

S. Ishibashi et al, "massive Xathomatosis and Atherosclerosis in Cholesterol–fed Low Density Lipoprotein Receptor–negative Mice", *J. Clin. Invest.*, 93:1885–1893 (May, 1994) [Ishibashi II].

J. Wilson, "Cystic Fibrosis—Vehicles for Gene Therapy", *Nature*, 365:691–692 (Oct. 21, 1993) [Wilson I].

M. Horwitz, "Adenoviridae and Their Replication", *Virology*, 2d edition, ed. B. N. Fields, Raven Press, Ltd., New York, Chapter 60, pp. 1679–1721 (1990).

Y. Yang et al., "Cellular Immunity to Viral Antigens Limits E1–deleted Adenoviruses for Gene Therapy", *Proc. Natl. Acad. Sci. USA,* 91:4407–4411 (May, 1994).

J. Wilson et al, "Correction of the Genetic Defect in Hepatocytes for the Watanabe Heritable Hyperlipidemic Rabbit", *Proc. Natl. Acad. Sco. USA,* 85:4421–4425 (Jun., 1988) [Wilson II].

J. Wilson et al., "Research Article—Transplantation of Allogeneic Hepatocytes into LDL Receptor Deficient Rabbits Leads to Transient Improvement in Hypercholesterolemia", *Clin. Bio.,* 3:21–26 (Spring, 1991) [Wilson II].

M. Grossman et al., "Towards Liver–Directed Gene Therapy: Retrovirus–Mediated Gene Transfer into Human Hepatocytes", *Som. Cell. And Mol. Gen.,* 17(6):601–607 (Nov., 1991).

M. Boshart et al., "A Very Strong Enhancer is Located Upstream of an Immediate Early Gene of Human Cytomegalovirus", *Cell,* 41:521–530 (Jun., 1985).

C. Wu et al, "Targeting Genes: Delivery and Persistent Expression of a Foreign Gene Driven by Mammalian Regulatory Elements in Vivo", *J. Biol. Chem.,* 264(29):16985–16987 (Oct. 15, 1989).

(List continued on next page.)

*Primary Examiner*—David Guzo
*Attorney, Agent, or Firm*—Howson and Howson

[57] ABSTRACT

A recombinant adenovirus and a method for producing the virus are provided which utilize a recombinant shuttle vector comprising adenovirus DNA sequence for the 5' and 3' cis-elements necessary for replication and virion encapsidation in the absence of sequence encoding viral genes and a selected minigene linked thereto, and a helper adenovirus comprising sufficient adenovirus gene sequences necessary for a productive viral infection. Desirably, the helper gene is crippled by modifications to its 5' packaging sequences, which facilitates purification of the viral particle from the helper virus.

23 Claims, 45 Drawing Sheets

OTHER PUBLICATIONS

K. Fisher et al., "Biochemical and Functional Analysis of an Adenovirus–Based Ligand Complex for Gene Transfer", *Biochem. J.* 229:49–58 (Apr. 1, 1994).

K. Kozarsky et al., "In Vivo Correction of Low Density Lipoprotein Receptor Deficiency in the Watanabe Heritage Hyperlipidemic Rabbit with Recombinant Adenoviruses", *J. Biol. Chem.*, 269(18):13695–13702 (May 6, 1994).

C. Laughlin et al., "Cloning of Infectious Adeno–associated Virus Genomes in Bacterial Plasmids", *Gene,* 23:65–73 (Jul., 1983).

J. Price et al., "Lineage Analysis in the Vertebrate Nervous System by Retrovirus–mediated Gene Transfer", *Proc. Natl. Acad. Sci. USA,* 84156–160 (Jan., 1987).

J. Wilson et al., "A Novel Mechanism for Achieving Transgene Persistence in Vivo after Somatic Gene Transfer into Hepatocytes", *J. Biol. Chem.*, 267(16):11483–11489 (Jun. 5, 1992) [Wilson IV].

T. Kost et al, "The Nucleotide Sequence of the Chick Cytoplasmic β–actin Gene", *Nucl. Acids Res.*, 11(23):8287–8301 (Dec. 11, 1983).

J. Schreiber et al, "Recombinant Retroviruses Containing Novel Reporter Genes", *BioTechniques,* 14(5):818–823 (May, 1993).

J. Riordan et al, "Identification of the Cystic Fibrosis Gene: Cloning and Characterization of Complementary DNA", *Science,* 245:1066–1073 (Sep. 8, 1989).

M. Brown et al, "A Receptor–Mediated Pathway for Cholesterol Homeostatis", *Science,* 232:34–46 (Apr. 4, 1986).

T. Yamamoto et al, "The Human LDL Receptor: A Cysteine–Rich Protein with Multiple Alu Sequences in its mRNA", *Cell,* 39:27–38 (Nov., 1984).

R. Samulski et al, "Helper–Free Stocks of Recombinant Adeno–Associated Viruses: Normal Integration does not Require Viral Gene Expression", *J. Virol.,* 63(9):3822–3828 (Sep., 1989).

T. Shenk et al, "Genetic Analysis of Adenoviruses", *Current Topics in Microbiol. and Immunol.,* 111:1–39 (1984).

P. Hearing et al, "Identification of a Repeated Sequence Element Required for Efficient Encapsidation of the Adenovirus Type 5 Chromosome", *J. Virol.,* 61(8):2555–2558 (Aug., 1987).

M. Grable et al, "Adenovirus Type 5 Packaging Domain is Composed of a Repeated Element that is Functionally Redundant", *J. Virol.,* 64(5):2047–2056 (May, 1990) [Grable I].

M. Grable et al, "cis and trans Requirements for the Selective Packaging of Adenovirus Type 5 DNA", *J. Virol.,* 66(2):723–731 (Feb., 1992) [Grable II].

B. Davidson et al, "A Model System for in vivo Gene Transfer into the Central Nervous System Using an Adenoviral Vector", *Nature Genetics,* 3:219–223 (Mar., 1993).

J. Engelhardt et al, "Adenovirus–Mediated Transfer of the CFTR Gene to Lung of Nonhuman Primates: Biological Efficacy Study", *Human Genet. Ther.,* 4:759–769 (Dec., 1993) [Engelhardt I].

J. Engelhardt et al, "Prolonged Transgene Expression in Cotton Rat Lung with Recombinant Adenoviruses Defective in E2a", *Human Gene Ther.,*5:1217–1229 (Oct., 1994) [Engelhardt II].

K. Kozarsky et al, "Adenovirus–Mediated Correction of the Genetic Defect in Hepatocytes from Patients with Familial Hypercholesterolemia", *Somatic Cell and Molecular Genetics,* 19(5):449–458 (Sep., 1993) [Kozarsky II].

K. Kozarsky et al, "Gene Therapy: Adenovirus Vectors", *Curr. Opin. Genet. Devel.,* 3:499–503 (Mar., 1993) [Kozarsky III].

B. Roessler et al, "Adenoviral–mediated Gene Transfer to Rabbit Synovium In Vivo", *J. Clin. Invest.,* 92:1085–1092 (Aug., 1993).

M. Rosenfeld et al, "In Vivo Transfer of the Human Cystic Fibrosis Transmembrane Conductance Regulator Gene to the Airway Epithelium", *Cell,* 68:143–155 (Jan. 10, 1992).

W. R. Smythe et al, "Successful Adenovirus–Mediated Gene Transfer in an In Vivo Model of Human Malignant Mesothelioma", *Ann. Thorac. Surg.,* 57(6):1395–1401 (Jun., 1994).

Y. Yang et al, "MHC Class I–Restricted Cytotoxic T Lymphocytes to Viral Antigens Destroy Hepatocytes in Mice Infected with E1–Deleted Recombinant Adenoviruses", *Immunity,* 1:433–442 (Aug., 1994) [Yang II].

Y. Yang et al, "Inactivation of E2a in Recombinant Adenoviruses Improves the Prospect for Gene Therapy in Cystic Fibrosis", *Nature Genetics,* 7:362–369 (Jul., 1994) [Yang III].

B. Quantin et al, "Adenovirus as an Expression Vector in Muscle Cells In Vivo", *Proc. Natl. Acad. Sci. USA,* 89:2581–2584 (Apr., 1992).

T. Smith et al, "Adenovirus Mediated Expression of Therapeutic Plasma Levels of Human Factor IX in Mice", *Nature Genetics,* 5:397–402 (Dec., 1993).

K. Berkner, "Expression of Heterologous Sequences in Adenoviral Vectors", *Current Topics in Microbiology and Immunology,* 158:39–66 (1992) [Berkner I].

K. Berkner, "Development of Adenovirus Vectors for the Expression of Heterologous Genes", *BioTechniques,* 6(7):616–629 (1988) [Berkner II].

S. Goodman et al, "Recombinant Adeno–Associated Virus––Mediated Gene Transfer into Hematopoietic Progenitor Cells", *Blood,* 84(5):1492–1500 Sep. 1, 1994).

K.J. Fisher et al, "Recombinant Adenovirus deleted of all viral genes for gene therapy of cystic fibrosis", *Virology,* 217(1):11–22 (Mar. 1996).

U.S. Patent Application No. 08/331,384, filed Oct. 28, 1994.

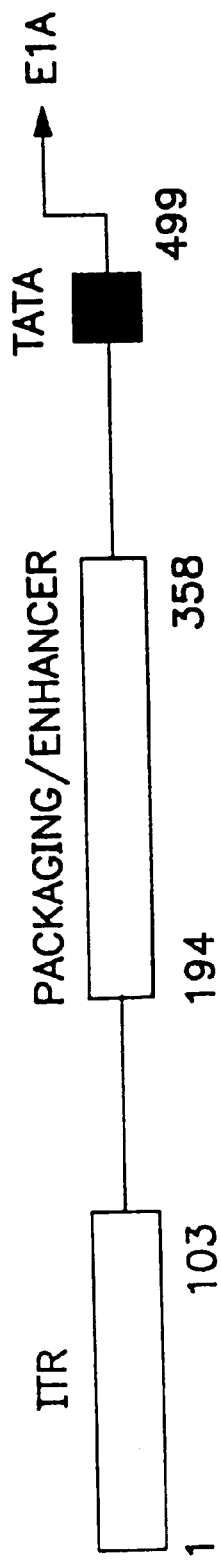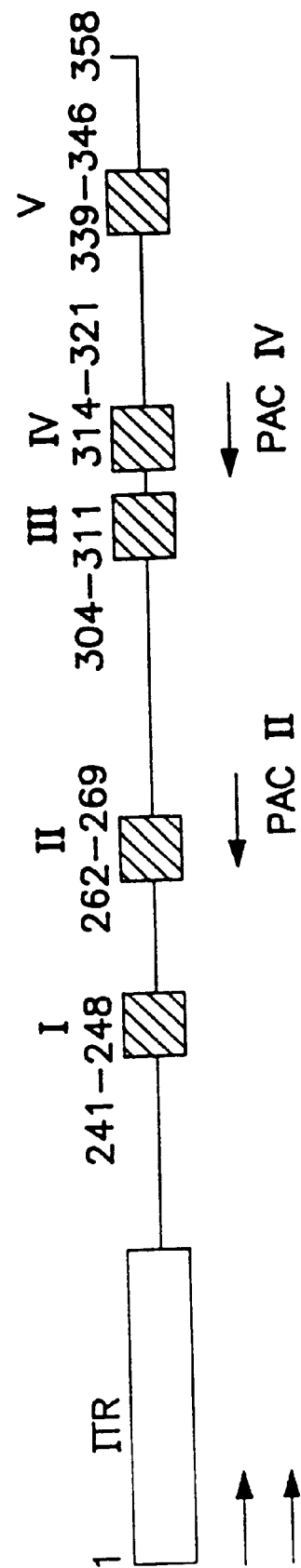
FIG. 1A
FIG. 1B

FIGURE 3A

```
GAACTCGAGC AGCTGAAGCT TGAATTCCAT CATCAATAAT ATACCTTATT    50
TTGGATTGAA GCCAATATGA TAATGAGGGG GTGGAGTTTG TGACGTGGCG   100
CGGGGCGTGG GAACGGGGCG GGTGACGTAG GTTTTAGGGC GGAGTAACTT   150
GTATGTGTTG GGAATTGTAG TTTTCTTAAA ATGGGAAGTT ACGTAACGTG   200
GGAAAACGGA AGTGACGATT TGAGGAAGTT GTGGGTTTTT TGGCTTTCGT   250
TTCTGGGCGT AGGTTCGCGT GCGGTTTTCT GGGTGTTTTT TGTGGACTTT   300
AACCGTTACG TCATTTTTTA GTCCTATATA TACTCGCTCT GCACTTGGCC   350
CTTTTTTACA CTGTGACTGA TTGAGCTGGT GCCGTGTCGA GTGGTGTTTT   400
TTTAATAGGT TTTCTTTTTT ACTGGTAAGG CTGACTGTTA GGCTGCCGCT   450
GTGAAGCGCT GTATGTTGTT CTGGAGCGGG AGGGTGCTAT TTTGCCTAGG   500
CAGGAGGGTT TTTCAGGTGT TTATGTGTTT TTCTCTCCTA TTAATTTTGT   550
TATACCTCCT ATGGGGCTG TAATGTTGTC TCTACGCCTG CGGGTATGTA   600
TTCCCCCCAA GCTTGCATGC CTGCAGGTCG ACTCTAGAGG ATCCGAAAAA   650
ACCTCCCACA CCTCCCCCTG AACCTGAAAC ATAAAATGAA TGCAATTGTT   700
GTTGTTAACT TGTTTATTGC AGCTTATAAT GGTTACAAAT AAAGCAATAG   750
CATCACAAAT TTCACAAATA AAGCATTTTT TCACTGCAT TCTAGTTGTG   800
GTTTGTCCAA ACTCATCAAT GTATCTTATC ATGTCTGGAT CCCCGCGGCC   850
GCCTAGAGTC GAGGCCGAGT TTGTCAGAAA GCAGACCAAA CAGCGGTTGG   900
AATAATAGCG AGAACAGAGA AATAGCGGCA AAAATAATAC CCGTATCACT   950
TTTGCTGATA TGGTTGATGT CATGTAGCCA AATCGGGAAA AACGGGAAGT  1000
AGGCTCCCAT GATAAAAAAG TAAAAGAAAA AGAATAAACC GAACATCCAA  1050
AAGTTTGTGT TTTTTAAATA GTACATAATG GATTTCCTTA CGCGAAATAC  1100
GGGCAGACAT GGCCTGCCCG GTTATTATTA TTTTTGACAC CAGACCAACT  1150
GGTAATGGTA GCGACCGGCG CTCAGCTGTA ATTCCGCCGA TACTGACGGG  1200
CTCCAGGAGT CGTCGCCACC AATCCCCATA TGGAAACCGT CGATATTCAG  1250
CCATGTGCCT TCTTCCGCGT GCAGCAGATG GCGATGGCTG CTTTCCATCA  1300
GTTGCTGTTG ACTGTAGCGG CTGATGTTGA ACTGGAAGTC GCCGCGCCAC  1350
```

FIGURE 3B

```
TGGTGTGGGC CATAATTCAA TTCGCGCGTC CCGCAGCGCA GACCGTTTTC    1400
GCTCGGGAAG ACGTACGGGG TATACATGTC TGACAATGGC AGATCCCAGC    1450
GGTCAAAACA GGCGGCAGTA AGGCGGTCGG GATAGTTTTC TTGCGGCCCT    1500
AATCCGAGCC AGTTTACCCG CTCTGCTACC TGCGCCAGCT GGCAGTTCAG    1550
GCCAATCCGC GCCGGATGCG GTGTATCGCT CGCCACTTCA ACATCAACGG    1600
TAATCGCCAT TTGACCACTA CCATCAATCC GGTAGGTTTT CCGGCTGATA    1650
AATAAGGTTT TCCCCTGATG CTGCCACGCG TGAGCGGTCG TAATCAGCAC    1700
CGCATCAGCA AGTGTATCTG CCGTGCACTG CAACAACGCT GCTTCGGCCT    1750
GGTAATGGCC CGCCGCCTTC CAGCGTTCGA CCCAGGCGTT AGGGTCAATG    1800
CGGGTCGCTT CACTTACGCC AATGTCGTTA TCCAGCGGTG CACGGGTGAA    1850
CTGATCGCGC AGCGGCGTCA GCAGTTGTTT TTTATCGCCA ATCCACATCT    1900
GTGAAAGAAA GCCTGACTGG CGGTTAAATT GCCAACGCTT ATTACCCAGC    1950
TCGATGCAAA AATCCATTTC GCTGGTGGTC AGATGCGGGA TGGCGTGGGA    2000
CGCGGCGGGG AGCGTCACAC TGAGGTTTTC CGCCAGACGC CACTGCTGCC    2050
AGGCGCTGAT GTGCCCGGCT TCTGACCATG CGGTCGCGTT CGGTTGCACT    2100
ACGCGTACTG TGAGCCAGAG TTGCCCGGCG CTCTCCGGCT GCGGTAGTTC    2150
AGGCAGTTCA ATCAACTGTT TACCTTGTGG AGCGACATCC AGAGGCACTT    2200
CACCGCTTGC CAGCGGCTTA CCATCCAGCG CCACCATCCA GTGCAGGAGC    2250
TCGTTATCGC TATGACGGAA CAGGTATTCG CTGGTCACTT CGATGGTTTG    2300
CCCGGATAAA CGGAACTGGA AAAACTGCTG CTGGTGTTTT GCTTCCGTCA    2350
GCGCTGGATG CGGCGTGCGG TCGGCAAAGA CCAGACCGTT CATACAGAAC    2400
TGGCGATCGT TCGGCGTATC GCCAAAATCA CCGCCGTAAG CCGACCACGG    2450
GTTGCCGTTT TCATCATATT TAATCAGCGA CTGATCCACC CAGTCCCAGA    2500
CGAAGCCGCC CTGTAAACGG GGATACTGAC GAAACGCCTG CCAGTATTTA    2550
GCGAAACCGC CAAGACTGTT ACCCATCGCG TGGGCGTATT CGCAAAGGAT    2600
CAGCGGGCGC GTCTCTCCAG GTAGCGAAAG CCATTTTTTG ATGGACCATT    2650
```

FIGURE 3C

```
TCGGCACAGC CGGGAAGGGC TGGTCTTCAT CCACGCGCGC GTACATCGGG    2700
CAAATAATAT CGGTGGCCGT GGTGTCGGCT CCGCCGCCTT CATACTGCAC    2750
CGGGCGGGAA GGATCGACAG ATTTGATCCA GCGATACAGC GCGTCGTGAT    2800
TAGCGCCGTG GCCTGATTCA TTCCCCAGCG ACCAGATGAT CACACTCGGG    2850
TGATTACGAT CGCGCTGCAC CATTCGCGTT ACGCGTTCGC TCATCGCCGG    2900
TAGCCAGCGC GGATCATCGG TCAGACGATT CATTGGCACC ATGCCGTGGG    2950
TTTCAATATT GGCTTCATCC ACCACATACA GGCCGTAGCG GTCGCACAGC    3000
GTGTACCACA GCGGATGGTT CGGATAATGC GAACAGCGCA CGGCGTTAAA    3050
GTTGTTCTGC TTCATCAGCA GGATATCCTG CACCATCGTC TGCTCATCCA    3100
TGACCTGACC ATGCAGAGGA TGATGCTCGT GACGGTTAAC GCCTCGAATC    3150
AGCAACGGCT TGCCGTTCAG CAGCAGCAGA CCATTTTCAA TCCGCACCTC    3200
GCGGAAACCG ACATCGCAGG CTTCTGCTTC AATCAGCGTG CCGTCGGCGG    3250
TGTGCAGTTC AACCACCGCA CGATAGAGAT TCGGGATTTC GGCGCTCCAC    3300
AGTTTCGGGT TTTCGACGTT CAGACGTAGT GTGACGCGAT CGGCATAACC    3350
ACCACGCTCA TCGATAATTT CACCGCCGAA AGGCGCGGTG CCGCTGGCGA    3400
CCTGCGTTTC ACCCTGCCAT AAAGAAACTG TTACCCGTAG GTAGTCACGC    3450
AACTCGCCGC ACATCTGAAC TTCAGCCTCC AGTACAGCGC GGCTGAAATC    3500
ATCATTAAAG CGAGTGGCAA CATGGAAATC GCTGATTTGT GTAGTCGGTT    3550
TATGCAGCAA CGAGACGTCA CGGAAAATGC CGCTCATCCG CCACATATCC    3600
TGATCTTCCA GATAACTGCC GTCACTCCAA CGCAGCACCA TCACCGCGAG    3650
GCGGTTTTCT CCGGCGCGTA AAAATGCGCT CAGGTCAAAT TCAGACGGCA    3700
AACGACTGTC CTGGCCGTAA CCGACCCAGC GCCCGTTGCA CCACAGATGA    3750
AACGCCGAGT TAACGCCATC AAAAATAATT CGCGTCTGGC CTTCCTGTAG    3800
CCAGCTTTCA TCAACATTAA ATGTGAGCGA GTAACAACCC GTCGGATTCT    3850
CCGTGGGAAC AAACGGCGGA TTGACCGTAA TGGGATAGGT TACGTTGGTG    3900
TAGATGGGCG CATCGTAACC GTGCATCTGC CAGTTTGAGG GGACGACGAC    3950
```

FIGURE 3D

```
AGTATCGGCC TCAGGAAGAT CGCACTCCAG CCAGCTTTCC GGCACCGCTT    4000
CTGGTGCCGG AAACCAGGCA AAGCGCCATT CGCCATTCAG GCTGCGCAAC    4050
TGTTGGGAAG GGCGATCGGT GCGGGCCTCT TCGCTATTAC GCCAGCTGGC    4100
CAAAGGGGA  TGTGCTGCAA GGCGATTAAG TTGGGTAACG CCAGGGTTTT    4150
CCCAGTCACG ACGTTGTAAA ACGACGGGAT CGCGCTTGAG CAGCTCCTTG    4200
CTGGTGTCCA GACCAATGCC TCCCAGACCG GCAACGAAAA TCACGTTCTT    4250
GTTGGTCAAA GTAAACGACA TGGTGACTTC TTTTTTGCTT TAGCAGGCTC    4300
TTTCGATCCC CGGGAATTGC GGCCGCGGGT ACAATTCCGC AGCTTTTAGA    4350
GCAGAAGTAA CACTTCCGTA CAGGCCTAGA AGTAAAGGCA ACATCCACTG    4400
AGGAGCAGTT CTTTGATTTG CACCACCACC GGATCCGGGA CCTGAAATAA    4450
AAGACAAAAA GACTAAACTT ACCAGTTAAC TTTCTGGTTT TTCAGTTCCT    4500
CGAGTACCGG ATCCTCTAGA GTCCGGAGGC TGGATCGGTC CCGGTCTCTT    4550
CTATGGAGGT CAAAACAGCG TGGATGGCGT CTCCAGGCGA TCTGACGGTT    4600
CACTAAACGA GCTCTGCTTA TATAGACCTC CCACCGTACA CGCCTACCGC    4650
CCATTTGCGT CAATGGGGCG GAGTTGTTAC GACATTTGG  AAAGTCCCGT    4700
TGATTTTGGT GCCAAAACAA ACTCCCATTG ACGTCAATGG GGTGGAGACT    4750
TGGAAATCCC CGTGAGTCAA ACCGCTATCC ACGCCCATTG ATGTACTGCC    4800
AAAACCGCAT CACCATGGTA ATAGCGATGA CTAATACGTA GATGTACTGC    4850
CAAGTAGGAA AGTCCCATAA GGTCATGTAC TGGGCATAAT GCCAGGCGGG    4900
CCATTTACCG TCATTGACGT CAATAGGGGG CGTACTTGGC ATATGATACA    4950
CTTGATGTAC TGCCAAGTGG GCAGTTTACC GTAAATACTC CACCCATTGA    5000
CGTCAATGGA AAGTCCCTAT TGGCGTTACT ATGGGAACAT ACGTCATTAT    5050
TGACGTCAAT GGGCGGGGGT CGTTGGGCGG TCAGCCAGGC GGGCCATTTA    5100
CCGTAAGTTA TGTAACGACC TGCAGGTCGA CTCTAGAGGA TCTCCCTAGA    5150
CAAATATTAC GCGCTATGAG TAACACAAAA TTATTCAGAT TCACTTCCT    5200
CTTATTCAGT TTTCCCGCGA AAATGGCCAA ATCTTACTCG GTTACGCCCA    5250
```

FIGURE 3E

```
AATTTACTAC AACATCCGCC TAAAACCGCG CGAAAATTGT CACTTCCTGT    5300
GTACACCGGC GCACACCAAA AACGTCACTT TTGCCACATC CGTCGCTTAC    5350
ATGTGTTCCG CCACACTTGC AACATCACAC TTCCGCCACA CTACTACGTC    5400
ACCCGCCCCG TTCCCACGCC CCGCGCCACG TCACAAACTC CACCCCCTCA    5450
TTATCATATT GGCTTCAATC CAAAATAAGG TATATTATTG ATGATGCTAG    5500
CGAATTCATC GATGATATCA GATCTGCCGG TCTCCCTATA GTGAGTCGTA    5550
TTAATTTCGA TAAGCCAGGT TAACCTGCAT TAATGAATCG GCCAACGCGC    5600
GGGGAGAGGC GGTTTGCGTA TTGGGCGCTC TTCCGCTTCC TCGCTCACTG    5650
ACTCGCTGCG CTCGGTCGTT CGGCTGCGGC GAGCGGTATC AGCTCACTCA    5700
AAGGCGGTAA TACGGTTATC CACAGAATCA GGGGATAACG CAGGAAAGAA    5750
CATGTGAGCA AAAGGCCAGC AAAAGGCCAG GAACCGTAAA AAGGCCGCGT    5800
TGCTGGCGTT TTTCCATAGG CTCCGCCCCC CTGACGAGCA TCACAAAAAT    5850
CGACGCTCAA GTCAGAGGTG GCGAAACCCG ACAGGACTAT AAAGATACCA    5900
GGCGTTTCCC CCTGGAAGCT CCCTCGTGCG CTCTCCTGTT CCGACCCTGC    5950
CGCTTACCGG ATACCTGTCC GCCTTTCTCC CTTCGGGAAG CGTGGCGCTT    6000
TCTCAATGCT CACGCTGTAG GTATCTCAGT TCGGTGTAGG TCGTTCGCTC    6050
CAAGCTGGGC TGTGTGCACG AACCCCCCGT TCAGCCCGAC CGCTGCGCCT    6100
TATCCGGTAA CTATCGTCTT GAGTCCAACC CGGTAAGACA CGACTTATCG    6150
CCACTGGCAG CAGCCACTGG TAACAGGATT AGCAGAGCGA GGTATGTAGG    6200
CGGTGCTACA GAGTTCTTGA AGTGGTGGCC TAACTACGGC TACACTAGAA    6250
GGACAGTATT TGGTATCTGC GCTCTGCTGA AGCCAGTTAC CTTCGGAAAA    6300
AGAGTTGGTA GCTCTTGATC CGGCAAACAA ACCACCGCTG CTAGCGGTGG    6350
TTTTTTTGTT TGCAAGCAGC AGATTACGCG CAGAAAAAAA GGATCTCAAG    6400
AAGATCCTTT GATCTTTTCT ACGGGTCTG ACGCTCAGTG GAACGAAAAC    6450
TCACGTTAAG GGATTTTGGT CATGAGATTA TCAAAAAGGA TCTTCACCTA    6500
GATCCTTTTA AATTAAAAAT GAAGTTTTAA ATCAATCTAA AGTATATATG    6550
```

FIGURE 3F

```
AGTAAACTTG GTCTGACAGT TACCAATGCT TAATCAGTGA GGCACCTATC    6600
TCAGCGATCT GTCTATTTCG TTCATCCATA GTTGCCTGAC TCCCCGTCGT    6650
GTAGATAACT ACGATACGGG AGGGCTTACC ATCTGGCCCC AGTGCTGCAA    6700
TGATACCGCG AGACCCACGC TCACCGGCTC CAGATTTATC AGCAATAAAC    6750
CAGCCAGCCG GAAGGGCCGA GCGCAGAAGT GGTCCTGCAA CTTTATCCGC    6800
CTCCATCCAG TCTATTAATT GTTGCCGGGA AGCTAGAGTA AGTAGTTCGC    6850
CAGTTAATAG TTTGCGCAAC GTTGTTGCCA TTGCTACAGG CATCGTGGTG    6900
TCACGCTCGT CGTTTGGTAT GGCTTCATTC AGCTCCGGTT CCCAACGATC    6950
AAGGCGAGTT ACATGATCCC CCATGTTGTG CAAAAAAGCG GTTAGCTCCT    7000
TCGGTCCTCC GATCGTTGTC AGAAGTAAGT TGGCCGCAGT GTTATCACTC    7050
ATGGTTATGG CAGCACTGCA TAATTCTCTT ACTGTCATGC CATCCGTAAG    7100
ATGCTTTTCT GTGACTGGTG AGTACTCAAC CAAGTCATTC TGAGAATAGT    7150
GTATGCGGCG ACCGAGTTGC TCTTGCCCGG CGTCAATACG GGATAATACC    7200
GCGCCACATA GCAGAACTTT AAAAGTGCTC ATCATTGGAA AACGTTCTTC    7250
GGGGCGAAAA CTCTCAAGGA TCTTACCGCT GTTGAGATCC AGTTCGATGT    7300
AACCCACTCG TGCACCCAAC TGATCTTCAG CATCTTTTAC TTTCACCAGC    7350
GTTTCTGGGT GAGCAAAAAC AGGAAGGCAA AATGCCGCAA AAAAGGGAAT    7400
AAGGGCGACA CGGAAATGTT GAATACTCAT ACTCTTCCTT TTTCAATATT    7450
ATTGAAGCAT TTATCAGGGT TATTGTCTCA TGAGCGGATA CATATTTGAA    7500
TGTATTTAGA AAAATAAACA AATAGGGGTT CCGCGCACAT TTCCCCGAAA    7550
AGTGCCACCT GACGTCTAAG AAACCATTAT TATCATGACA TTAACCTATA    7600
AAAATAGGCG TATCACGAGG CCCTTTCGTC TCGCGCGTTT CGGTGATGAC    7650
GGTGAAAACC TCTGACACAT GCAGCTCCCG GAGACGGTCA CAGCTTGTCT    7700
GTAAGCGGAT GCCGGGAGCA GACAAGCCCG TCAGGCGCG  TCAGCGGGTG    7750
TTGGCGGGTG TCGGGCTGG  CTTAACTATG CGGCATCAGA GCAGATTGTA    7800
CTGAGAGTGC ACCATATGGA CATATTGTCG TTAGAACGCG GCTACAATTA    7850
ATACATAACC TTATGTATCA TACACATACG ATTTAGGTGA CACTATA      7897
```

FIGURE 5A

| | | | | | |
|---|---|---|---|---|---|
| GAATTCGCTA | GCTAGCGGGG | GAATACATAC | CCGCAGGCGT | AGAGACAACA | 50 |
| TTACAGCCCC | CATAGGAGGT | ATAACAAAAT | TAATAGGAGA | GAAAAACACA | 100 |
| TAAACACCTG | AAAAACCCTC | CTGCCTAGGC | AAAATAGCAC | CCTCCCGCTC | 150 |
| CAGAACAACA | TACAGCGCTT | CACAGCGGCA | GCCTAACAGT | CAGCCTTACC | 200 |
| AGTAAAAAAG | AAAACCTATT | AAAAAAACAC | CACTCGACAC | GGCACCAGCT | 250 |
| CAATCAGTCA | CAGTGTAAAA | AAGGGCCAAG | TGCAGAGCGA | GTATATATAG | 300 |
| GACTAAAAAA | TGACGTAACG | GTTAAAGTCC | ACAAAAAACA | CCCAGAAAAC | 350 |
| CGCACGCGAA | CCTACGCCCA | GAAACGAAAG | CCAAAAAACC | CACAACTTCC | 400 |
| TCAAATCGTC | ACTTCCGTTT | TCCCACGTTA | CGTAACTTCC | CATTTTAAGA | 450 |
| AAACTACAAT | TCCCAACACA | TACAAGTTAC | TCCGCCCTAA | AACCTACGTC | 500 |
| ACCCGCCCCG | TTCCCACGCC | CCGCGCCACG | TCACAAACTC | CACCCCCTCA | 550 |
| TTATCATATT | GGCTTCAATC | CAAAATAAGG | TATATTATTG | ATGATGCTAG | 600 |
| CATCATCAAT | AATATACCTT | ATTTTGGATT | GAAGCCAATA | TGATAATGAG | 650 |
| GGGGTGGAGT | TTGTGACGTG | GCGCGGGGCG | TGGGAACGGG | GCGGGTGACG | 700 |
| TAGTAGTGTG | GCGGAAGTGT | GATGTTGCAA | GTGTGGCGGA | ACACATGTAA | 750 |
| GCGACGGATG | TGGCAAAAGT | GACGTTTTTG | GTGTGCGCCG | GTGTACACAG | 800 |
| GAAGTGACAA | TTTTCGCGCG | GTTTTAGGCG | GATGTTGTAG | TAAATTTGGG | 850 |
| CGTAACCGAG | TAAGATTTGG | CCATTTTCGC | GGGAAAACTG | AATAAGAGGA | 900 |
| AGTGAAATCT | GAATAATTTT | GTGTTACTCA | TAGCGCGTAA | TATTTGTCTA | 950 |
| GGGAGATCAG | CCTGCAGGTC | GTTACATAAC | TTACGGTAAA | TGGCCCGCCT | 1000 |
| GGCTGACCGC | CCAACGACCC | CCGCCCATTG | ACGTCAATAA | TGACGTATGT | 1050 |
| TCCCATAGTA | ACGCCAATAG | GGACTTTCCA | TTGACGTCAA | TGGGTGGAGT | 1100 |
| ATTTACGGTA | AACTGCCCAC | TTGGCAGTAC | ATCAAGTGTA | TCATATGCCA | 1150 |
| AGTACGCCCC | CTATTGACGT | CAATGACGGT | AAATGGCCCG | CCTGGCATTA | 1200 |
| TGCCCAGTAC | ATGACCTTAT | GGACTTTCC | TACTTGGCAG | TACATCTACG | 1250 |
| TATTAGTCAT | CGCTATTACC | ATGGTGATGC | GGTTTTGGCA | GTACATCAAT | 1300 |

FIGURE 5B

```
GGGCGTGGAT AGCGGTTTGA CTCACGGGGA TTTCCAAGTC TCCACCCCAT    1350
TGACGTCAAT GGGAGTTTGT TTTGGCACCA AAATCAACGG GACTTTCCAA    1400
AATGTCGTAA CAACTCCGCC CCATTGACGC AAATGGGCGG TAGGCGTGTA    1450
CGGTGGGAGG TCTATATAAG CAGAGCTCGT TTAGTGAACC GTCAGATCGC    1500
CTGGAGACGC CATCCACGCT GTTTTGACCT CCATAGAAGA CACCGGGACC    1550
GATCCAGCCT CCGGACTCTA GAGGATCCGG TACTCGAGGA ACTGAAAAAC    1600
CAGAAAGTTA ACTGGTAAGT TTAGTCTTTT TGTCTTTTAT TTCAGGTCCC    1650
GGATCCGGTG GTGGTGCAAA TCAAAGAACT GCTCCTCAGT GGATGTTGCC    1700
TTTACTTCTA GGCCTGTACG GAAGTGTTAC TTCTGCTCTA AAAGCTGCGG    1750
AATTGTACCC GCGGCCGCAA TTCCCGGGGA TCGAAGAGC CTGCTAAAGC    1800
AAAAAGAAG TCACCATGTC GTTTACTTTG ACCAACAAGA ACGTGATTTT    1850
CGTTGCCGGT CTGGGAGGCA TTGGTCTGGA CACCAGCAAG GAGCTGCTCA    1900
AGCGCGATCC CGTCGTTTTA CAACGTCGTG ACTGGGAAAA CCCTGGCGTT    1950
ACCCAACTTA ATCGCCTTGC AGCACATCCC CCTTTCGCCA GCTGGCGTAA    2000
TAGCGAAGAG GCCCGCACCG ATCGCCCTTC CAACAGTTG CGCAGCCTGA    2050
ATGGCGAATG GCGCTTTGCC TGGTTTCCGG CACCAGAAGC GGTGCCGGAA    2100
AGCTGGCTGG AGTGCGATCT TCCTGAGGCC GATACTGTCG TCGTCCCCTC    2150
AAACTGGCAG ATGCACGGTT ACGATGCGCC CATCTACACC AACGTAACCT    2200
ATCCCATTAC GGTCAATCCG CCGTTTGTTC CCACGGAGAA TCCGACGGGT    2250
TGTTACTCGC TCACATTTAA TGTTGATGAA AGCTGGCTAC AGGAAGGCCA    2300
GACGCGAATT ATTTTTGATG GCGTTAACTC GGCGTTTCAT CTCTGGTGCA    2350
ACGGGCGCTG GGTCGGTTAC GGCCAGGACA GTCGTTTGCC GTCTGAATTT    2400
GACCTGAGCG CATTTTTACG CGCCGGAGAA AACCGCCTCG CGGTGATGGT    2450
GCTGCGTTGG AGTGACGGCA GTTATCTGGA AGATCAGGAT ATGTGGCGGA    2500
TGAGCGGCAT TTTCCGTGAC GTCTCGTTGC TGCATAAACC GACTACACAA    2550
ATCAGCGATT TCCATGTTGC CACTCGCTTT AATGATGATT TCAGCCGCGC    2600
```

FIGURE 5C

| | | | | | |
|---|---|---|---|---|---|
| TGTACTGGAG | GCTGAAGTTC | AGATGTGCGG | CGAGTTGCGT | GACTACCTAC | 2650 |
| GGGTAACAGT | TTCTTTATGG | CAGGGTGAAA | CGCAGGTCGC | CAGCGGCACC | 2700 |
| GCGCCTTTCG | GCGGTGAAAT | TATCGATGAG | CGTGGTGGTT | ATGCCGATCG | 2750 |
| CGTCACACTA | CGTCTGAACG | TCGAAACCC | GAAACTGTGG | AGCGCCGAAA | 2800 |
| TCCCGAATCT | CTATCGTGCG | GTGGTTGAAC | TGCACACCGC | CGACGGCACG | 2850 |
| CTGATTGAAG | CAGAAGCCTG | CGATGTCGGT | TTCCGCGAGG | TGCGGATTGA | 2900 |
| AAATGGTCTG | CTGCTGCTGA | ACGGCAAGCC | GTTGCTGATT | CGAGGCGTTA | 2950 |
| ACCGTCACGA | GCATCATCCT | CTGCATGGTC | AGGTCATGGA | TGAGCAGACC | 3000 |
| ATGGTGCAGG | ATATCCTGCT | GATGAAGCAG | AACAACTTTA | ACGCCGTGCG | 3050 |
| CTGTTCGCAT | TATCCGAACC | ATCCGCTGTG | GTACACGCTG | TGCGACCGCT | 3100 |
| ACGGCCTGTA | TGTGGTGGAT | GAAGCCAATA | TTGAAACCCA | CGGCATGGTG | 3150 |
| CCAATGAATC | GTCTGACCGA | TGATCCGCGC | TGGCTACCGG | CGATGAGCGA | 3200 |
| ACGCGTAACG | CGAATGGTGC | AGCGCGATCG | TAATCACCCG | AGTGTGATCA | 3250 |
| TCTGCTCGCT | GGGGAATGAA | TCAGGCCACG | GCGCTAATCA | CGACGCGCTG | 3300 |
| TATCGCTGGA | TCAAATCTGT | CGATCCTTCC | CGCCCGGTGC | AGTATGAAGG | 3350 |
| CGGCGGAGCC | GACACCACGG | CCACCGATAT | TATTTGCCCG | ATGTACGCGC | 3400 |
| GCGTGGATGA | AGACCAGCCC | TTCCCGGCTG | TGCCGAAATG | GTCCATCAAA | 3450 |
| AAATGGCTTT | CGCTACCTGG | AGAGACGCGC | CCGCTGATCC | TTTGCGAATA | 3500 |
| CGCCCACGCG | ATGGGTAACA | GTCTTGGCGG | TTTCGCTAAA | TACTGGCAGG | 3550 |
| CGTTTCGTCA | GTATCCCCGT | TTACAGGGCG | GCTTCGTCTG | GACTGGGTG | 3600 |
| GATCAGTCGC | TGATTAAATA | TGATGAAAAC | GGCAACCCGT | GGTCGGCTTA | 3650 |
| CGGCGGTGAT | TTTGGCGATA | CGCCGAACGA | TCGCCAGTTC | TGTATGAACG | 3700 |
| GTCTGGTCTT | TGCCGACCGC | ACGCCGCATC | CAGCGCTGAC | GGAAGCAAAA | 3750 |
| CACCAGCAGC | AGTTTTTCCA | GTTCCGTTTA | TCCGGGCAAA | CCATCGAAGT | 3800 |
| GACCAGCGAA | TACCTGTTCC | GTCATAGCGA | TAACGAGCTC | CTGCACTGGA | 3850 |
| TGGTGGCGCT | GGATGGTAAG | CCGCTGGCAA | GCGGTGAAGT | GCCTCTGGAT | 3900 |

FIGURE 5D

```
GTCGCTCCAC AAGGTAAACA GTTGATTGAA CTGCCTGAAC TACCGCAGCC    3950
GGAGAGCGCC GGGCAACTCT GGCTCACAGT ACGCGTAGTG CAACCGAACG    4000
CGACCGCATG GTCAGAAGCC GGGCACATCA GCGCCTGGCA GCAGTGGCGT    4050
CTGGCGGAAA ACCTCAGTGT GACGCTCCCC GCCGCGTCCC ACGCCATCCC    4100
GCATCTGACC ACCAGCGAAA TGGATTTTTG CATCGAGCTG GGTAATAAGC    4150
GTTGGCAATT TAACCGCCAG TCAGGCTTTC TTTCACAGAT GTGGATTGGC    4200
GATAAAAAAC AACTGCTGAC GCCGCTGCGC GATCAGTTCA CCCGTGCACC    4250
GCTGGATAAC GACATTGGCG TAAGTGAAGC GACCCGCATT GACCCTAACG    4300
CCTGGGTCGA ACGCTGGAAG GCGGCGGGCC ATTACCAGGC CGAAGCAGCG    4350
TTGTTGCAGT GCACGGCAGA TACACTTGCT GATGCGGTGC TGATTACGAC    4400
CGCTCACGCG TGGCAGCATC AGGGGAAAAC CTTATTTATC AGCCGGAAAA    4450
CCTACCGGAT TGATGGTAGT GGTCAAATGG CGATTACCGT TGATGTTGAA    4500
GTGGCGAGCG ATACACCGCA TCCGGCGCGG ATTGGCCTGA ACTGCCAGCT    4550
GGCGCAGGTA GCAGAGCGGG TAAACTGGCT CGGATTAGGG CCGCAAGAAA    4600
ACTATCCCGA CCGCCTTACT GCCGCCTGTT TTGACCGCTG GATCTGCCA     4650
TTGTCAGACA TGTATACCCC GTACGTCTTC CCGAGCGAAA ACGGTCTGCG    4700
CTGCGGGACG CGCGAATTGA ATTATGGCCC ACACCAGTGG CGCGGCGACT    4750
TCCAGTTCAA CATCAGCCGC TACAGTCAAC AGCAACTGAT GGAAACCAGC    4800
CATCGCCATC TGCTGCACGC GGAAGAAGGC ACATGGCTGA ATATCGACGG    4850
TTTCCATATG GGGATTGGTG GCGACGACTC CTGGAGCCCG TCAGTATCGG    4900
CGGAATTACA GCTGAGCGCC GGTCGCTACC ATTACCAGTT GGTCTGGTGT    4950
CAAAAATAAT AATAACCGGG CAGGCCATGT CTGCCCGTAT TTCGCGTAAG    5000
GAAATCCATT ATGTACTATT TAAAAACAC AAACTTTTGG ATGTTCGGTT     5050
TATTCTTTTT CTTTTACTTT TTTATCATGG GAGCCTACTT CCCGTTTTTC    5100
CCGATTTGGC TACATGACAT CAACCATATC AGCAAAAGTG ATACGGGTAT    5150
TATTTTTGCC GCTATTTCTC TGTTCTCGCT ATTATTCCAA CCGCTGTTTG    5200
GTCTGCTTTC TGACAAACTC GGCCTCGACT CTAGGCGGCC GCGGGATCC    5250
```

FIGURE 5E

```
AGACATGATA AGATACATTG ATGAGTTTGG ACAAACCACA ACTAGAATGC    5300
AGTGAAAAAA ATGCTTTATT TGTGAAATTT GTGATGCTAT TGCTTTATTT    5350
GTAACCATTA TAAGCTGCAA TAAACAAGTT AACAACAACA ATTGCATTCA    5400
TTTTATGTTT CAGGTTCAGG GGGAGGTGTG GGAGGTTTTT TCGGATCCTC    5450
TAGAGTCGAC GACGCGAGGC TGGATGGCCT TCCCCATTAT GATTCTTCTC    5500
GCTTCCGGCG GCATCGGGAT GCCCGCGTTG CAGGCCATGC TGTCCAGGCA    5550
GGTAGATGAC GACCATCAGG GACAGCTTCA AGGATCGCTC GCGGCTCTTA    5600
CCAGCCTAAC TTCGATCACT GGACCGCTGA TCGTCACGGC GATTTATGCC    5650
GCCTCGGCGA GCACATGGAA CGGGTTGGCA TGGATTGTAG GCGCCGCCCT    5700
ATACCTTGTC TGCCTCCCCG CGTTGCGTCG CGGTGCATGG AGCCGGGCCA    5750
CCTCGACCTG AATGGAAGCC GGCGGCACCT CGCTAACGGA TTCACCACTC    5800
CAAGAATTGG AGCCAATCAA TTCTTGCGGA GAACTGTGAA TGCGCAAACC    5850
AACCCTTGGC AGAACATATC CATCGCGTCC GCCATCTCCA GCAGCCGCAC    5900
GCGGCGCATC TCGGGCAGCG TTGGGTCCTG GCCACGGGTG CGCATGATCG    5950
TGCTCCTGTC GTTGAGGACC CGGCTAGGCT GGCGGGGTTG CCTTACTGGT    6000
TAGCAGAATG AATCACCGAT ACGCGAGCGA ACGTGAAGCG ACTGCTGCTG    6050
CAAAACGTCT GCGACCTGAG CAACAACATG AATGGTCTTC GGTTTCCGTG    6100
TTTCGTAAAG TCTGGAAACG CGGAAGTCAG CGCCCTGCAC CATTATGTTC    6150
CGGATCTGCA TCGCAGGATG CTGCTGGCTA CCCTGTGGAA CACCTACATC    6200
TGTATTAACG AAGCCTTTCT CAATGCTCAC GCTGTAGGTA TCTCAGTTCG    6250
GTGTAGGTCG TTCGCTCCAA GCTGGGCTGT GTGCACGAAC CCCCCGTTCA    6300
GCCCGACCGC TGCGCCTTAT CCGGTAACTA TCGTCTTGAG TCCAACCCGG    6350
TAAGACACGA CTTATCGCCA CTGGCAGCAG CCACTGGTAA CAGGATTAGC    6400
AGAGCGAGGT ATGTAGGCGG TGCTACAGAG TTCTTGAAGT GGTGGCCTAA    6450
CTACGGCTAC ACTAGAAGGA CAGTATTTGG TATCTGCGCT CTGCTGAAGC    6500
CAGTTACCTT CGGAAAAGA GTTGGTAGCT CTTGATCCGG CAAACAAACC     6550
```

FIGURE 5F

```
ACCGCTGGTA GCGGTGGTTT TTTTGTTTGC AAGCAGCAGA TTACGCGCAG   6600
AAAAAAGGA  TCTCAAGAAG ATCCTTTGAT CTTTTCTACG GGGTCTGACG    6650
CTCAGTGGAA CGAAAACTCA CGTTAAGGGA TTTTGGTCAT GAGATTATCA   6700
AAAAGGATCT TCACCTAGAT CCTTTTAAAT TAAAAATGAA GTTTTAAATC   6750
AATCTAAAGT ATATATGAGT AAACTTGGTC TGACAGTTAC CAATGCTTAA   6800
TCAGTGAGGC ACCTATCTCA GCGATCTGTC TATTTCGTTC ATCCATAGTT   6850
GCCTGACTCC CCGTCGTGTA GATAACTACG ATACGGGAGG GCTTACCATC   6900
TGGCCCCAGT GCTGCAATGA TACCGCGAGA CCCACGCTCA CCGGCTCCAG   6950
ATTTATCAGC AATAAACCAG CCAGCCGGAA GGGCCGAGCG CAGAAGTGGT   7000
CCTGCAACTT TATCCGCCTC CATCCAGTCT ATTAATTGTT GCCGGGAAGC   7050
TAGAGTAAGT AGTTCGCCAG TTAATAGTTT GCGCAACGTT GTTGCCATTG   7100
CTGCAGGCAT CGTGGTGTCA CGCTCGTCGT TTGGTATGGC TTCATTCAGC   7150
TCCGGTTCCC AACGATCAAG GCGAGTTACA TCATCCCCCA TGTTGTGCAA   7200
AAAAGCGGTT AGCTCCTTCG GTCCTCCGAT CGTTGTCAGA AGTAAGTTGG   7250
CCGCAGTGTT ATCACTCATG GTTATGCCAG CACTGCATAA TTCTCTTACT   7300
GTCATGCCAT CCGTAAGATG CTTTTCTGTG ACTGGTGAGT ACTCAACCAA   7350
GTCATTCTGA GAATAGTGTA TGCGGCGACC GAGTTGCTCT TGCCCGGCGT   7400
CAACACGGGA TAATACCGCG CCACATAGCA CAACTTTAAA AGTGCTCATC   7450
ATTGGAAAAC GTTCTTCGGG GCGAAAACTC TCAAGGATCT TACCGCTGTT   7500
GAGATCCAGT TCGATGTAAC CCACTCGTGC ACCCAACTGA TCTTCAGCAT   7550
CTTTTACTTT CACCAGCGTT TCTGGGTGAG CAAAAACAGG AAGGCAAAAT   7600
GCCGCAAAAA AGGGAATAAG GGCGACACGG AAATGTTGAA TACTCATACT   7650
CTTCCTTTTT CAATATTATT GAAGCATTTA TCAGGGTTAT TGTCTCATGA   7700
GCGGATACAT ATTTGAATGT ATTTAGAAAA ATAAACAAAT AGGGGTTCCG   7750
CGCACATTTC CCCGAAAAGT GCCACCTGAC GTCTAAGAAA CCATTATTAT   7800
CATGACATTA ACCTATAAAA ATAGGCGTAT CACGAGGCCC TTTCGTCTTC   7850
AA                                                     7852
```

FIGURE 7A

```
TCTTCCGCTT CCTCGCTCAC TGACTCGCTG CGCTCGGTCG TTCGGCTGCG    50
GCGAGCGGTA TCAGCTCACT CAAAGGCGGT AATACGGTTA TCCACAGAAT   100
CAGGGGATAA CGCAGGAAAG AACATGTGAG CAAAAGGCCA GCAAAAGGCC   150
AGGAACCGTA AAAGGCCGC GTTGCTGGCG TTTTTCCATA GGCTCCGCCC    200
CCCTGACGAG CATCACAAAA ATCGACGCTC AAGTCAGAGG TGGCGAAACC   250
CGACAGGACT ATAAAGATAC CAGGCGTTTC CCCTGGAAG CTCCCTCGTG    300
CGCTCTCCTG TTCCGACCCT GCCGCTTACC GGATACCTGT CCGCCTTTCT   350
CCCTTCGGGA AGCGTGGCGC TTTCTCATAG CTCACGCTGT AGGTATCTCA   400
GTTCGGTGTA GGTCGTTCGC TCCAAGCTGG GCTGTGTGCA CGAACCCCCC   450
GTTCAGCCCG ACCGCTGCGC CTTATCCGGT AACTATCGTC TTGAGTCCAA   500
CCCGGTAAGA CACGACTTAT CGCCACTGGC AGCAGCCACT GGTAACAGGA   550
TTAGCAGAGC GAGGTATGTA GGCGGTGCTA CAGAGTTCTT GAAGTGGTGG   600
CCTAACTACG GCTACACTAG AAGAACAGTA TTTGGTATCT GCGCTCTGCT   650
GAAGCCAGTT ACCTTCGGAA AAAGAGTTGG TAGCTCTTGA TCCGGCAAAC   700
AAACCACCGC TGGTAGCGGT GGTTTTTTG TTTGCAAGCA GCAGATTACG    750
CGCAGAAAAA AAGGATCTCA AGAAGATCCT TTGATCTTTT CTACGGGGTC   800
TGACGCTCAG TGGAACGAAA ACTCACGTTA AGGGATTTTG GTCATGAGAT   850
TATCAAAAAG GATCTTCACC TAGATCCTTT TAAATTAAAA ATGAAGTTTT   900
AAATCAATCT AAAGTATATA TGAGTAAACT TGGTCTGACA GTTACCAATG   950
CTTAATCAGT GAGGCACCTA TCTCAGCGAT CTGTCTATTT CGTTCATCCA  1000
TAGTTGCCTG ACTCCCCGTC GTGTAGATAA CTACGATACG GGAGGGCTTA  1050
CCATCTGGCC CCAGTGCTGC AATGATACCG CCAGACCCAC GCTCACCGGC  1100
TCCAGATTTA TCAGCAATAA ACCAGCCAGC CGGAAGGGCC GAGCGCAGAA  1150
GTGGTCCTGC AACTTTATCC GCCTCCATCC AGTCTATTAA TTGTTGCCGG  1200
GAAGCTAGAG TAAGTAGTTC GCCAGTTAAT AGTTTGCGCA ACGTTGTTGC  1250
CATTGCTACA GGCATCGTGG TGTCACGCTC GTCGTTTGGT ATGGCTTCAT  1300
```

FIGURE 7B

```
TCAGCTCCGC TTCCCAACGA TCAAGGCGAG TTACATGATC CCCCATGTTG    1350
TGCAAAAAAG CGGTTAGCTC CTTCGGTCCT CCGATCGTTG TCAGAAGTAA    1400
GTTGGCCGCA GTGTTATCAC TCATGGTTAT GGCAGCACTG CATAATTCTC    1450
TTACTGTCAT GCCATCCGTA AGATGCTTTT CTGTGACTGG TGAGTACTCA    1500
ACCAAGTCAT TCTGAGAATA GTGTATGCGG CGACCGAGTT GCTCTTGCCC    1550
GGCGTCAATA CGGGATAATA CCGCGCCACA TAGCAGAACT TTAAAAGTGC    1600
TCATCATTGG AAAACGTTCT TCGGGGCGAA AACTCTCAAG GATCTTACCG    1650
CTGTTGAGAT CCAGTTCGAT GTAACCCACT CGTGCACCCA ACTGATCTTC    1700
AGCATCTTTT ACTTTCACCA GCGTTTCTGG GTGAGCAAAA ACAGGAAGGC    1750
AAAATGCCGC AAAAAAGGGA ATAAGGGCGA CACGGAAATG TTGAATACTC    1800
ATACTCTTCC TTTTTCAATA TTATTGAAGC ATTTATCAGG GTTATTGTCT    1850
CATGAGCGGA TACATATTTG AATGTATTTA GAAAAATAAA CAAATAGGGG    1900
TTCCGCGCAC ATTTCCCCGA AAAGTGCCAC CTGACGTCTA AGAAACCATT    1950
ATTATCATGA CATTAACCTA TAAAAATAGG CGTATCACGA GGCCCTTTCG    2000
TCTCGCGCGT TTCGGTGATG ACGGTGAAAA CCTCTGACAC ATGCAGCTCC    2050
CGGAGACGGT CACAGCTTGT CTGTAAGCGG ATGCCGGGAG CAGACAAGCC    2100
CGTCAGGGCG CGTCAGCGGG TGTTGGCGGG TGTCGGGCT GGCTTAACTA     2150
TGCGGCATCA GAGCAGATTG TACTGAGAGT GCACCATAAA ATTGTAAACG    2200
TTAATATTTT GTTAAAATTC GCGTTAAATT TTTGTTAAAT CAGCTCATTT    2250
TTTAACCAAT AGGCCGAAAT CGGCAAAATC CCTTATAAAT CAAAAGAATA    2300
GCCCGAGATA GGGTTGAGTG TTGTTCCAGT TTGGAACAAG AGTCCACTAT    2350
TAAAGAACGT GGACTCCAAC GTCAAAGGGC GAAAAACCGT CTATCAGGGC    2400
GATGGCCCAC TACGTGAACC ATCACCCAAA TCAAGTTTTT TGGGGTCGAG    2450
GTGCCGTAAA GCACTAAATC GGAACCCTAA AGGGAGCCCC CGATTTAGAG    2500
CTTGACGGGG AAAGCCGGCG AACGTGGCGA GAAGGAAGG GAAGAAAGCG    2550
AAAGGAGCGG GCGCTAGGGC GCTGGCAAGT GTAGCGGTCA CGCTGCGCGT    2600
```

FIGURE 7C

| | | | | | |
|---|---|---|---|---|---|
| AACCACCACA | CCCGCCGCGC | TTAATGCGCC | GCTACAGGGC | GCGTACTATG | 2650 |
| GTTGCTTTGA | CGTATGCGGT | GTGAAATACC | GCACAGATGC | GTAAGGAGAA | 2700 |
| AATACCGCAT | CAGGCGCCAT | TCGCCATTCA | GGCTGCGCAA | CTGTTGGGAA | 2750 |
| GGGCGATCGG | TGCGGGCCTC | TTCGCTATTA | CGCCAGCTGG | CGAAAGGGGG | 2800 |
| ATGTGCTGCA | AGGCGATTAA | GTTGGGTAAC | GCCAGGGTTT | TCCCAGTCAC | 2850 |
| GACGTTGTAA | AACGACGGCC | AGTGCCAAGC | TTAAGGTGCA | CGGCCCACGT | 2900 |
| GGCCACTAGT | ACTTCTCGAG | CTCTGTACAT | GTCCGCGGTC | GCGACGTACG | 2950 |
| CGTATCGATG | GCGCCAGCTG | CAGGCGGCCG | CCATATGCAT | CCTAGGCCTA | 3000 |
| TTAATATTCC | GGAGTATACG | TAGCCGGCTA | ACGTTAACAA | CCGGTACCTC | 3050 |
| TAGAACTATA | GCTAGCCAAT | TCCATCATCA | ATAATATACC | TTATTTTGGA | 3100 |
| TTGAAGCCAA | TATGATAATG | AGGGGGTGGA | GTTTGTGACG | TGGCGCGGGG | 3150 |
| CGTGGGAACG | GGGCGGGTGA | CGTAGGTTTT | AGGGCGGAGT | AACTTGTATG | 3200 |
| TGTTGGGAAT | TGTAGTTTTC | TTAAAATGGG | AAGTTACGTA | ACGTGGGAAA | 3250 |
| ACGGAAGTGA | CGATTTGAGG | AAGTTGTGGG | TTTTTTGGCT | TTCGTTTCTC | 3300 |
| GGCGTAGGTT | CGCGTGCGGT | TTTCTGGGTG | TTTTTTGTGG | ACTTTAACCG | 3350 |
| TTACGTCATT | TTTTAGTCCT | ATATATACTC | GCTCTGCACT | TGGCCCTTTT | 3400 |
| TTACACTGTG | ACTGATTGAG | CTGGTGCCGT | GTCGAGTGGT | GTTTTTTTAA | 3450 |
| TAGGTTTTCT | TTTTTACTGG | TAAGGCTGAC | TGTTAGGCTG | CCGCTGTGAA | 3500 |
| GCGCTGTATG | TTGTTCTGGA | GCGGGAGGGT | GCTATTTTGC | CTAGGCAGGA | 3550 |
| GGGTTTTTCA | GGTGTTTATG | TGTTTTTCTC | TCCTATTAAT | TTTGTTATAC | 3600 |
| CTCCTATGGG | GGCTGTAATG | TTGTCTCTAC | GCCTGCGGGT | ATGTATTCCC | 3650 |
| CCCAAGCTTG | CATGCCTGCA | GGTCGACTCT | AGAGGATCCG | AAAAAACCTC | 3700 |
| CCACACCTCC | CCCTGAACCT | GAAACATAAA | ATGAATGCAA | TTGTTGTTGT | 3750 |
| TAACTTGTTT | ATTGCAGCTT | ATAATGGTTA | CAAATAAAGC | AATAGCATCA | 3800 |
| CAAATTTCAC | AAATAAAGCA | TTTTTTTCAC | TGCATTCTAG | TTGTGGTTTG | 3850 |
| TCCAAACTCA | TCAATGTATC | TTATCATGTC | TGGATCCCCC | TAGCTTGCCA | 3900 |

FIGURE 7D

| | | | | | |
|---|---|---|---|---|---|
| AACCTACAGG | TGGGGTCTTT | CATTCCCCCC | TTTTTCTGGA | GACTAAATAA | 3950 |
| AATCTTTTAT | TTTATCTATG | GCTCGTACTC | TATAGGCTTC | AGCTGGTGAT | 4000 |
| ATTGTTGAGT | CAAAACTAGA | GCCTGGACCA | CTGATATCCT | GTCTTTAACA | 4050 |
| AATTGGACTA | ATCGCGGGAT | CAGCCAATTC | CATGAGCAAA | TGTCCCATGT | 4100 |
| CAACATTTAT | GCTGCTCTCT | AAAGCCTTGT | ATCTTGCATC | TCTTCTTCTG | 4150 |
| TCTCCTCTTT | CAGAGCAGCA | ATCTGGGGCT | TAGACTTGCA | CTTGCTTGAG | 4200 |
| TTCCGGTGGG | GAAAGAGCTT | CACCCTGTCG | GAGGGGCTGA | TGGCTTGCCG | 4250 |
| GAAGAGGCTC | CTCTCGTTCA | GCAGTTTCTG | GATGGAATCG | TACTGCCGCA | 4300 |
| CTTTGTTCTC | TTCTATGACC | AAAAATTGTT | GGCATTCCAG | CATTGCTTCT | 4350 |
| ATCCTGTGTT | CACAGAGAAT | TACTGTGCAA | TCAGCAAATG | CTTGTTTTAG | 4400 |
| AGTTCTTCTA | ATTATTTGGT | ATGTTACTGG | ATCCAAATGA | GCACTGGGTT | 4450 |
| CATCAAGCAG | CAAGATCTTC | GCCTTACTGA | GAACAGATCT | AGCCAAGCAC | 4500 |
| ATCAACTGCT | TGTGGCCATG | GCTTAGGACA | CAGCCCCCAT | CCACAAGGAC | 4550 |
| AAAGTCAAGC | TTCCCAGGAA | ACTGTTCTAT | CACAGATCTG | AGCCCAACCT | 4600 |
| CATCTGCAAC | TTTCCATATT | TCTTGATCAC | TCCACTGTTC | ATAGGGATCC | 4650 |
| AAGTTTTTTC | TAAATGTTCC | AGAAAAAATA | AATACTTTCT | GTGGTATCAC | 4700 |
| TCCAAAGGCT | TTCCTCCACT | GTTGCAAAGT | TATTGAATCC | CAAGACACAC | 4750 |
| CATCGATCTG | GATTTCTCCT | TCAGTGTTCA | GTAGTCTCAA | AAAAGCTGAT | 4800 |
| AACAAAGTAC | TCTTCCCTGA | TCCAGTTCTT | CCCAAGAGGC | CCACCCTCTG | 4850 |
| GCCAGGACTT | ATTGAGAAGG | AAATGTTCTC | TAATATGGCA | TTTCCACCTT | 4900 |
| CTGTGTATTT | TGCTGTGAGA | TCTTTGACAG | TCATTTGGCC | CCCTGAGGGC | 4950 |
| CAGATGTCAT | CTTTCTTCAC | GTGTGAATTC | TCAATAATCA | TAACTTTCGA | 5000 |
| GAGTTGGCCA | TTCTTGTATG | GTTTGGTTGA | CTTGGTAGGT | TTACCTTCTG | 5050 |
| TTGGCATGTC | AATGAACTTA | AAGACTCGGC | TCACAGATCG | CATCAAGCTA | 5100 |
| TCCACATCTA | TGCTGGAGTT | TACAGCCCAC | TGCAATGTAC | TCATGATATT | 5150 |
| CATGGCTAAA | GTCAGGATAA | TACCAACTCT | TCCTTCTCCT | TCTCCTGTTG | 5200 |

FIGURE 7E

```
TTAAAATGGA AATGAAGGTA ACAGCAATGA AGAAGATGAC AAAAATCATT    5250

TCTATTCTCA TTTGGAACCA GCGCAGTGTT GACAGGTACA AGAACCAGTT    5300

GGCAGTATGT AAATTCAGAG CTTTGTGGAA CAGAGTTTCA AAGTAAGGCT    5350

GCCGTCCGAA GGCACGAAGT GTCCATAGTC CTTTTAAGCT TGTAACAAGA    5400

TGAGTGAAAA TTGGACTCCT GCCTTCAGAT TCCAGTTGTT TGAGTTGCTG    5450

TGAGGTTTGG AGGAAATATG CTCTCAACAT AATAAAGCC ACTATCACTG     5500

GCACTGTTGC AACAAGATG TAGGGTTGTA AAACTGCGAC AACTGCTATA     5550

GCTCCAATCA CAATTAATAA CAACTGGATG AAGTCAAATA TGGTAAGAGG    5600

CAGAAGGTCA TCCAAAATTG CTATATCTTT GGAGAATCTA TTAAGAATCC    5650

CACCTGCTTT CAACGTGTTG AGGGTTGACA TAGGTGCTTG AAGAACAGAA    5700

TGTAACATTT TGTGGTGTAA AATTTTCGAC ACTGTGATTA GAGTATGCAC    5750

CAGTGGTAGA CCTCTGAAGA ATCCATAGC AAGCAAAGTG TCGGCTACTC     5800

CCACGTAAAT GTAAAACACA TAATACGAAC TGGTGCTGGT GATAATCACT    5850

GCATAGCTGT TATTTCTACT ATGAGTACTA TTCCCTTTGT CTTGAAGAGG    5900

AGTGTTTCCA AGGAGCCACA GCACAACCAA AGAAGCAGCC ACCTCTGCCA    5950

GAAAAATTAC TAAGCACCAA ATTAGCACAA AAATTAAGCT CTTGTGGACA    6000

GTAATATATC GAAGGTATGT GTTCCATGTA GTCACTGCTG GTATGCTCTC    6050

CATATCATCA AAAAGCACT CCTTTAAGTC TTCTTCGTTA ATTTCTTCAC     6100

TTATTTCCAA GCCAGTTTCT TGAGATAACC TTCTTGAATA TATATCCAGT    6150

TCAGTCAAGT TTGCCTGAGG GGCCAGTGAC ACTTTTCGTG TGGATGCTGT    6200

TGTCTTTCGG TGAATGTTCT GACCTTGGTT AACTGAGTGT GTCATCAGGT    6250

TCAGGACAGA CTGCCTCCTT CGTGCCTGAA GCGTGGGCC AGTGCTGATC     6300

ACGCTGATGC GAGGCAGTAT CGCCTCTCCC TGCTCAGAAT CTGGTACTAA    6350

GGACAGCCTT CTCTCTAAAG GCTCATCAGA ATCCTCTTCG ATGCCATTCA    6400

TTTGTAAGGG AGTCTTTTGC ACAATGGAAA ATTTTCGTAT AGAGTTGATT    6450

GGATTGAGAA TAGAATTCTT CCTTTTTTCC CCAAACTCTC CAGTCTGTTT    6500
```

FIGURE 7F

```
AAAAGATTGT TTTTTTGTTT CTGTCCAGGA GACAGGAGCA TCTCCTTCTA    6550
ATGAGAAACG GTGTAAGGTC TCAGTTAGGA TTGAATTTCT TCTTTCTGCA    6600
CTAAATTGGT CGAAAGAATC ACATCCCATG AGTTTTGAGC TAAAGTCTGG    6650
CTGTAGATTT TGGAGTTCTG AAAATGTCCC ATAAAAATAG CTGCTACCTT    6700
CATGCAAAAT TAATATTTTG TCAGCTTTCT TTAAATGTTC CATTTTAGAA    6750
GTGACCAAAA TCCTAGTTTT GTTAGCCATC AGTTTACAGA CACAGCTTTC    6800
AAATATTTCT TTTTCTGTTA AAACATCTAG GTATCCAAAA GGAGAGTCTA    6850
ATAAATACAA ATCAGCATCT TTGTATACTG CTCTTGCTAA AGAAATTCTT    6900
GCTCGTTGAC CTCCACTCAG TGTGATTCCA CCTTCTCCAA GAACTATATT    6950
GTCTTTCTCT GCAAACTTGG AGATGTCCTC TTCTAGTTGG CATGCTTTGA    7000
TGACGCTTCT GTATCTATAT TCATCATAGG AAACACCAAA GATGATATTT    7050
TCTTTAATGG TGCCAGGCAT AATCCAGGAA AACTGAGAAC AGAATGAAAT    7100
TCTTCCACTG TGCTTAATTT TACCCTCTGA AGGCTCCAGT TCTCCCATAA    7150
TCATCATTAG AAGTGAAGTC TTGCCTGCTC CAGTGGATCC AGCAACCGCC    7200
AACAACTGTC CTCTTTCTAT CTTGAAATTA ATATCTTTCA GGACAGGAGT    7250
ACCAAGAAGT GAGAAATTAC TGAAGAAGAG GCTGTCATCA CCATTAGAAG    7300
TTTTTCTATT GTTATTGTTT TGTTTTGCTT TCTCAAATAA TTCCCCAAAT    7350
CCCTCCTCCC AGAAGGCTGT TACATTCTCC ATCACTACTT CTGTAGTCGT    7400
TAAGTTATAT TCCAATGTCT TATATTCTTG CTTTTGTAAG AAATCCTGTA    7450
TTTTGTTTAT TGCTCCAAGA GAGTCATACC ATGTTTGTAC AGCCCAGGGA    7500
AATTGCCGAG TGACCGCCAT GCGCAGAACA ATGCAGAATG AGATGGTGGT    7550
GAATATTTTC CGGAGGATGA TTCCTTTGAT TAGTGCATAG GGAAGCACAG    7600
ATAAAAACAC CACAAAGAAC CCTGAGAAGA AGAAGGCTGA GCTATTGAAG    7650
TATCTCACAT AGGCTGCCTT CCGAGTCAGT TTCAGTTCTG TTTGTCTTAA    7700
GTTTTCAATC ATTTTTTCCA TTGCTTCTTC CCAGCAGTAT GCCTTAACAG    7750
ATTGGATGTT CTCGATCATT TCTGAGGTAA TCACAAGTCT TTCACTGATC    7800
```

FIGURE 7G

```
TTCCCAGCTC TCTGATCTCT GTACTTCATC ATCATTCTCC CTAGCCCAGC    7850
CTGAAAAAGG GCAAGGACTA TCAGGAAACC AAGTCCACAG AAGGCAGACG    7900
CCTGTAACAA CTCCCAGATT AGCCCCATGA GGAGTGCCAC TTGCAAAGGA    7950
GCGATCCACA CGAAATGTGC CAATGCAAGT CCTTCATCAA ATTTGTTCAG    8000
GTTGTTGGAA AGGAGACTAA CAAGTTGTCC AATACTTATT TTATCTAGAA    8050
CACGGCTTGA CAGCTTTAAA GTCTTCTTAT AAATCAAACT AAACATAGCT    8100
ATTCTCATCT GCATTCCAAT GTGATGAAGG CCAAAATGG CTGGGTGTAG     8150
GAGCAGTGTC CTCACAATAA AGAGAAGGCA TAAGCCTATG CCTAGATAAA    8200
TCGCGATAGA GCGTTCCTCC TTGTTATCCG GGTCATAGGA AGCTATGATT    8250
CTTCCCAGTA AGAGAGGCTG TACTGCTTTG GTGACTTCCC CTAAATATAA    8300
AAAGATTCCA TAGAACATAA ATCTCCAGAA AAAACATCGC CGAAGGGCAT    8350
TAATGAGTTT AGGATTTTTC TTTGAAGCCA GCTCTCTATC CCATTCTCTT    8400
TCCAATTTTT CAGATAGATT GTCAGCAGAA TCAACAGAAG GGATTTGGTA    8450
TATGTCTGAC AATTCCAGGC GCTGTCTGTA TCCTTTCCTC AAAATTGGTC    8500
TGGTCCAGCT GAAAAAAGT TTGGAGACAA CGCTGGCCTT TTCCAGAGGC     8550
GACCTCTGCA TGGTCTCTCG GGCGCTGGGG TCCCTGCTAG GGCCGTCTGG    8600
GCTCAAGCTC CTAATGCCAA AGGAATTCCT GCAGCCCGGG GGATCCACTA    8650
GTTCTAGAGC GGCCGCCACC GCGGTGGCTG ATCCCGCTCC CGCCCGCCGC    8700
GCGCTTCGCT TTTTATAGGG CCGCCGCCGC CGCCGCCTCG CCATAAAAGG    8750
AAACTTTCGG AGCGCGCCGC TCTGATTGGC TGCCGCCGCA CCTCTCCGCC    8800
TCGCCCCGCC CCGCCCCTCG CCCCGCCCCG CCCCGCCTGG CGCGCGCCCC    8850
CCCCCCCCCC CCGCCCCCAT CGCTGCACAA ATAATTAAA AAATAAATAA     8900
ATACAAAATT GGGGGTGGGG AGGGGGGGA GATGGGAGA GTGAAGCAGA      8950
ACGTGGCCTC GAGTAGATGT ACTGCCAAGT AGGAAAGTCC CATAAGGTCA    9000
TGTACTGGGC ATAATGCCAG GCGGGCCATT TACCGTCATT GACGTCAATA    9050
GGGGGCGTAC TTGGCATATG ATACACTTGA TGTACTGCCA AGTGGGCAGT    9100
```

FIGURE 7H

```
TTACCGTAAA TACTCCACCC ATTGACGTCA ATGGAAAGTC CCTATTGGCG    9150
TTACTATGGG AACATACGTC ATTATTGACG TCAATGGGCG GGGGTCGTTG    9200
GGCGGTCAGC CAGGCGGGCC ATTTACCGTA AGTTATGTAA CGACCTGCAG    9250
GCTGATCTCC CTAGACAAAT ATTACGCGCT ATGAGTAACA CAAAATTATT    9300
CAGATTTCAC TTCCTCTTAT TCAGTTTTCC CGCGAAAATG GCCAAATCTT    9350
ACTCGGTTAC GCCCAAATTT ACTACAACAT CCGCCTAAAA CCGCGCGAAA    9400
ATTGTCACTT CCTGTGTACA CCGGCGCACA CCAAAAACGT CACTTTTGCC    9450
ACATCCGTCG CTTACATGTG TTCCGCCACA CTTGCAACAT CACACTTCCG    9500
CCACACTACT ACGTCACCCG CCCCGTTCCC ACGCCCCGCG CCACGTCACA    9550
AACTCCACCC CCTCATTATC ATATTGGCTT CAATCCAAAA TAAGGTATAT    9600
TATTGATGAT GCTAGCATGC GCAAATTTAA AGCGCTGATA TCGATCGCGC    9650
GCAGATCTGT CATGATGATC ATTGCAATTG GATCCATATA TAGGGCCCGG    9700
GTTATAATTA CCTCAGGTCG ACGTCCCATG GCCATTCGAA TTCGTAATCA    9750
TGGTCATAGC TGTTTCCTGT GTGAAATTGT TATCCGCTCA CAATTCCACA    9800
CAACATACGA GCCGGAAGCA TAAAGTGTAA AGCCTGGGGT GCCTAATGAG    9850
TGAGCTAACT CACATTAATT GCGTTGCGCT CACTGCCCGC TTTCCAGTCG    9900
GGAAACCTGT CGTGCCAGCT GCATTAATGA ATCGGCCAAC GCGCGGGGAG    9950
AGGCGGTTTG CGTATTGGGC GC                                 9972
```

FIGURE 12A

| | | | | | |
|---|---|---|---|---|---|
| CCAATTCCAT | CATCAATAAT | ATACCTTATT | TTGGATTGAA | GCCAATATGA | 50 |
| TAATGAGGGG | GTGGAGTTTG | TGACGTGGCG | CGGGGCGTGG | GAACGGGGCG | 100 |
| GGTGACGTAG | GTTTTAGGGC | GGAGTAACTT | GTATGTGTTG | GGAATTGTAG | 150 |
| TTTTCTTAAA | ATGGAAGTT | ACGTAACGTG | GGAAAACGGA | AGTGACGATT | 200 |
| TGAGGAAGTT | GTGGGTTTTT | TGGCTTTCGT | TTCTGGGCGT | AGGTTCGCGT | 250 |
| GCGGTTTTCT | GGGTGTTTTT | TGTGGACTTT | AACCGTTACG | TCATTTTTTA | 300 |
| GTCCTATATA | TACTCGCTCT | GCACTTGGCC | CTTTTTTACA | CTGTGACTGA | 350 |
| TTGAGCTGGT | GCCGTGTCGA | GTGGTGTTTT | TTTAATAGGT | TTTCTTTTTT | 400 |
| ACTGGTAAGG | CTGACTGTTA | GGCTGCCGCT | GTGAAGCGCT | GTATGTTGTT | 450 |
| CTGGAGCGGG | AGGGTGCTAT | TTTGCCTAGG | CAGGAGGGTT | TTTCAGGTGT | 500 |
| TTATGTGTTT | TTCTCTCCTA | TTAATTTTGT | TATACCTCCT | ATGGGGGCTG | 550 |
| TAATGTTGTC | TCTACGCCTG | CGGGTATGTA | TTCCCCCCAA | GCTTGCATGC | 600 |
| CTGCAGGTCG | ACTCTAGAGG | ATCCGAAAAA | ACCTCCCACA | CCTCCCCCTG | 650 |
| AACCTGAAAC | ATAAAATGAA | TGCAATTGTT | GTTGTTAACT | TGTTTATTGC | 700 |
| AGCTTATAAT | GGTTACAAAT | AAAGCAATAG | CATCACAAAT | TTCACAAATA | 750 |
| AAGCATTTTT | TTCACTGCAT | TCTAGTTGTG | GTTTGTCCAA | ACTCATCAAT | 800 |
| GTATCTTATC | ATGTCTGGAT | CCCCGCGGCC | GCTCTAGAAC | TAGTGGATCC | 850 |
| CCCGGGCTGC | AGGAATTCCG | TAACATAACT | GCGTGCTTTA | TTGAGATACA | 900 |
| CAGTAAAGCA | GTAATATAAT | ACAATAGTAA | GGCATATATT | TGGTGAAATC | 950 |
| TGATATGTTG | TGAAAATGCA | GTAAAACTGA | AGTTTAAAAA | AATAATTAGT | 1000 |
| AAATGTTACA | GTGTTGGTGT | TAAAACACAA | TCTATTATGA | TACTCAAGTA | 1050 |
| AGAGTCCAGT | ACCTGGAGAC | AATGATGATA | CATGCCATGT | GATGATTATG | 1100 |
| CTTCAGTTAC | ACTGATTATG | ATTTACACTT | TAATACTTGA | TGGTTATAAA | 1150 |
| GAACATGAAA | TGATGTCCAA | ATTATGCTTA | AAATCAGCAA | TAAAGCTCTC | 1200 |
| AGTTTTTATT | CAAATATTTT | GATAGATTCA | CTCCAGAACT | AATATCTAAA | 1250 |

FIGURE 12B

```
AGATAAAACG AAAAGATTAA AACAAAACTA TGCACTCTAT CTACCTTGGA    1300
TTTTAGAATG AAACTTAAAA CTTCTTAGTA GGAAAGGAAC CCCTTGTTTT    1350
AAATCTTGGT GAAAACAAAT CCTTGGATAA AGAAAATGCC CAGTGCCACA    1400
TAAAGGAGAG AGAGAGAGAA AAGCAAGACC AGAACCAAAT TTCAATTTGT    1450
TATCTTAGAG CTTTGGGTTT TCTTTTGGAA ATTATAAATG AAAAAAGGAA    1500
ACTGGTGTCC ACACAACAGA CAAGTGGTGA AGTTGTGAAA TTAGGTGTGC    1550
ACAATTACTA GAAACACCCC AAAACCAAAG TGAGGTAGAA ATAGCATGAG    1600
AAGCTGTGTT TGATGTTAAT TACAATTAAT AATGGACAAA ACCCACTCGC    1650
TAGAAGTTAA TTACACTTGA CGTTAGAGGT AACAGATTTG CAAAATGATA    1700
GGACAGTGAT TTCTATTGAG AGAATGCTCT TTAAATGCTA AGAAGAAGAA    1750
ACTGGCATGA GAGGAGTAAA GCTCTTCCTA GCAGTCCTTA GCTTTCTGTT    1800
GCACTTTTTC TCCTGGTTCA ATGACTTGCA TTTGTTTAGA CATTTCAGCC    1850
CGTCAACTAG ACCAGAGAGT TTGGAGACGC TTTTGCTCTC AAAACTTTCC    1900
AACCACTGTG CCTTCTCACC CACAATCCTG TGTGGAGTTA CTTGCAGGGA    1950
AACCAATGCA AAGGAGACAA ATGCAGTTCA TGGGCTTCTG GACTGATATT    2000
CACCAGGGTC ACAATGTGAT TGGGTTACTT TCTTAACAGT AATCCTAAGT    2050
CTTGCAGCAT TAAAAAAAAA AATCATCACA ATGAAGAAAA AAAAACCCAA    2100
AAAATCTAAA ATCTAAAATT CATCATCATC ATCAACAACA ACAACAACAA    2150
CAACAACAAA ACCACCCACT TCAGGTTGAG TTTATGAAGA GGGCAGAACA    2200
ATTTAGTTGT AATTATAGAG ATGTTTATAT GTATAGTTGT AAATATTCAT    2250
CCATTCTTTT ACAGAGTTGT TGCTCCCTC ATATAAATTG ACTGAGGAGC     2300
CGCAACCTTT AGCTCCTACC ATCTTCCTCC TACTGTCTGG GAGTTAAAAA    2350
TGTCATCTGA TGTTCTATTG CAGAAACATC ATTAAATATA ACCCAACAGT    2400
AGGAAGTTGA ATATATCAGC CAACAAATTA CTATGATAGT AAGTCCTGTG    2450
TATTCATTCG CATGTTCCTT GAAAAAAATG AATCCTCTAG CTCTCAGTGG    2500
```

FIGURE 12C

| | | | | | |
|---|---|---|---|---|---|
| AAAGTTTAAA | ACTAGAAACA | TCTGGAGCCC | TAGACAATAT | TTTAGTGTGG | 2550 |
| CGGTAGTCTC | CTGGCTTTGG | GCTCCAGGGA | AAATTCACTC | TTGCCCAAGC | 2600 |
| AGATAAGCCC | AGATGACTAG | AAGCAATTTC | CATTAGGAAG | TGGCAAGAAC | 2650 |
| ATTTGAAGAA | GTAACTTCAT | ATCTATTTAT | CTATATACCT | ATAGTATTTA | 2700 |
| TATACTTGTA | GACATATAGA | TGTATAAAAT | GAAAGCCCAT | AGCCAGCCCC | 2750 |
| ACTCAGTCAA | CAATTCTCAA | AAGAGCAATA | TGAAGCAGTC | ATTTGGTGGG | 2800 |
| GTTCGTATGC | AAGAAAATAA | AAAAACGTCA | TGAATTCCAT | ATGAATACCA | 2850 |
| CGCTAAAGTA | ATGCAAAACA | ATGTGCTGCC | TCAGTGTGTG | TGTGTGTGTG | 2900 |
| TGTGTGTGTG | GTGGGTTCGT | GCATGTATGT | GTGCGTGTGT | GTGTGTGTGT | 2950 |
| GTGTGTGTGT | GTGTGTGTGC | GTGTGTGTTT | GTTTAGGGGT | TTTTATAAAC | 3000 |
| AACTTTTTTT | ATAAAGCACA | CTTTAGTTTA | CAATCTCTCT | TTATAACTGT | 3050 |
| TATAAATTTT | TAAACAACCC | AAAATGCGTT | CCATATAAAG | AAATGGCAAG | 3100 |
| TTATTTAGCT | ATCAAGATTT | TACATGTTTT | CTTTTAACTT | TTTTGTACAA | 3150 |
| TTGCATAGAC | GTGTAAAACC | TGCCATTGTT | AACAAAACAA | TAACAGACTT | 3200 |
| AGAAACTACT | GAAATCTACA | GTATAGTACC | ACTACCCTTC | ACAAAAATAT | 3250 |
| AGATTTTATT | TCTTGTAAAC | TCTTACTGTC | TAATCCTCTT | TGTTGTACGA | 3300 |
| ATATTATAAA | AACCATGCGG | GAATCAGGAG | TTGTAAAACA | TTTATTCTGC | 3350 |
| TCCTTCTTCA | TCTGTCATGA | CTGAAACTAA | GGACTCCATC | GCTCTGCCCA | 3400 |
| AATCATCTGC | CATGTGGAAA | AGGCTTCCTA | CATTGTGTCC | TCTCTCATTG | 3450 |
| GCTTTCCGGG | GGCATTTCTT | CCTCTTGAAC | TAGGGAAGGA | GTTGTTGAGT | 3500 |
| TGCTCCATCA | CTTCTTCTAA | CCCTGTGCTT | GTGTCCTGGG | GAGGACTCAG | 3550 |
| AAGATCTTCC | TCACCCATAG | ATTCTGAAGT | TTGACTGCCA | ACCACTCGGA | 3600 |
| GCAGCATAGG | CTGACTGCTA | TCTGACCTCT | GCAGAGAGGT | GGAAGGAGAG | 3650 |
| GACACCGTGG | TGCCATTCAC | CTTAGCTTCA | GCCTGGGGCT | GCTCCAGGAG | 3700 |
| CTGTCTCAGT | CTATGTAACT | GAGACTCCAG | CTGTTTATTG | TGGTCTTCCA | 3750 |

FIGURE 12D

```
GGATTTGCAT CCTGGCTTCC AGGCGTCCTT TGTGTTGGCG CAGTAGCTTA    3800
GCCTCAGCAA TGAGCTCAGC ATCCCTGGGA CTCTGAGGAG AGGTGGGCAT    3850
CATCTCAGGA GGAGATGGCA GTGGAGACAG GCCTTTATGC TCATGCTGCT    3900
GCTTCAGGCG ATCATATTCT GCTTGCAGAT TCCTGTTTTC TTCCTCAAGA    3950
TCTGCTAGGA TTCTCTCTAG CTCCCCTCTT TCCTCACTCT CTAAGGAAAT    4000
CAAGATCTGG GCAGGACTAC GAGGCTGGCT CAGGGGGGAG TCCTGGTTCA    4050
AACTTTGGCA GTAATGCTGG ATTAACAAAT GTTCATCATC TATGCTCTCA    4100
TTAGGAGAGA TGCTATCATT TAGATAAGAT CCATTGCTGT TTTCCATTTC    4150
TGCTAGCCTG CTAGCATAAT GTTCAATGCG TGAATGAGTA TCATCGTGTG    4200
AAAGCTGGGG GGACGAGGCA GGCGCAGAAT CTACTGGCCA GAAGTTGATC    4250
AGAGTAACGG GAGTTTCCAT GTTGTCCCCC TCTAACACAG TCTGCACTGG    4300
CAGGTAGCCC ATTCGGGGAT GCTTCGCAAA ATACCTTTTG GTTCGAAATT    4350
TGTTTTTTAG TACCTTGGCG AAGTCGCGAA CATCTTCTCC GGATGTAGTC    4400
GGAGTGCAAT ACTCTACCAT GGGGTAGTGC ATTTTATGGC CCTTTGCAAC    4450
TCGGCCAGAA AAAAAGCAAC TTTGGCAGAT GTCATAATTA AAATGCTTTA    4500
GGCTTCTGTA CCTGAATCCA ATGATTGGAC ACTCCTTACA GATGTTACAC    4550
TTGGCTTGAT GCTTGGCAGT TTCAGCAGCA GCCACTCTGT GCAAGACGGG    4600
CAGCCACACC ATAGACTGGG GTTCCAGGCG CATCCAGTCA AGGAAGAGAG    4650
CAGCTTCAAT CTCAGGTTTA TTATTGGCAA ATTGGAAGCA GCTCCTGACA    4700
CTCGGCTCAA TGTTACTGCC CCCAAGGAA GCAACTTCAC CCAACTGTCT    4750
TGGGATTTGA ATAGAATCAT GCAGAAGAAG ACCCAGCCTA CGCTGGTCAC    4800
AAAAGCCAGT TGAACTTGCC ACTTGCTTGA AAAGGTATCT GTACTTGTCT    4850
TCCAAGTGTG CTTTACACAG AGAAATGATG CCAGTTTTAA AAGACAGGAC    4900
ACGGATCCTC CCTGTTCGTC CCGTATCATA AACATTGAGA AGCCAGTTGA    4950
GACACATATC CACACAGAGA GGGACATTGA CCAGATTGTT GTGCTCTTGC    5000
TCCAGACGAT CATAAATTGT AGTCAAACAG TTAATTATCT GCAGGATATC    5050
```

FIGURE 12E

| | | | | |
|---|---|---|---|---|
| CATGGGCTGG | TCATTTTGCT | TGAGGTTGTG | CTGGTCCAGG | GCATCACATG | 5100
| CAGCTGACAG | GCTCAAGAGA | TCCAAGCAAA | GGGCCTTCTG | GAGCCTTCTG | 5150
| AGCTTCATGG | CAGTCCTATA | CGCGGAGAAC | CTGACATTAT | TCAGGTCAGC | 5200
| TAAAGACTGG | TAGAGCTCTG | TCATTTTGGG | GTGGTCCCAA | CAAGTGGTTT | 5250
| GGGTCTCGTG | GTTGATATAG | TAGGGCACTT | TGTTTGGTGA | GATGGCTCTC | 5300
| TCCCAGGGAC | CCTGAACTGA | AGTGGAAAGG | AAGTGCTGGG | ATGCAGGACC | 5350
| AAAGTCCCTG | TGGGCTTCAT | GCAGCTGTCT | GACACGGTCC | TCCACAGCCA | 5400
| CCTGTAGAAG | CCTCCATCTG | GTATTCAGAT | CTTCCAAAGT | GCTGAGGTTA | 5450
| TAAGGTGAGA | GCTGAATGCC | CAGTGTGGTC | AGCTGATGTG | CAAGGTCATT | 5500
| GACACGATTG | ACATTCTCTT | TAAGAGGTGC | AATTTCTCCC | CGAAGTGCCT | 5550
| TGACTTTTTC | AAGGTGATCT | TGCAGAGAGT | CAATGAGGAG | ATCCCCCACT | 5600
| GGCTGCCAGG | ATCCCTTGAT | CACCTCAGCT | TGGCGCAACT | TGAGGTCCAG | 5650
| TTCATCGGCA | GCTTCCTGAA | GTTCCTGGAG | TCTTTCAAGA | GCTTCATCTA | 5700
| TTTTTCTCTG | CCAATCAGCT | GAGCGCAGGT | TCAATTTGTC | CCATTCAGCG | 5750
| TTGACCTCTT | CAGCCTGCTT | TCGTAGGAGC | CGAGTGACAT | TCTGAGCTCT | 5800
| TTCTTCAGGA | GGCAGTTCTC | TGGGCTCCTG | GTAGAGTTTC | TCTAGTCCTT | 5850
| CCAAAGGCTG | CTCTGTCAGA | AATATTCTCA | CAGTCTCCAG | AGTACTCATG | 5900
| ATTACAGGTT | CTTTAGTTTT | CAATTCCCTC | TTGAAGGCCC | TATGTATATC | 5950
| ATTCTGCTTC | TGAACTGCTG | GGAAATCACC | ACCGATGGGT | GCCTGACGGC | 6000
| TCAGTTCATC | ATCTTTCAGC | TGTAGCCAAA | CAAGAAGTTC | CTGAAGAGAA | 6050
| AGATGCAAAC | GCTTCCACTG | GTCAGAACTT | GCTTCCAAAT | GGGACCTAAT | 6100
| GTTGAGAGAC | TTTTTCTGAA | GTTCACTCCA | CTTGAAATTC | ATGTTATCCA | 6150
| AACGTCTTTG | TAACAGGGGT | GCTTCATCCG | AACCTTCCAG | GGATCTCAGG | 6200
| ATTTTTTGGC | CATTTTCATC | AAGATTGTGA | TAGATATCTG | TGTGAGTTTC | 6250
| AATTTCTCCT | TGGAGATCTT | GCCATGGTTT | CATCAGCTCT | CTGACTCCCC | 6300
| TGGAGTCTTC | TAGGAGCTTC | TCCTTACGGG | AAGCGTCCTG | TAGGACATTG | 6350

FIGURE 12F

| | | | | | |
|---|---|---|---|---|---|
| GCAGTTGTTT | CTGCTTCCGT | AATCCAGGAA | AGAAACTTCT | CCAGGTCCAG | 6400 |
| AGGGAACTGC | TGCAGTAATC | TATGAGTTTC | TTCCAAAGCA | GCCTCTTGCT | 6450 |
| CACTTACTCT | TTTATGAATG | TTTCCCCAAG | AAGTATTGAT | ATTCTCTGTT | 6500 |
| ATCATGTGTA | CTTTTCTGGT | ATCATCAGCA | GAATAGTCCC | GAAGAAGTTT | 6550 |
| CAGTGCCAAA | TCATTTGCCA | CGTCTACACT | TATCTGCCGT | TGACGGAGGT | 6600 |
| CTTTGGCCAA | CTGCTTGGTT | TCTGTGATCT | TCTTTTGGAT | TGCATCTACT | 6650 |
| GTGTGAGGAC | CTTCTTTCCA | TGAGTCAAGC | TTGCCTCTGA | CCTGTCCTAT | 6700 |
| GACCTGTTCG | GCTTCTTCCT | TAGCTTCCAG | CCATTGTGTT | GAATCCTTTA | 6750 |
| ACATTTCATT | CAACTGTTGT | CTCCTGTTCT | GCAGCTGTTC | TTGAACCTCA | 6800 |
| TCCCACTGAA | TCTGAATTCT | TTCAATTCGA | TCAGTAATGA | TTGTTCTAGC | 6850 |
| TTCTTGATTG | CTGGTTTTGT | TTTTCAAATT | CTGGGCAGCA | GTAATGAGTT | 6900 |
| CTTCCAATTG | GGGGCGTCTC | TGTTCCAAAT | CTTGCAGTGT | TGCCTTCTGT | 6950 |
| TTGATGATCA | TTTCATTGAT | GTCTTCCAGA | TCACCCACCA | TCACTCTCTG | 7000 |
| TGATTTTATA | ACTCGATCAA | GCAGAGACAG | CCAGTCTGTA | AGTTCTGTCC | 7050 |
| AAGCTCGGTT | GAAGTCTGCC | AGTGCAGGTA | CCTCCAACAG | CAAAGAAGAT | 7100 |
| GGCATTTCTA | GTTTGGAGAT | GACAGTTTCC | TTAGTAACCA | CAGATTGTGT | 7150 |
| CACTAGAGTA | ACAGTCTGAC | TGGCAGAGGC | TCCAGTAGTG | CTCAGTCCAG | 7200 |
| GGGCACGGTC | AGGCTGCTTT | GTCCTCAGCT | CCCGAAGTAA | ATGGTTTACA | 7250 |
| GCCTCCCACT | CAGACCTCAG | ATCTTCTAAC | TTCCTCTTCA | CTGGCTGAGT | 7300 |
| GCTTGGTTTT | TCCTTATACA | AATGCTGCCC | TTTCGACAAA | AGCCTTTCCA | 7350 |
| CATCCGCTTG | TTTACCGTGA | ACTGTTACTT | CAATCTCCTT | TATGTCAAAC | 7400 |
| GGTCCTGCCT | GACTTGGTTG | GTTATAAATT | TCCAACTGGT | TTCTAATAGG | 7450 |
| AGAGACCCAC | AGAAGCAGGT | GATCCAGCTG | CTCTTCAAGC | TGCCTAAAAT | 7500 |
| CTTTTAAGTG | AACCTCAAGC | TCTCCTTGTT | TCTCAGGTAA | AGCTCTGGAG | 7550 |
| ACCTTTATCC | ACTGGAGATT | TGTCTGTTTG | AGCTTCTTTT | CAAGTTTATC | 7600 |

FIGURE 12G

| | | | | | |
|---|---|---|---|---|---|
| TTGCTCTTCT | GGCCTTATGG | GAGCACTTAC | AAGTACTGCT | CCTCCTGTTT | 7650 |
| CATTTAATTG | TTTTAGAATT | CCCTGGCGCA | GGGGCAACTC | TTCTGCCAGT | 7700 |
| AACTTGACTT | GTTCAAGTTG | TTCTTTTAGC | TGCTGCTCAT | CTCCAAGTGG | 7750 |
| AGTAATAGCA | ATGTTATCTG | CTTCTTCCAG | CCACAAAACA | AATTCATTTA | 7800 |
| AATCTCTTTG | AAATTCTGAC | AAGACATTCT | TTTGTTCTTC | AATCCTCTTT | 7850 |
| CTCCTTTCTG | CCAGCTCTTT | GCAGATGTCG | TGCCACCGCA | GACTCAAGCT | 7900 |
| TCCTAATTTT | TCTTGTAGAA | TATTGACATC | TGTTTTGAA | GACTGTTGAA | 7950 |
| TTATTTCTTC | CCCAGTTGCA | TTCAGTGTTC | TGACAACAGC | TTGACGCTGC | 8000 |
| CCAATGCCAT | CCTGGAGTTC | CTTAAGATAC | CATTTGTATT | TAGCATGTTC | 8050 |
| CCAGTTTTCA | GGATTTTGTG | TCTTTTTGAA | AAACTGTTCA | ACTTCATTCA | 8100 |
| GCCATTGATT | AAATACCTTC | ATATCATAAT | GAAAGTGTCG | CCATTTTTCA | 8150 |
| ACTGATCTGT | CGAATCGCCC | TTGTCGTTCC | TTGTACATTC | TATGAAGTTT | 8200 |
| TTCCCCCTGG | AAATCCATCT | GTGCCACGGC | TTCCTGTACT | TTCACCTTTT | 8250 |
| CCATGGAGGT | GGCACTTTGC | AAGGCTGCTG | TCTTCTTCTT | GTGAATAATA | 8300 |
| TCAATCCGAC | CTGAGATTTG | TTGCAAATTG | TCTTTTATAT | TCTTAAGAGA | 8350 |
| CTCCTCTTGC | TTAAAAGAT | CTTCAAAATC | TTTAGCACAG | AGTTCAGGAG | 8400 |
| TATTTAGAAG | ATGATCAACT | TCTGAAAGAG | CTTGTAAGAT | ATGACTGATC | 8450 |
| TCGGTCAAAT | AAGTAGAAGG | CACATAAGAA | ACATCCAAAG | GCATATCTTC | 8500 |
| AGTCGTCACT | ACCATAGTTT | CTTCATGGAG | AGTGTGAATT | TGTGCAAAGT | 8550 |
| TGAGTCTTCG | AAACTGAGCA | AAATTGCTCT | CAATTTGCCG | CCAGCGCTTG | 8600 |
| CTGAGCTGGA | TCTGAGTTGG | CTCCACTGCC | ATTGCGGCCC | CATTCTCAGA | 8650 |
| CAAGCCCTCA | GCTTGCCTGC | GCACTGCATT | CAGCTCCTCT | TTCTTCTTCT | 8700 |
| GCAATTCACG | ATCAATTTCC | TTTAATTTTC | TTTCATCTCT | GGGTTCAGGT | 8750 |
| AGGCTGGCTA | ATTTTTTTTC | AATTTCATCC | AAGCATTTCA | GGAGATCATC | 8800 |
| AGCCTGCCTC | TTGTACTGAT | ACCACTGGTG | AGAAATTTCT | AGGGCCTTTT | 8850 |

FIGURE 12H

```
TTCTTCTTTG AGACCTCAAA TCCTTGAGAG CATTATGTTT TGTCTGTAAC     8900
AGCTGCTGTT TTATCTTTAT TTCCTCTCGC TTTCTCTCAT CTGTGATTCT     8950
TTGTTGTAAG TTGTCTCCTC TTTGCAACAA TTCATTTACA GTACCCTCAT     9000
TGTCTTCACT CATATCTTTA TTGAAGTCTT CCTCTTTCAG ATTCACCCCC     9050
TGCTGAATTT CAGCCTCCAG TGGTTCAAGC AATTTTTGTA TATCTGAGTT     9100
AAACTGCTCC AATTCCTTCA AAGGAATGGA GGCCTTTCCA GTCTTAATTC     9150
TGTGAGAAAT AGCTGCAAAT CGACGGTTGA GCTCAGAGAT TGGGGCTCT      9200
ACTACTTTCC TGCAGTGGTC ACCGCGGTTT GCCATCAATT TGCTGCTTG      9250
GTCACGTGTG GAGTCCACCT TTGGGCGCAT GTCATTCATT TCAGCCTTTA     9300
AACGCTTAAG AATGTCTTCC TTTTGTTGTG GTTTCTTCTT TTCAGACTCA     9350
TCTAAAAGTT CATCTGCATG AATGATCCAC TTTGTGATTT GTTCTATGTT     9400
CTGATCAAAG GTTTCCATGT GTTTCTGGTA TTCCAACAAA AGATTTAGCC     9450
ATTCTTCTAC TCTGGAGGTG ACAGCTATCC AGTTACTGTT CAGAAGACTC     9500
AGTTTATCTT CTACCAAGGT TTCTTTCTTG CCCAACACCA TTTTCAAAGA     9550
CTCTCCTAAT TCTGTAACAC TCTTCAAGTG AGCCTTCTGT TTCTCAATCT     9600
CTTTTTGAGT AGCCTTTCCC CAGGCAACTT CAGAATCCAA ATTACTTGGC     9650
ATTCCTTCAA CTGCTGATCT CTTCGTCAAT TCTGTATCTG TTGCTGCCAG     9700
CCATTCTGTT AAGACATTCA TTTCCTTTCT CATCTTACGG GACAACTTCA     9750
AGCATTTCTC CAACTGTTGC TTTCTCTCTG TTACCTTCGC ACCCAACTCA     9800
TTGTAATGCA ATTTCAAAGC TGTTACTCGT TCATCAAGCT CTTTGGGATT     9850
TTCTGTCTGC TTTTTCTGTA CAATTTGACG TCCGGTTTTA ATCACCATTT     9900
CCACTTCAGA CTTGACTTCA CTCAGGCTTT TATACAAGTT CACACAATGA     9950
CTTAGTTGTG ACTGAATTAC TTCCTGTTCA ACACTCTTGG TTTCCAATGC    10000
AGGCAAATGC ATCTTGACTT CATCTAAAAT CATCTTACTT TCCTCTAGAC    10050
GTTGTTCAAA ATTGGCTGGT TTTTGGAATA ATCGAAATTT CATGGAGACA    10100
TCTTGTAATT TTTTCTGTGC AACATCAATT TGTGAAAGAA CCCTTTGGTT    10150
```

FIGURE 12I

```
GGCATCCTTC CCCTGGTTAT GTTTCTTCAT TTCTTCTAAA CTTATCTCAT    10200
GACTTGTCAA ATCTGATTGG ATTTTCTGGG CTTCCTGAGG CATTTGAGCT    10250
GCATCCACCT TGTCAGTGAT ATAAGCTGCC AACTGCTTGT CAATGAATTC    10300
AAGCGACTCC TGAATTAAGT GCAAGGACTT TTCAATTTCC TGGGCAGACT    10350
GGATACTCTG TTCAAGCAAC TTTTGTTTCC TCACAGCCTC TTCATGTAGT    10400
TCCCTCCAAC GAGAATTAAA CGTCTCAAGC TCCTCATTGA TCAGTTCATC    10450
CATGACTCCT CCATCTGTAA GAGTCTGTGC CAATAGACGA ATCTGATTTG    10500
GGTTCTCCTC TGAATGATGC ATCAGATTTT CAAGAGATTC TAGCACTTCA    10550
GTGATTTCCT CAGGTCCTGC AGGAACATTT TCCATGGTTT TAAGTTTCAA    10600
TTCTACTTCA TTGAGCCACT TGTTTGCTTT CTCTAAATAT GACAATAACT    10650
CATGCCAACA TGCCCAAACT TCTTCCAAAG TTTTGCATTT TCCATTCAGC    10700
CTGGTGCACA GCCATTGGTA GTTGGTGGTC AGAGTTTCAA GTTCCTTTTT    10750
TAAGGCCTCT TGTGCTGAGG GTGGAGCGTG AGCTATTACA CTATTTACAG    10800
TCTCAGTAAG GAGTTTCACT TTAGTTTCTT TTTGTAGTGC CTCTTCTTTA    10850
GCTCTCTTCA TTTCTTCAAC AGCAGTCTGT AATTCATCTG GAGTTTTATA    10900
TTCAAAATCT CTCTCTAGAT ATTCTTCTTC AGCTTGTGTC ATCCACTCAT    10950
GCATCTCTGA TAGATCTTTT TGGAGGCTTA CGGTTTTATC CAAACCTGCC    11000
TTTAAGGCTT CCTTTCTGGT GTAGACCTGG CGGCATATGT GATCCCACTG    11050
AGTGTTAAGC TCTCTAAGTT CTGTCTCCAG TCTGGATGCA AACTCAAGTT    11100
CAGCTTCACT CTTTATCTTC TGCCCACCTT CATTAACACT ATTTAAACTG    11150
GGCTGAATTG TTTGAATATC ACCAACTAAA AGTCTGCATT GTTTGAGCTG    11200
TTTTTTCAGG ATTTCAGCAT CCCCCAGGGC AGGCCATTCC TCTTTCAGGA    11250
AAACATCAAC TTCAGCCATC CATTTCTGTA AGGTTTTTAT GTGATTCTGA    11300
AATTTTCGAA GTTTATTCAT ATGTTCTTCT AGCTTTTGGC AGCTTTCCAC    11350
CAACTGGGAG GAAAGTTTCT TCCAGTGCCC CTCAATCTCT TCAAATTCTG    11400
```

FIGURE 12J

| | | | | | |
|---|---|---|---|---|---|
| ACAGATATTT | CTGGCATATT | TCTGAAGGTG | CTTTCTTGGC | CATCTCCTTC | 11450 |
| ACAGTGTCAC | TCAGATAGTT | GAAGCCATTT | TGTTGCTCTT | TCAAAGAACT | 11500 |
| TTGCAGAGCC | TGTAATTTCC | CGAGTCTCTC | CTCCATTATT | TCATATTCAG | 11550 |
| TAACACTAAG | ATAAGGTACA | GAGAGTTTGC | TTTCTGACTG | CTGGATCCAC | 11600 |
| GTCCTGATGC | TACTCATTGT | CTCCTGATAG | CGCATTGGTG | GTAAAGTGTC | 11650 |
| AAAAATTGTC | TGTAGCTCTT | TCTCTTTGGC | CCTCACACCA | TCAAAGATGT | 11700 |
| GGTTAAAATG | ATTAGTAAAG | GCCACAAAGT | CTGCATCCAG | AAACATTGGC | 11750 |
| CCCTGTCCCT | TTTCTTTCAG | TTGTAGACTC | TGAATTTTTA | ATTGCTCAAT | 11800 |
| TTGAGGCTGA | AGAGCTGACA | ATCTGTTGAC | TTCATCCTTA | CAAATTTTTA | 11850 |
| ACTGGCTTTT | AATTGCTGTT | GGCTCTGATA | GGGTGGTAGA | CTGGGTTTTC | 11900 |
| AACAAGTTTT | CGGCAGTAGT | TGTCATCTGT | TCCAATTGTT | GTAGCTGATT | 11950 |
| ATAAAAGGTA | ATGATGTTGG | TTTGATACTC | TAGCCAGTTA | ACTCTCTCAC | 12000 |
| TCAGCAATTG | GCAGAATTCT | GTCCACCGGC | TGTTCAGTTG | TTCTGAAGCT | 12050 |
| TGTCTGATAC | TTTCAGCATT | AACACCCTCA | TTTGCCATCT | GTTCCACCAG | 12100 |
| GGCCTGAGCT | GATCTGCTGG | CATCTTGCAG | TTTTCTGAAC | TTCTCTGCTT | 12150 |
| TTTCTCGTGC | TATGGCATTG | ACTTTTTCTT | GCAAGTCTGA | GATGTTGCCT | 12200 |
| TCTTTTCGAT | AGACTGCAAA | TTCAGAACTC | TGTAATACAG | CTTCTGAACG | 12250 |
| AGTAATCCAA | CTGTGAAGTT | CAGTTATATC | GACATCCAAC | CTTTTCCTGA | 12300 |
| GTTCAGAATC | CACAGTTATC | TGCCTCTTCT | TTTGAGGAGG | TGGTGGTGGA | 12350 |
| AGTTCCTCTT | GGGCATGTTT | TACCATGATT | TGTTCCCTTG | TGGTCACCAT | 12400 |
| AGTTACCGTT | TCCATTACAG | TTGTCTGTGT | TAGGGATGGT | TGAGTGGTGG | 12450 |
| TGACAGCCTG | TGAAATTTGT | GCTGAACTCT | TTTCAAGTTT | TTGGGTTAAA | 12500 |
| TTGTCCCAAC | GTTGTGCAAA | GTTTTCCATC | CAGATTTCCA | TCTTTTGAGT | 12550 |
| CACTGACTTA | TTTTTCAGTG | CCGAAAGTAG | ATCTTGATTG | AGTGAACTTA | 12600 |
| GTTTTTCCAT | GGTTGGCTTT | TTCTTTTCTA | GATCTATTTT | TAAAGTAGAT | 12650 |

FIGURE 12K

| | | | | | |
|---|---|---|---|---|---|
| ATTTTGTGAA | GACTTGACAT | CATTTCATTT | TGATCTTTAA | AGCCACTTGT | 12700 |
| CTGAATGTTC | TTCATTGCAT | CTTCTTTTTC | TGAAAGCCAT | GTACTAAAAA | 12750 |
| GGCACTGTTC | TTCAGTAAAA | TGCTGCCATT | TTAGAAGAAT | ATCTTGTAAA | 12800 |
| ACAATCCAGC | GGTCTTCAGT | CCATCTGCAG | ATATTTGCCC | ATCGATCTCC | 12850 |
| CAGTACCTTA | AGTTGTTCTT | CCAAAGCAGC | TGTTGCATGA | TCACCGCTGG | 12900 |
| ATTCATCAAC | CACTACTACC | ATGTGAGTGA | GCGAGTTGAC | CCTGACCTGC | 12950 |
| TCCTGTTCTA | GATCTTCTTG | AAGCACCTTA | TGTTGTTGTA | CTTGGCATTT | 13000 |
| TAGATCTTCA | AGATCAGGTC | CAAAGGGCTC | TTCCTCCATT | TTCTTAGTTC | 13050 |
| TCTCTTCAGT | TTTTGTTAAC | CAGTCATCTA | GTTCTTTTAA | TTTCTGATTC | 13100 |
| TGGAGATCCA | TTAGAACTTT | GTGTAATTTG | CTTTGTTTTT | CCATGCTAGC | 13150 |
| TACCCTGAGA | CATTCCCATC | TTGAATTTAG | GAGATTCATT | TGTTCTTGCA | 13200 |
| CTTCAGCTTC | TTCATCTTCT | GATAATTTCC | CTTTTCCAAC | TAGTTGACTT | 13250 |
| CCTAACTGTA | GAACATTACC | AACAAGTCCT | TGATGAGATG | TCAGATCCAT | 13300 |
| CATGAATCCC | TCATGAGCAT | GAAACTGTTC | TTTCACTTCT | TCAACATCAT | 13350 |
| TTGAAATCTC | TCCTTGTGCT | CGCAATGTAT | CCTCGGCAGA | AAGAAGCCAT | 13400 |
| GAAAGTACTT | CTTCTAAAGC | AGTTTGGTAA | CTATCCAGAT | TTACTTCCGT | 13450 |
| CTCCATCAAT | GAACTGTCAA | GTGACTTGTC | TCTGGGAGCT | TCCAAATGCT | 13500 |
| GTGAAGGATA | GGGGCTCTGT | GTGGAATCAG | AGGTGGCAAC | ATAAGCAGCC | 13550 |
| TGTGTGAAGG | CATAACTCTT | GAATCGAGGC | TTAGGAGATG | AAGAAGTTTG | 13600 |
| TTCATAGCCC | TGTGCTAGAC | TGACTGTGAT | CTGTTGAGAG | TAATGCATCT | 13650 |
| GGTGATGTAA | TTGAAAATGT | TCTTCTCTAG | TTACTTTTGA | AGATGTCCTG | 13700 |
| GGCAACATTT | CCACTTCTTG | AATGGCTTCA | ATGCTCACTT | GTTGTGGCAA | 13750 |
| AACTTGAAAG | AGTGATGTGA | TGTACATTAA | GATGGACTTC | TTGTCTGGAT | 13800 |
| AAGTGGTAGC | AACATCTTCA | GGATCAAGAA | GTTTTTCTAT | GCCTAACTGG | 13850 |
| CATTTTGCAA | TGTTGAAGGC | ATGTTCCAGT | CTTTGGGTGG | CTGAGTGCTG | 13900 |

FIGURE 12L

| | | | | | |
|---|---|---|---|---|---|
| TGAAACCACA | CTATTCCAAT | CAAACAGGTC | GGGCCTGTGA | CTATGGATAA | 13950 |
| GAGCATTCAA | AGCCAACCCG | TCGGACCAGC | TAGAGGTGAA | GTTGATGACG | 14000 |
| TTAACCTGTG | GATAATTACG | TGTTGACTGT | CGAACCCAGC | TCAGAAGAAT | 14050 |
| CTTTTCACTG | TTGGTTTGCT | GCAATCCAGC | CATGATAGTT | TTCATCACAT | 14100 |
| TTTTGACCTG | CCAGTGGAGG | ATTATATTCC | AAATCAAACC | AAGAGTGAGT | 14150 |
| TTATGATTTC | CATCCACTAT | GTCAGTGCTT | CCTATATTCA | CTAAATCAAC | 14200 |
| ATTATTTTTC | TGTAAGACCC | GCAGTGCCTT | GTTGACATTG | TTCAGGGCAT | 14250 |
| GAACTCTTGT | AGATCCCTTT | TCTTTTGGCA | GTTTTGCCC | TGTAAGGCCT | 14300 |
| TCCAAGAGGT | CTAGGAGGCG | TTTTCCATCC | TGCAGGTCAC | TGAAGAGGTT | 14350 |
| GTCTATGTGT | TGCTTTCCAA | ACTTAGAAAA | TTGTGCATTT | ATCCATTTTG | 14400 |
| TGAATGTTTT | CTTTTGAACA | TCTTCTCTTT | CATAACAGTC | CTCTACTTCT | 14450 |
| TCCCACCAAA | GCATTTGGAA | GAAAAGTAT | ATATCAAGGC | AGGGATAAAA | 14500 |
| ATCTTGGTAA | AAGTTTCTCC | CAGTTTTATT | GCTCCAGGAG | GCTTAGGTAC | 14550 |
| GATGAGAAGC | CAATAAACTT | CAGCAGCCTT | GACAAAAAAA | AAAAAAAAA | 14600 |
| TAGCACTTCA | AGTCTTCCTA | TTCGTTTTTT | CTATAAAGCT | ATTGCCTTCA | 14650 |
| AGAGCGGAAT | TCCTGCAGCC | CGGGGGATCC | ACTAGTTCTA | GAGCGGCCGC | 14700 |
| GGGTACAATT | CCGCAGCTTT | TAGAGCAGAA | GTAACACTTC | CGTACAGGCC | 14750 |
| TAGAAGTAAA | GGCAACATCC | ACTGAGGAGC | AGTTCTTTGA | TTTGCACCAC | 14800 |
| CACCGGATCC | GGGACCTGAA | ATAAAAGACA | AAAAGACTAA | ACTTACCAGT | 14850 |
| TAACTTTCTG | GTTTTTCAGT | TCCTCGAGTA | CCGGATCCTC | TAGAGTCCGG | 14900 |
| AGGCTGGATC | GGTCCCGGTG | TCTTCTATGG | AGGTCAAAAC | AGCGTGGATG | 14950 |
| GCGTCTCCAG | GCGATCTGAC | GGTTCACTAA | ACGAGCTCTG | CTTATATAGA | 15000 |
| CCTCCCACCG | TACACGCCTA | CCGCCCATTT | GCGTCAATGG | GGCGGAGTTG | 15050 |
| TTACGACATT | TTGGAAAGTC | CCGTTGATTT | TGGTGCCAAA | ACAAACTCCC | 15100 |
| ATTGACGTCA | ATGGGGTGGA | GACTTGGAAA | TCCCCGTGAG | TCAAACCGCT | 15150 |
| ATCCACGCCC | ATTGATGTAC | TGCCAAAACC | GCATCACCAT | GGTAATAGCG | 15200 |

FIGURE 12M

| | | | | |
|---|---|---|---|---|
| ATGACTAATA | CGTAGATGTA | CTGCCAAGTA | GGAAAGTCCC | ATAAGGTCAT | 15250
| GTACTGGGCA | TAATGCCAGG | CGGGCCATTT | ACCGTCATTG | ACGTCAATAG | 15300
| GGGGCGTACT | TGGCATATGA | TACACTTGAT | GTACTGCCAA | GTGGGCAGTT | 15350
| TACCGTAAAT | ACTCCACCCA | TTGACGTCAA | TGGAAAGTCC | CTATTGGCGT | 15400
| TACTATGGGA | ACATACGTCA | TTATTGACGT | CAATGGGCGG | GGTCGTTGG | 15450
| GCGGTCAGCC | AGGCGGGCCA | TTTACCGTAA | GTTATGTAAC | GACCTGCAGG | 15500
| TCGACTCTAG | AGGATCTCCC | TAGACAAATA | TTACGCGCTA | TGAGTAACAC | 15550
| AAAATTATTC | AGATTTCACT | TCCTCTTATT | CAGTTTTCCC | GCGAAAATGG | 15600
| CCAAATCTTA | CTCGGTTACG | CCCAAATTTA | CTACAACATC | CGCCTAAAAC | 15650
| CGCGCGAAAA | TTGTCACTTC | CTGTGTACAC | CGGCGCACAC | CAAAAACGTC | 15700
| ACTTTTGCCA | CATCCGTCGC | TTACATGTGT | TCCGCCACAC | TTGCAACATC | 15750
| ACACTTCCGC | CACACTACTA | CGTCACCCGC | CCCGTTCCCA | CGCCCCGCGC | 15800
| CACGTCACAA | ACTCCACCCC | CTCATTATCA | TATTGGCTTC | AATCCAAAAT | 15850
| AAGGTATATT | ATTGATGATG | CTAGCGGGGC | CCTATATATG | GATCCAATTG | 15900
| CAATGATCAT | CATGACAGAT | CTGCGCGCGA | TCGATATCAG | CGCTTTAAAT | 15950
| TTGCGCATGC | TAGCTATAGT | TCTAGAGGTA | CCGGTTGTTA | ACGTTAGCCG | 16000
| GCTACGTATA | CTCCGGAATA | TTAATAGGCC | TAGGATGCAT | ATGGCGGCCG | 16050
| GCCGCCTGCA | GCTGGCGCCA | TCGATACGCG | TACGTCGCGA | CCGCGGACAT | 16100
| GTACAGAGCT | CGAGAAGTAC | TAGTGGCCAC | GTGGGCCGTG | CACCTTAAGC | 16150
| TTGGCACTGG | CCGTCGTTTT | ACAACGTCGT | GACTGGGAAA | ACCCTGGCGT | 16200
| TACCCAACTT | AATCGCCTTG | CAGCACATCC | CCCTTTCGCC | AGCTGGCGTA | 16250
| ATAGCGAAGA | GGCCCGCACC | GATCGCCCTT | CCCAACAGTT | GCGCAGCCTG | 16300
| AATGGCGAAT | GGCGCCTGAT | GCGGTATTTT | CTCCTTACGC | ATCTGTGCGG | 16350
| TATTTCACAC | CGCATACGTC | AAAGCAACCA | TAGTACGCGC | CCTGTAGCGG | 16400
| CGCATTAAGC | GCGGCGGGTG | TGGTGGTTAC | GCGCAGCGTG | ACCGCTACAC | 16450

FIGURE 12N

| | | | | | |
|---|---|---|---|---|---|
| TTGCCAGCGC | CCTAGCGCCC | GCTCCTTTCG | CTTTCTTCCC | TTCCTTTCTC | 16500 |
| GCCACGTTCG | CCGGCTTTCC | CCGTCAAGCT | CTAAATCGGG | GGCTCCCTTT | 16550 |
| AGGGTTCCGA | TTTAGTGCTT | TACGGCACCT | CGACCCCAAA | AAACTTGATT | 16600 |
| TGGGTGATGG | TTCACGTAGT | GGGCCATCGC | CCTGATAGAC | GGTTTTCGC | 16650 |
| CCTTTGACGT | TGGAGTCCAC | GTTCTTTAAT | AGTGGACTCT | TGTTCCAAAC | 16700 |
| TGGAACAACA | CTCAACCCTA | TCTCGGGCTA | TTCTTTTGAT | TTATAAGGGA | 16750 |
| TTTTGCCGAT | TTCGGCCTAT | TGGTTAAAAA | ATGAGCTGAT | TTAACAAAAA | 16800 |
| TTTAACGCGA | ATTTTAACAA | AATATTAACG | TTTACAATTT | TATGGTGCAC | 16850 |
| TCTCAGTACA | ATCTGCTCTG | ATGCCGCATA | GTTAAGCCAG | CCCCGACACC | 16900 |
| CGCCAACACC | CGCTGACGCG | CCCTGACGGG | CTTGTCTGCT | CCCGGCATCC | 16950 |
| GCTTACAGAC | AAGCTGTGAC | CGTCTCCGGG | AGCTGCATGT | GTCAGAGGTT | 17000 |
| TTCACCGTCA | TCACCGAAAC | GCGCGAGACG | AAAGGGCCTC | GTGATACGCC | 17050 |
| TATTTTTATA | GGTTAATGTC | ATGATAATAA | TGGTTTCTTA | GACGTCAGGT | 17100 |
| GGCACTTTTC | GGGGAAATGT | GCGCGGAACC | CCTATTTGTT | TATTTTTCTA | 17150 |
| AATACATTCA | AATATGTATC | CGCTCATGAG | ACAATAACCC | TGATAAATGC | 17200 |
| TTCAATAATA | TTGAAAAAGG | AAGAGTATGA | GTATTCAACA | TTTCCGTGTC | 17250 |
| GCCCTTATTC | CCTTTTTTGC | GGCATTTTGC | CTTCCTGTTT | TTGCTCACCC | 17300 |
| AGAAACGCTG | GTGAAAGTAA | AAGATGCTGA | AGATCAGTTG | GGTGCACGAG | 17350 |
| TGGGTTACAT | CGAACTGGAT | CTCAACAGCG | GTAAGATCCT | TGAGAGTTTT | 17400 |
| CGCCCCGAAG | AACGTTTTCC | AATGATGAGC | ACTTTTAAAG | TTCTGCTATG | 17450 |
| TGGCGCGGTA | TTATCCCGTA | TTGACGCCGG | GCAAGAGCAA | CTCGGTCGCC | 17500 |
| GCATACACTA | TTCTCAGAAT | GACTTGGTTG | AGTACTCACC | AGTCACAGAA | 17550 |
| AAGCATCTTA | CGGATGGCAT | GACAGTAAGA | GAATTATGCA | GTGCTGCCAT | 17600 |
| AACCATGAGT | GATAACACTG | CGGCCAACTT | ACTTCTGACA | ACGATCGGAG | 17650 |
| GACCGAAGGA | GCTAACCGCT | TTTTTGCACA | ACATGGGGGA | TCATGTAACT | 17700 |

FIGURE 120

```
CGCCTTGATC GTTGGGAACC GGAGCTGAAT GAAGCCATAC CAAACGACGA    17750
GCGTGACACC ACGATGCCTG TAGCAATGGC AACAACGTTG CGCAAACTAT    17800
TAACTGGCGA ACTACTTACT CTAGCTTCCC GGCAACAATT AATAGACTGG    17850
ATGGAGGCGG ATAAAGTTGC AGGACCACTT CTGCGCTCGG CCCTTCCGGC    17900
TGGCTGGTTT ATTGCTGATA AATCTGGAGC CGGTGAGCGT GGGTCTCGCG    17950
GTATCATTGC AGCACTGGGG CCAGATGGTA AGCCCTCCCG TATCGTAGTT    18000
ATCTACACGA CGGGGAGTCA GGCAACTATG GATGAACGAA ATAGACAGAT    18050
CGCTGAGATA GGTGCCTCAC TGATTAAGCA TTGGTAACTG TCAGACCAAG    18100
TTTACTCATA TATACTTTAG ATTGATTTAA AACTTCATTT TTAATTTAAA    18150
AGGATCTAGG TGAAGATCCT TTTTGATAAT CTCATGACCA AAATCCCTTA    18200
ACGTGAGTTT TCGTTCCACT GAGCGTCAGA CCCCGTAGAA AAGATCAAAG    18250
GATCTTCTTG AGATCCTTTT TTTCTGCGCG TAATCTGCTG CTTGCAAACA    18300
AAAAACCAC CGCTACCAGC GGTGGTTTGT TTGCCGGATC AAGAGCTACC     18350
AACTCTTTTT CCGAAGGTAA CTGGCTTCAG CAGAGCGCAG ATACCAAATA    18400
CTGTTCTTCT AGTGTAGCCG TAGTTAGGCC ACCACTTCAA GAACTCTGTA    18450
GCACCGCCTA CATACCTCGC TCTGCTAATC CTGTTACCAG TGGCTGCTGC    18500
CAGTGGCGAT AAGTCGTGTC TTACCGGGTT GGACTCAAGA CGATAGTTAC    18550
CGGATAAGGC GCAGCGGTCG GGCTGAACGG GGGGTTCGTG CACACAGCCC    18600
AGCTTGGAGC GAACGACCTA CACCGAACTG AGATACCTAC AGCGTGAGCT    18650
ATGAGAAAGC GCCACGCTTC CCGAAGGGAG AAAGGCGGAC AGGTATCCGG    18700
TAAGCGGCAG GGTCGGAACA GGAGAGCGCA CGAGGGAGCT TCCAGGGGGA    18750
AACGCCTGGT ATCTTTATAG TCCTGTCGGG TTTCGCCACC TCTGACTTGA    18800
GCGTCGATTT TTGTGATGCT CGTCAGGGGG CGGAGCCTA TGGAAAAACG     18850
CCAGCAACGC GGCCTTTTTA CGGTTCCTGG CCTTTTGCTG GCCTTTTGCT    18900
CACATGTTCT TTCCTGCGTT ATCCCCTGAT TCTGTGGATA ACCGTATTAC    18950
```

FIGURE 12P

| | | | | | |
|---|---|---|---|---|---|
| CGCCTTTGAG | TGAGCTGATA | CCGCTCGCCG | CAGCCGAACG | ACCGAGCGCA | 19000 |
| GCGAGTCAGT | GAGCGAGGAA | GCGGAAGAGC | GCCCAATACG | CAAACCGCCT | 19050 |
| CTCCCCGCGC | GTTGGCCGAT | TCATTAATGC | AGCTGGCACG | ACAGGTTTCC | 19100 |
| CGACTGGAAA | GCGGGCAGTG | AGCGCAACGC | AATTAATGTG | AGTTAGCTCA | 19150 |
| CTCATTAGGC | ACCCCAGGCT | TTACACTTTA | TGCTTCCGGC | TCGTATGTTG | 19200 |
| TGTGGAATTG | TGAGCGGATA | ACAATTTCAC | ACAGGAAACA | GCTATGACCA | 19250 |
| TGATTACGAA | TTCGAATGGC | CATGGGACGT | CGACCTGAGG | TAATTATAAC | 19300 |
| CCGGGCC | | | | | 19307 |

ADENOVIRUS AND METHODS OF USE THEREOF

CROSS-REFERENCE TO RELATED APPLICATIONS

This is a national phase filing, pursuant to 35 USC 371, of PCT/US95/14017, filed Oct. 27, 1995, which is a C-I-P of U.S. patent application 08/331,381, filed Oct. 28, 1994.

This invention was supported by the National Institute of Health Grant No. P30 DK 47757. The United States government has rights in this invention.

FIELD OF THE INVENTION

The present invention relates to the field of vectors useful in somatic gene therapy and the production thereof.

BACKGROUND OF THE INVENTION

Human gene therapy is an approach to treating human disease that is based on the modification of gene expression in cells of the patient. It has become apparent over the last decade that the single most outstanding barrier to the success of gene therapy as a strategy for treating inherited diseases, cancer, and other genetic dysfunctions is the development of useful gene transfer vehicles. Eukaryotic viruses have been employed as vehicles for somatic gene therapy. Among the viral vectors that have been cited frequently in gene therapy research are adenoviruses.

Adenoviruses are eukaryotic DNA viruses that can be modified to efficiently deliver a therapeutic or reporter transgene to a variety of cell types. Recombinant adenoviruses types 2 and 5 (Ad2 and Ad5, respectively), which cause respiratory disease in humans, are currently being developed for gene therapy. Both Ad2 and Ad5 belong to a subclass of adenovirus that are not associated with human malignancies. Recombinant adenoviruses are capable of providing extremely high levels of transgene delivery to virtually all cell types, regardless of the mitotic state. High titers ($10^{13}$ plaque forming units/ml) of recombinant virus can be easily generated in 293 cells (the adenovirus equivalent to retrovirus packaging cell lines) and cryo-stored for extended periods without appreciable losses. The efficacy of this system in delivering a therapeutic transgene in vivo that complements a genetic imbalance has been demonstrated in animal models of various disorders [Y. Watanabe, *Atherosclerosis*, 36:261–268 (1986); K. Tanzawa et al, *FEBS Letters*, 118(1):81–84 (1980); J.L. Golasten et al, *New Engl. J. Med.*, 309(11983):288–296 (1983); S. Ishibashi et al, *J. Clin. Invest.*, 92:883–893 (1993); and S. Ishibashi et al, *J. Clin. Invest.*, 93:1885–1893 (1994)]. Indeed, a recombinant replication defective adenovirus encoding a cDNA for the cystic fibrosis transmembrane regulator (CFTR) has been approved for use in at least two human CF clinical trials [see, e.g., J. Wilson, *Nature*, 365:691–692 (Oct. 21, 1993)]. Further support of the safety of recombinant adenoviruses for gene therapy is the extensive experience of live adenovirus vaccines in human populations.

Human adenoviruses are comprised of a linear, approximately 36 kb double-stranded DNA genome, which is divided into 100 map units (m.u.), each of which is 360 bp in length. The DNA contains short inverted terminal repeats (ITR) at each end of the genome that are required for viral DNA replication. The gene products are organized into early (E1 through E4) and late (L1 through L5) regions, based on expression before or after the initiation of viral DNA synthesis [see, e.g., Horwitz, *Virology*, 2d edit., ed. B. N. Fields, Raven Press, Ltd. New York (1990)].

The first-generation recombinant, replication-deficient adenoviruses which have been developed for gene therapy contain deletions of the entire E1a and part of the E1b regions. This replication-defective virus is grown on an adenovirus-transformed, complementation human embryonic kidney cell line containing a functional adenovirus E1a gene which provides a transacting E1a protein, the 293 cell [ATCC CRL1573]. E1-deleted viruses are capable of replicating and producing infectious virus in the 293 cells, which provide E1a and E1b region gene products in trans. The resulting virus is capable of infecting many cell types and can express the introduced gene (providing it carries its own promoter), but cannot replicate in a cell that does not carry the E1 region DNA unless the cell is infected at a very high multiplicity of infection.

However, in vivo studies revealed transgene expression in these E1 deleted vectors was transient and invariably associated with the development of severe inflammation at the site of vector targeting [S. Ishibashi et al, *J. Clin. Invest.*, 93:1885–1893 (1994); J. M. Wilson et al, *Proc. Natl. Acad. Sci., USA*, 85:4421–4424 (1988); J. M. Wilson et al, *Clin. Bio.*, 3:21–26 (1991); M. Grossman et al, *Som. Cell. and Mol. Gen.*, 17:601–607 (1991)]. One explanation that has been proposed to explain this finding is that first generation recombinant adenoviruses, despite the deletion of E1 genes, express low levels of other viral proteins. This could be due to basal expression from the unstimulated viral promoters or transactivation by cellular factors. Expression of viral proteins leads to cellular immune responses to the genetically modified cells, resulting in their destruction and replacement with nontransgene containing cells.

There yet remains a need in the art for the development of additional adenovirus vector constructs for gene therapy.

SUMMARY OF THE INVENTION

In one aspect, the invention provides the components of a novel recombinant adenovirus production system. One component is a shuttle plasmid, pAdΔ, that comprises adenovirus cis-elements necessary for replication and virion encapsidation and is deleted of all viral genes. This vector carries a selected transgene under the control of a selected promoter and other conventional vector/plasmid regulatory components. The other component is a helper adenovirus, which alone or with a packaging cell line, supplies sufficient gene sequences necessary for a productive viral infection. In a preferred embodiment, the helper virus has been altered to contain modifications to the native gene sequences which direct efficient packaging, so as to substantially disable or "cripple" the packaging function of the helper virus or its ability to replicate.

In another aspect, the present invention provides a unique recombinant adenovirus, an AdΔ virus, produced by use of the components above. This recombinant virus comprises an adenovirus capsid, adenovirus cis-elements necessary for replication and virion encapsidation, but is deleted of all viral genes (i.e., all viral open reading frames). This virus particle carries a selected transgene under the control of a selected promoter and other conventional vector regulatory components. This AdΔ recombinant virus is characterized by high titer transgene delivery to a host cell and the ability to stably integrate the transgene into the host cell chromosome. In one embodiment, the virus carries as its transgene a reporter gene. Another embodiment of the recombinant virus contains a therapeutic transgene.

In another aspect, the invention provides a method for producing the above-described recombinant AdΔ virus by co-transfecting a cell line (either a packaging cell line or a non-packaging cell line) with a shuttle vector or plasmid and a helper adenovirus as described above, wherein the transfected cell generates the AdΔ virus. The AdΔ virus is subsequently isolated and purified therefrom.

In yet a further aspect, the invention provides a method for delivering a selected gene to a host cell for expression in that cell by administering an effective amount of a recombinant AdΔ virus containing a therapeutic transgene to a patient to treat or correct a genetically associated disorder or disease.

Other aspects and advantages of the present invention are described further in the following detailed description of the preferred embodiments thereof.

BRIEF DESCRIPTION OF THE FIGURES

FIG. 1A is a schematic representation of the organization of the major functional elements that define the 5' terminus from Ad5 including an inverted terminal repeat (ITR) and a packaging/enhancer domain. The TATA box of the E1 promoter (black box) and E1A transcriptional start site (arrow) are also shown.

FIG. 1B is an expanded schematic of the packaging/enhancer region of FIG. 1A, indicating the five packaging (PAC) domains (A-repeats), I through V. The arrows indicate the location of PCR primers referenced in FIGS. 9A and 9B below.

FIGS. 3A to 3F [SEQ ID NO: 1] report the top DNA strand of the double-stranded plasmid pAdΔ.CMVLacZ. The complementary sequence may be readily obtained by one of skill in the art. The sequence includes the following components: 3' Ad ITR (nucleotides 607–28 of SEQ ID NO: 1); the 5' Ad ITR (nucleotides 5496–5144 of SEQ ID NO: 1); CMV promoter/enhancer (nucleotides 5117–4524 of SEQ ID NO: 1); SD/SA sequence (nucleotides 4507–4376 of SEQ ID NO: 1); LacZ gene (nucleotides 4320–845 of SEQ ID NO: 1); and a poly A sequence (nucleotides 837–639 of SEQ ID NO: 1).

FIGS. 5A to 5F [SEQ ID NO: 2] report the top DNA strand of the double-stranded vector pAdΔc.CMVLacZ. The complementary sequence may be readily obtained by one of skill in the art. The sequence includes the following components: 5' Ad ITR (nucleotides 600–958 of SEQ ID NO: 2); CMV promoter/enhancer (nucleotides 969–1563 of SEQ ID NO: 2); SD/SA sequence (nucleotides 1579–1711); LacZ gene (nucleotides 1762–5236 of SEQ ID NO: 2); poly A sequence (nucleotides 5245–5443 of SEQ ID NO: 2); and 3' Ad ITR (nucleotides 16–596 of SEQ ID NO: 2).

FIGS. 7A to 7H [SEQ ID NO: 3] report the top DNA strand of the double-stranded plasmid pAdΔ.CBCFTR. The complementary sequence may be readily obtained by one of skill in the art. The sequence includes the following components: 5' Ad ITR (nucleotides 9611–9254 of SEQ ID NO: 3); chimeric CMV enhancer/β actin promoter (nucleotides 9241–8684 of SEQ ID NO: 3); CFTR gene (nucleotides 8622–4065 of SEQ ID NO: 3); poly A sequence (nucleotides 3887–3684 of SEQ ID NO: 3); and 3' Ad ITR (nucleotides 3652–3073 of SEQ ID NO: 3). The remaining plasmid backbone is obtained from pSL1180 (Pharmacia).

FIG. 12A–12P provides the continuous DNA sequence of pAdΔ.CMVmDys [SEQ ID NO:10].

DETAILED DESCRIPTION OF THE INVENTION

Figure 2A:
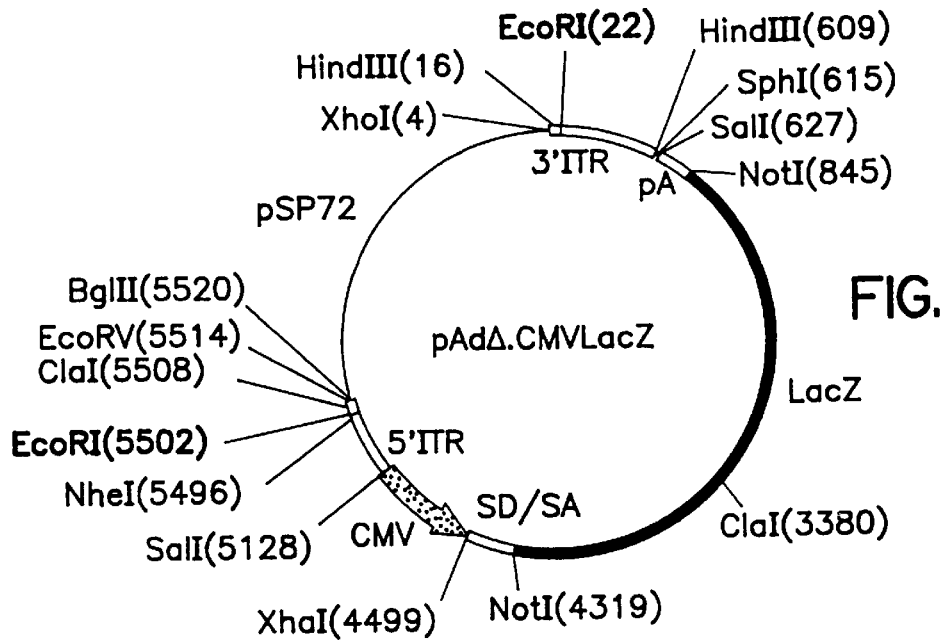
FIG. 2A is a schematic of shuttle vector pAdΔ.CMVLacZ containing 5' ITR from Ad5, followed by a CMV promoter/enhancer, a LacZ gene, a 3' ITR from Ad5, and remaining plasmid sequence from plasmid pSP72 backbone. Restriction endonuclease enzymes are represented by conventional designations in the plasmid constructs.

The present invention provides a unique recombinant adenovirus capable of delivering transgenes to target cells, as well as the components for production of the unique virus and methods for the use of the virus to treat a variety of genetic disorders.

The AdΔ virus of this invention is a viral particle containing only the adenovirus cis-elements necessary for replication and virion encapsidation (i.e., ITRs and packaging sequences), but otherwise deleted of all adenovirus genes (i.e., all viral open reading frames). This virus carries a selected transgene under the control of a selected promoter and other conventional regulatory components, such as a poly A signal. The AdΔ virus is characterized by improved persistence of the vector DNA in the host cells, reduced antigenicity/immunogenicity, and hence, improved performance as a delivery vehicle. An additional advantage of this invention is that the AdΔ virus permits the packaging of very large transgenes, such as a full-length dystrophin cDNA for the treatment of the progressive wasting of muscle tissue characteristic of Duchenne Muscular Dystrophy (DMD).

This novel recombinant virus is produced by use of an adenovirus-based vector production system containing two components: 1) a shuttle vector that comprises adenovirus cis-elements necessary for replication and virion encapsidation and is deleted of all viral genes, which vector carries a reporter or therapeutic minigene and 2) a helper adenovirus which, alone or with a packaging cell line, is capable of providing all of the viral gene products necessary for a productive viral infection when co-transfected with the shuttle vector. Preferably, the helper virus is modified so that it does not package itself efficiently. In this setting, it is desirably used in combination with a packaging cell line that stably expresses adenovirus genes. The methods of producing this viral vector from these components include both a novel means of packaging of an adenoviral/transgene containing vector into a virus, and a novel method for the subsequent separation of the helper virus from the newly formed recombinant virus.

I. The Shuttle Vector

The shuttle vector, referred to as pAdΔ, is composed of adenovirus sequences, and transgene sequences, including vector regulatory control sequences.

A. The Adenovirus Sequences

The adenovirus nucleic acid sequences of the shuttle vector provide the minimum adenovirus sequences which enable a viral particle to be produced with the assistance of a helper virus. These sequences assist in delivery of a recombinant transgene genome to a target cell by the resulting recombinant virus.

The DNA sequences of a number of adenovirus types are available from Genbank, including type Ad5 [Genbank Accession No. M73260]. The adenovirus sequences may be obtained from any known adenovirus serotype, such as serotypes 2, 3, 4, 7, 12 and 40, and further including any of the presently identified 41 human types [see, e.g., Horwitz, cited above]. Similarly adenoviruses known to infect other animals may also be employed in the vector constructs of this invention. The selection of the adenovirus type is not anticipated to limit the following invention. A variety of adenovirus strains are available from the American Type Culture Collection, Rockville, Md., or available by request from a variety of commercial and institutional sources. In the following exemplary embodiment an adenovirus, type 5 (Ad5) is used for convenience.

However, it is desirable to obtain a variety of pAdΔ shuttle vectors based on different human adenovirus serotypes. It is anticipated that a library of such plasmids and the resulting AdΔ viral vectors would be useful in a therapeutic regimen to evade cellular, and possibly humoral, immunity, and lengthen the duration of transgene expression, as well as improve the success of repeat therapeutic treatments. Additionally the use of various serotypes is believed to produce recombinant viruses with different tissue targeting specificities. The absence of adenoviral genes in the AdΔ viral vector is anticipated to reduce or eliminate adverse CTL response which normally causes destruction of recombinant adenoviruses deleted of only the E1 gene.

Specifically, the adenovirus nucleic acid sequences employed in the pAdΔ shuttle vector of this invention are adenovirus genomic sequences from which all viral genes are deleted. More specifically, the adenovirus sequences employed are the cis-acting 5' and 3' inverted terminal repeat (ITR) sequences of an adenovirus (which function as origins of replication) and the native 5' packaging/enhancer domain, that contains sequences necessary for packaging linear Ad genomes and enhancer elements for the E1 promoter. These sequences are the sequences necessary for replication and virion encapsidation. See, e.g., P. Hearing et al, J. Virol., 61(8):2555–2558 (1987); M. Grable and P. Hearing, J. Virol., 64(5): 2047–2056 (1990); and M. Grable and P. Hearing, J. Virol., 66(2):723–731 (1992).

According to this invention, the entire adenovirus 5' sequence containing the 5' ITR and packaging/enhancer region can be employed as the 5' adenovirus sequence in the pAdΔ shuttle vector. This left terminal (5') sequence of the Ad5 genome useful in this invention spans bp 1 to about 360 of the conventional adenovirus genome, also referred to as map units 0–1 of the viral genome. This sequence is provided herein as nucleotides 5496–5144 of SEQ ID NO: 1, nucleotides 600–958 of SEQ ID NO: 2; and nucleotides 9611–9254 of SEQ ID NO: 3, and generally is from about 353 to about 360 nucleotides in length. This sequence includes the 5' ITR (bp 1–103 of the adenovirus genome), and the packaging/enhancer domain (bp 194–358 of the adenovirus genome). See, FIGS. 1A, 3, 5, and 7.

Preferably, this native adenovirus 5' region is employed in the shuttle vector in unmodified form. However, some modifications including deletions, substitutions and additions to this sequence which do not adversely effect its biological function may be acceptable. See, e.g., WO 93/24641, published Dec. 9, 1993. The ability to modify these ITR sequences is within the ability of one of skill in the art. See, e.g., texts such as Sambrook et al, "Molecular Cloning. A Laboratory Manual.", 2d edit., Cold Spring Harbor Laboratory, Cold Spring Harbor, N.Y. (1989).

The 3' adenovirus sequences of the shuttle vector include the right terminal (3') ITR sequence of the adenoviral genome spanning about bp 35,353—end of the adenovirus genome, or map units ⁻98.4–100. This sequence is provided herein as nucleotides 607–28 of SEQ ID NO: 1, nucleotides 16–596 of SEQ ID NO: 2; and nucleotides 3652–3073 of SEQ ID NO: 3, and generally is about 580 nucleotides in length. This entire sequence is desirably employed as the 3' sequence of an pAdΔ shuttle vector. Preferably, the native adenovirus 3' region is employed in the shuttle vector in unmodified form. However, some modifications to this sequence which do not adversely effect its biological function may be acceptable.

An exemplary pAdΔ shuttle vector of this invention, described below and in FIG. 2A, contains only those adenovirus sequences required for packaging adenoviral genomic DNA into a preformed capsid head. The pAdΔ vector contains Ad5 sequences encoding the 5' terminal and 3' terminal sequences (identified in the description of FIG. 3), as well as the transgene sequences described below.

From the foregoing information, it is expected that one of skill in the art may employ other equivalent adenovirus sequences for use in the AdΔ vectors of this invention. These sequences may include other adenovirus strains, or the above mentioned cis-acting sequences with minor modifications.

B. The Transgene

The transgene sequence of the vector and recombinant virus is a nucleic acid sequence or reverse transcript thereof, heterologous to the adenovirus sequence, which encodes a polypeptide or protein of interest. The transgene is operatively linked to regulatory components in a manner which permits transgene transcription.

The composition of the transgene sequence will depend upon the use to which the resulting virus will be put. For example, one type of transgene sequence includes a reporter sequence, which upon expression produces a detectable signal. Such reporter sequences include without limitation an E. coli beta-galactosidase (LacZ) CDNA, a human placental alkaline phosphatase gene and a green fluorescent protein gene. These sequences, when associated with regulatory elements which drive their expression, provide signals detectable by conventional means, e.g., ultraviolet wavelength absorbance, visible color change, etc.

Another type of transgene sequence includes a therapeutic gene which expresses a desired gene product in a host cell. These therapeutic nucleic acid sequences typically encode products for administration and expression in a patient in vivo or ex vivo to replace or correct an inherited or non-inherited genetic defect or treat an epigenetic disorder or disease. Such therapeutic genes which are desirable for the performance of gene therapy include, without limitation, a normal cystic fibrosis transmembrane regulator (CFTR) gene (see FIG. 7), a low density lipoprotein (LDL) receptor gene [T. Yamamoto et al, *Cell*, 39:27–28 (November, 1984)], a DMD cDNA sequence [partial sequences available from GenBank, Accession Nos. M36673, M36671, [A. P. Monaco et al, *Nature*, 323:646–650 (1986)] and L06900, [Roberts et al, *Hum. Mutat.*, 2:293–299 (1993)]] (Genbank), and a number of genes which may be readily selected by one of skill in the art. The selection of the transgene is not considered to be a limitation of this invention, as such selection is within the knowledge of the art-skilled.

C. Regulatory Elements

In addition to the major elements identified above for the pAdΔ shuttle vector, i.e., the adenovirus sequences and the transgene, the vector also includes conventional regulatory elements necessary to drive expression of the transgene in a cell transfected with the pAdΔ vector. Thus the vector contains a selected promoter which is linked to the transgene and located, with the transgene, between the adenovirus sequences of the vector.

Selection of the promoter is a routine matter and is not a limitation of the pAdΔ vector itself. Useful promoters may be constitutive promoters or regulated (inducible) promoters, which will enable control of the amount of the transgene to be expressed. For example, a desirable promoter is that of the cytomegalovirus immediate early promoter/enhancer [see, e.g., Boshart et al, *Cell*, 41:521–530 (1985)]. This promoter is found at nucleotides 5117–4524 of SEQ ID NO: 1 and nucleotides 969–1563 of SEQ ID NO: 2. Another promoter is the CMV enhancer/chicken β-actin promoter (nucleotides 9241–8684 of SEQ ID NO: 3). Another desirable promoter includes, without limitation, the Rous sarcoma virus LTR promoter/enhancer. Still other promoter/enhancer sequences may be selected by one of skill in the art.

The shuttle vectors will also desirably contain nucleic acid sequences heterologous to the adenovirus sequences including sequences providing signals required for efficient polyadenylation of the transcript and introns with functional splice donor and acceptor sites (SD/SA). A common poly-A sequence which is employed in the exemplary vectors of this invention is that derived from the papovavirus SV-40 [see, e.g., nucleotides 837–639 of SEQ ID NO: 1; 5245–5443 of SEQ ID NO: 2; and 3887–3684 of SEQ ID NO: 3]. The poly-A sequence generally is inserted in the vector following the transgene sequences and before the 3' adenovirus sequences. A common intron sequence is also derived from SV-40, and is referred to as the SV-40 T intron sequence [see, e.g., nucleotides 4507–4376 of SEQ ID NO: 1 and 1579–1711 of SEQ ID NO: 2]. A pAdΔ shuttle vector of the present invention may also contain such an intron, desirably located between the promoter/enhancer sequence and the transgene. Selection of these and other common vector elements are conventional and many such sequences are available [see, e.g., Sambrook et al, and references cited therein]. Examples of such regulatory sequences for the above are provided in the plasmid sequences of FIGS. 3, 5 and 7.

The combination of the transgene, promoter/enhancer, the other regulatory vector elements are referred to as a "minigene" for ease of reference herein. The minigene is preferably flanked by the 5' and 3' cis-acting adenovirus sequences described above. Such a minigene may have a size in the range of several hundred base pairs up to about 30 kb due to the absence of adenovirus early and late gene sequences in the vector. Thus, this AdΔ vector system permits a great deal of latitude in the selection of the various components of the minigene, particularly the selected transgene, with regard to size. Provided with the teachings of this invention, the design of such a minigene can be made by resort to conventional techniques.

II. The Helper Virus

Because of the limited amount of adenovirus sequence present in the AdΔ shuttle vector, a helper adenovirus of this invention must, alone or in concert with a packaging cell line, provide sufficient adenovirus gene sequences necessary for a productive viral infection. Helper viruses useful in this invention thus contain selected adenovirus gene sequences, and optionally a second reporter minigene.

Normally, the production of a recombinant adenovirus which utilizes helper adenovirus containing a full complement of adenoviral genes results in recombinant virus contaminated by excess production of the helper virus. Thus, extensive purification of the viral vector from the contaminating helper virus is required. However, the present invention provides a way to facilitate purification and reduce contamination by crippling the helper virus.

One preferred embodiment of a helper virus of this invention thus contains three components (A) modifications or deletions of the native adenoviral gene sequences which direct efficient packaging, so as to substantially disable or "cripple" the packaging function of the helper virus or its ability to replicate, (B) selected adenovirus genes and (C) an optional reporter minigene. These "crippled" helper viruses may also be formed into poly-cation conjugates as described below.

The adenovirus sequences forming the helper virus may be obtained from the sources identified above in the discussion of the shuttle vector. Use of different Ad serotypes as helper viruses enables production of recombinant viruses containing the ΔAd (serotype 5) shuttle vector sequences in a capsid formed by the other serotype adenovirus. These recombinant viruses are desirable in targeting different tissues, or evading an immune response to the ΔAd sequences having a serotype 5 capsid. Use of these different Ad serotype helper viruses may also demonstrate advantages in recombinant virus production, stability and better packaging.

A. The Crippling Modifications

A desirable helper virus used in the production of the adenovirus vector of this invention is modified (or crippled) in its 5' ITR packaging/enhancer domain, identified above. As stated above, the packaging/enhancer region contains sequences necessary for packaging linear adenovirus genomes ("PAC" sequences). More specifically, this sequence contains at least seven distinct yet functionally redundant domains that are required for efficient encapsidation of replicated viral DNA.

Within a stretch of nucleotide sequence from bp 194–358 of the Ad5 genome, five of these so-called A-repeats or PAC sequences are localized (see, FIG. 1B). PAC I is located at bp 241–248 of the adenovirus genome (on the strand complementary to nucleotides 5259–5246 of SEQ ID NO: 1). PAC II is located at bp 262–269 of the adenovirus genome (on the strand complementary to nucleotides 5238–5225 of SEQ ID NO: 1). PAC III is located at bp 304–311 of the adenovirus genome (on the strand complementary to nucleotides 5196–5183 of SEQ ID NO: 1). PAC IV is located at bp 314–321 of the adenovirus (on the strand complementary to nucleotides 5186–5172 of SEQ ID NO: 1). PAC V is located at bp 339–346 of the adenovirus (on the strand complementary to nucleotides 5171–5147 of SEQ ID NO: 1).

Corresponding sequences can be obtained from SEQ ID NO: 2 and 3. PAC I is located at nucleotides 837–851 of SEQ ID NO: 2; and on the strand complementary to nucleotides 9374–9360 of SEQ ID NO: 3. PAC II is located at nucleotides 859–863 of SEQ ID NO: 2; and on the strand complementary to nucleotides 9353–9340 of SEQ ID NO: 3. PAC III is located at nucleotides 901–916 of SEQ ID NO: 2; and on the strand complementary to nucleotides 9311–9298 of SEQ ID NO: 3. PAC IV is located at nucleotides 911–924 of SEQ ID NO: 2; and on the strand complementary to nucleotides 9301–9288 of SEQ ID NO: 3. PAC V is located at nucleotides 936–949 of SEQ ID NO: 2; and on the strand complementary to nucleotides 9276–9263 of SEQ ID NO: 3.

Table 1 below lists these five native Ad5 sequences and a consensus PAC sequence based on the similarities between an eight nucleic acid stretch within the five sequences. The consensus sequence contains two positions at which the nucleic acid may be A or T (A/T). The conventional single letter designations are used for the nucleic acids, as is known to the art.

TABLE 1

| A-Repeat | Adenovirus Genome Base Pair Nos. & Nucleotide sequence | |
|---|---|---|
| I | 241    248<br>TAG TAAATTTG GGC | [SEQ ID NO: 4] |
| II | 262    269<br>AGT AAGATTTG GCC | [SEQ ID NO: 5] |
| III | 304    311<br>AGT GAAATCTG AAT | [SEQ ID NO: 6] |
| IV | 314    321<br>GAA TAATTTTG TGT | [SEQ ID NO: 7] |
| V | 339    346<br>CGT AATATTTG TCT | [SEQ ID NO: 8] |
| Consensus | 5' (A/T)AN(A/T)TTTG 3' | [SEQ ID NO: 9] |

According to this invention, mutations or deletions may be made to one or more of these PAC sequences to generate desirable crippled helper viruses. A deletion analysis of the packaging domain revealed a positive correlation between encapsidation efficiency and the number of packaging A-repeats that were present at the 5' end of the genome. Modifications of this domain may include 5' adenovirus sequences which contain less than all five of the PAC sequences of Table 1. For example, only two PAC sequences may be present in the crippled virus, e.g., PAC I and PAC II, PAC III and PAC IV, and so on. Deletions of selected PAC sequences may involve deletion of contiguous or non-contiguous sequences. For example, PAC II and PAC IV may be deleted, leaving PAC I, III and IV in the 5' sequence. Still an alternative modification may be the replacement of one or more of the native PAC sequences with one or more repeats of the consensus sequence of Table 1. Alternatively, this adenovirus region may be modified by deliberately inserted mutations which disrupt one or more of the native PAC sequences. One of skill in the art may further manipulate the PAC sequences to similarly achieve the effect of reducing the helper virus packaging efficiency to a desired level.

Exemplary helper viruses which involve the manipulation of the PAC sequences described above are disclosed in Example 7 below. Briefly, as described in that example, one helper virus contains in place of the native 5' ITR region (adenovirus genome bp 1–360), a 5' adenovirus sequence spanning adenovirus genome bp 1–269, which contains only the 5' ITR and PAC I and PAC II sequences, and deletes the adenovirus region bp 270–360.

Another PAC sequence modified helper virus contains only the 5' Ad5 sequence of the ITR and PAC I through PAC IV (Ad bp 1–321), deleting PAC V and other sequences in the Ad region bp322–360.

These modified helper viruses are characterized by reduced efficiency of helper virus encapsidation. These helper viruses with the specific modifications of the sequences related to packaging efficiency, provide a packaging efficiency high enough for generating production lots of the helper virus, yet low enough that they permit the achievement of higher yields of AdΔ transducing viral particles according to this invention.

B. The Solected Adenovirus Genes

Helper viruses useful in this invention, whether or not they contain the "crippling" modifications described above, contain selected adenovirus gene sequences depending upon the cell line which is transfected by the helper virus and shuttle vector. A preferred helper virus contains a variety of adenovirus genes in addition to the modified sequences described above.

As one example, if the cell line employed to produce the recombinant virus is not a packaging cell line, the helper virus may be a wild type Ad virus. Thus, the helper virus supplies the necessary adenovirus early genes E1, E2, E4 and all remaining late, intermediate, structural and non-structural genes of the adenovirus genome. This helper virus may be a crippled helper virus by incorporating modifications in its native 5' packaging/enhancer domain.

A desirable helper virus is replication defective and lacks all or a sufficient portion of the adenoviral early immediate early gene E1a (which spans mu 1.3 to 4.5) and delayed early gene E1b (which spans mu 4.6 to 11.2) so as to eliminate their normal biological functions. Such replication deficient viruses may also have crippling modifications in the packaging/enhancer domain. Because of the difficulty surrounding the absolute removal of adenovirus from AdΔ preparations that have been enriched by CsCl buoyant density centrifugation, the use of a replication defective adenovirus helper prevents the introduction of infectious adenovirus for in vivo animal studies. This helper virus is employed with a packaging cell line which supplies the deficient E1 proteins, such as the 293 cell line.

Additionally, all or a portion of the adenovirus delayed early gene E3 (which spans mu 76.6 to 86.2) may be eliminated from the adenovirus sequence which forms a part of the helper viruses useful in this invention, without adversely at ecting the function of the helper virus because this gene product is not necessary for the formation of a functioning virus.

In the presence of other packaging cell lines which are capable of supplying adenoviral proteins in addition to the E1, the helper virus may accordingly be deleted of the genes encoding these adenoviral proteins. Such additionally deleted helper viruses also desirably contain crippling modifications as described above.

C. A Reporter Minigene

It is also desirable for the helper virus to contain a reporter minigene, in which the reporter gene is desirably different from the reporter transgene contained in the shuttle vector. A number of such reporter genes are known, as referred to above. The presence of a reporter gene on the helper virus which is different from the reporter gene on the pAdΔ, allows both the recombinant AdΔ virus and the helper virus to be independently monitored. For example, the expression of recombinant alkaline phosphatase enables residual quantities of contaminating adenovirus to be monitored independent of recombinant LacZ expressed by an pAdΔ shuttle vector or an AdΔ virus.

D. Helper Virus Polycation Conjugates

Still another method for reducing the contamination of helper virus involves the formation of poly-cation helper virus conjugates, which may be associated with a plasmid containing other adenoviral genes, which are not present in the helper virus. The helper viruses described above may be further modified by resort to adenovirus-polylysine conjugate technology. See, e.g., Wu et al, *J. Biol. Chem.*, 264:16985–16987 (1989); and K. J. Fisher and J. M. Wilson, *Biochem. J.*, 299: 49 (Apr. 1, 1994), incorporated herein by reference.

Using this technology, a helper virus containing preferably the late adenoviral genes is modified by the addition of a poly-cation sequence distributed around the capsid of the helper virus. Preferably, the poly-cation is poly-lysine, which attaches around the negatively-charged vector to form an external positive charge. A plasmid is then designed to express those adenoviral genes not present in the helper virus, e.g., the E1, E2 and/or E4 genes. The plasmid associates to the helper virus-conjugate through the charges on the poly-lysine sequence. This modification is also desirably made to a crippled helper virus of this invention. This conjugate (also termed a trans-infection particle) permits additional adenovirus genes to be removed from the helper virus and be present on a plasmid which does not become incorporated into the virus during production of the recombinant viral vector. Thus, the impact of contamination is considerably lessened.

III. Assembly of Shuttle Vector, Helper Virus and Production of Recombinant Virus The material from which the sequences used in the pAdΔ shuttle vector and the helper viruses are derived, as well as the various vector components and sequences employed in the construction of the shuttle vectors, helper viruses, and AdΔ viruses of this invention, are obtained from commercial or academic sources based on previously published and described materials. These materials may also be obtained from an individual patient or generated and selected using standard recombinant molecular cloning techniques known and practiced by those skilled in the art. Any modification of existing nucleic acid sequences forming the vectors and viruses, including sequence deletions, insertions, and other mutations are also generated using standard techniques.

Assembly of the selected DNA sequences of the adenovirus, and the reporter genes or therapeutic genes and other vector elements into the pAdΔ shuttle vector using conventional techniques is described in Example 1 below. Such techniques include conventional cloning techniques of cDNA such as those described in texts [Sambrook et al, cited above], use of overlapping oligonucleotide sequences of the adenovirus genomes, polymerase chain reaction, and any suitable method which provides the desired nucleotide sequence. Standard transfection and co-transfection techniques are employed, e.g., $CaPO_4$ transfection techniques using the HEK 293 cell line. Other conventional methods employed in this invention include homologous recombination of the viral genomes, plaguing of viruses in agar overlay, methods of measuring signal generation, and the like. Assembly of any desired AdΔ vector or helper virus of this invention is within the skill of the art, based on the teachings of this invention.

A. Shuttle Vector

As described in detail in Example 1 below and with resort to FIG. 2A and the DNA sequence of the plasmid reported in FIG. 3, a unique pAdΔ shuttle vector of this invention, pAdΔ.CMVLacZ, is generated. pAdΔ.CMVLacZ contains Ad5 sequences encoding the 5' terminal followed by a CMV promoter/enhancer, a splice donor/splice acceptor sequence, a bacterial beta-galactosidase gene (LacZ), a SV-40 poly A sequence (pA), a 3' ITR from Ad5 and remaining plasmid sequence from plasmid pSP72 (Promega) backbone.

Figure 2B:
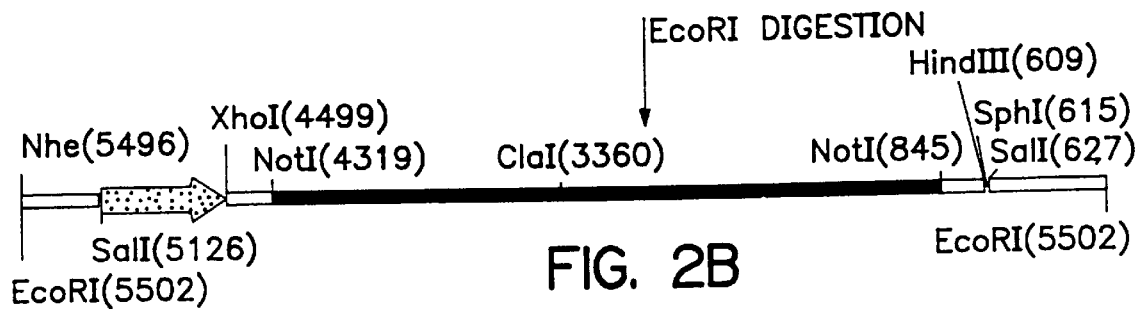
FIG. 2B is a schematic of the shuttle vector digested with EcoRI to release the modified AdΔ genome from the pSP72 plasmid backbone.

To generate the AdΔ genome which is incorporated in the vector, the plasmid pAdΔ.CMVLacZ must be must be digested with EcoRI to release the AdΔ.CMVLacZ genome, freeing the adenovirus ITRs and making them available targets for replication. Thus production of the vector is "restriction-dependent", i.e., requires restriction endonuclease rescue of the replication template. See, FIG. 2B.

Figure 4A:
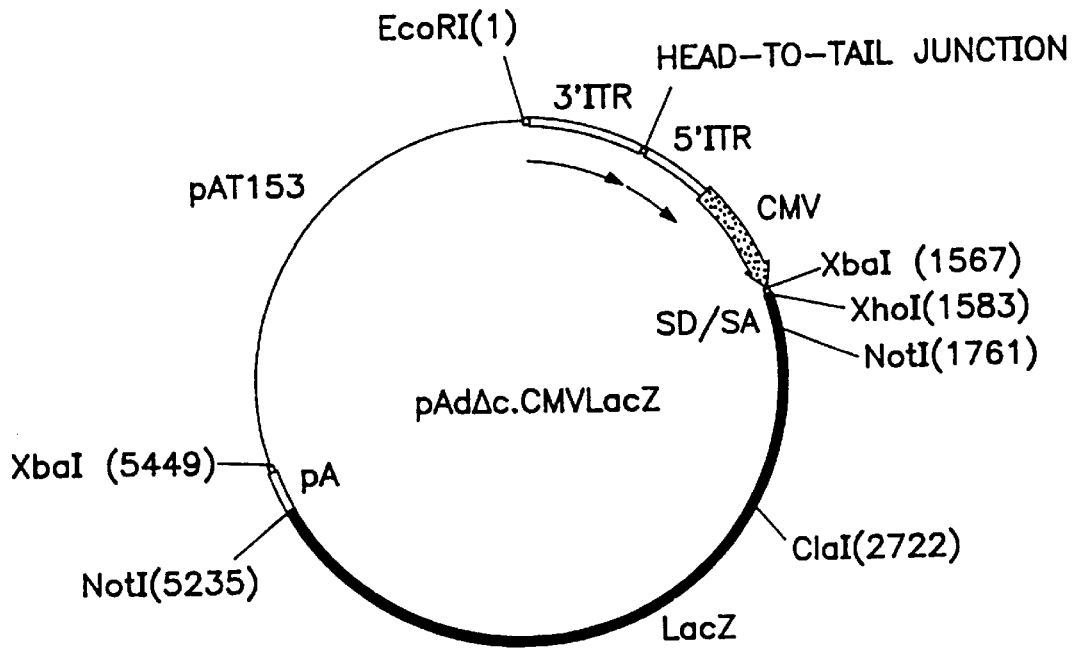
FIG. 4A is a schematic of shuttle vector pAdΔc.CMVLacZ containing an Ad5 5' ITR and 3' ITR positioned head-to-tail, with a CMV enhancer/promoter-LacZ minigene immediately following the 5' ITR, followed by a plasmid pSP72 (Promega) backbone. Restriction endonuclease enzymes are represented by conventional designations in the plasmid constructs.
Figure 4B:
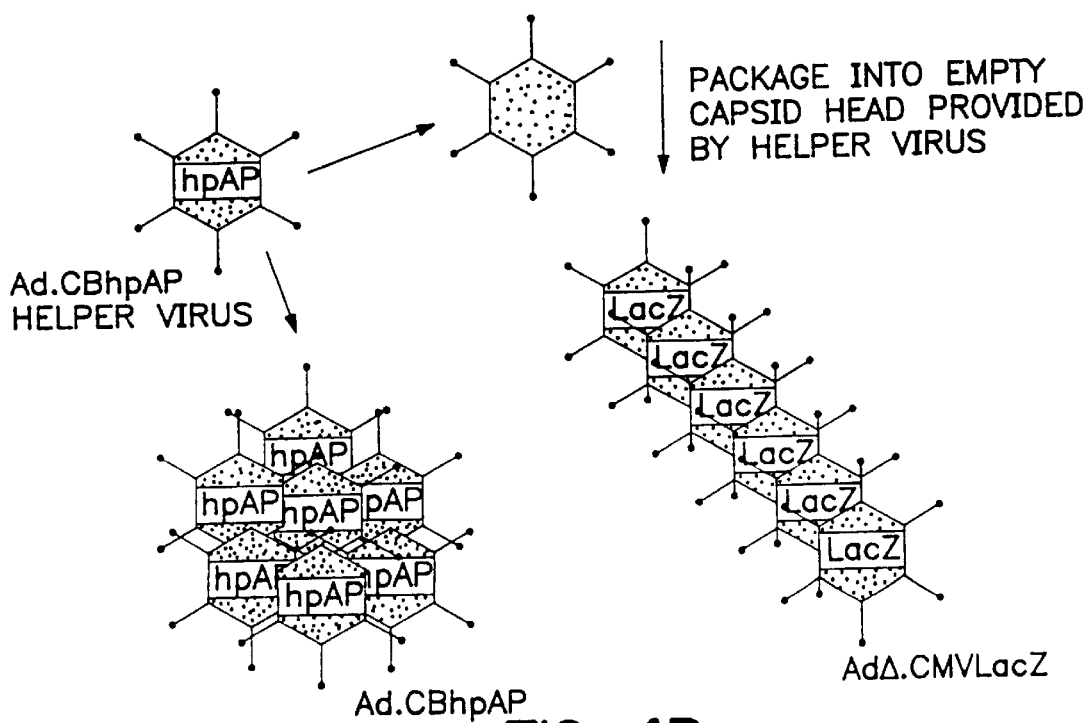
FIG. 4B is a schematic depiction of the function of the vector system of FIG. 4A. In the presence of helper virus Ad.CBhpAP, the circular pADΔc.CMVLacZ shuttle vector sequence is packaged into virion heads, distinguishable from the helper virions by the presence of the LacZ gene.

A second type of pAdΔ plasmid was designed which places the 3' Ad terminal sequence in a head-to-tail arrangement relative to the 5' terminal sequence. As described in Example 1 and FIGS. 4A, and with resort to the DNA sequence of the plasmid reported in FIG. 5, a second unique AdΔ vector sequence of this invention, AdΔc.CMVLacZ, is generated from the shuttle plasmid pAdΔc.CMVLacZ, which contains an Ad5 5' ITR sequence and 3' ITR sequence positioned head-to-tail, followed by a CMV enhancer/promoter, SD/SA sequence, LacZ gene and pA sequence in a plasmid pSP72 (Promega) backbone. As described in Example 1B, this "restriction-independent" plasmid permits the AdΔ genome to be replicated and rescued from the plasmid backbone without including an endonuclease treatment (see, FIG. 4B).

B. Helper Virus

As described in detail in Example 2, an exemplary conventional E1 deleted adenovirus helper virus is virus Ad.CBhpAP, which contains a 5' adenovirus sequence from mu 0–1, a reporter minigene containing human placenta alkaline phosphatase (hpAP) under the transcriptional control of the chicken β-actin promoter, followed by a poly-A sequence from SV40, followed by adenovirus sequences from 9.2 to 78.4 and 86 to 100. This helper contained deletions from mu 1.0 to 9.2 and 78.4 to 86, which eliminate substantially the E1 region and the E3 region of the virus. This virus may be desirably crippled according to this invention by modifications to its packaging enhancer domain.

Exemplary crippled helper viruses of this invention are described using the techniques described in Example 7 and contain the modified 5' PAC sequences, i.e., adenovirus genome bp 1–269; m.u. 0–0.75 or adenovirus genome bp 1–321; m.u. 0–0.89. Briefly, the 5' sequences are modified by PCR and cloned by conventional techniques into a conventional adenovirus based plasmid. A hpAP minigene is incorporated into the plasmid, which is then altered by homologous recombination with an E3 deleted adenovirus dl7001 to result in the modified vectors so that the reporter minigene is followed on its 3' end with the adenovirus sequences mu 9.6 to 78.3 and 87 to 100.

Figure 10:
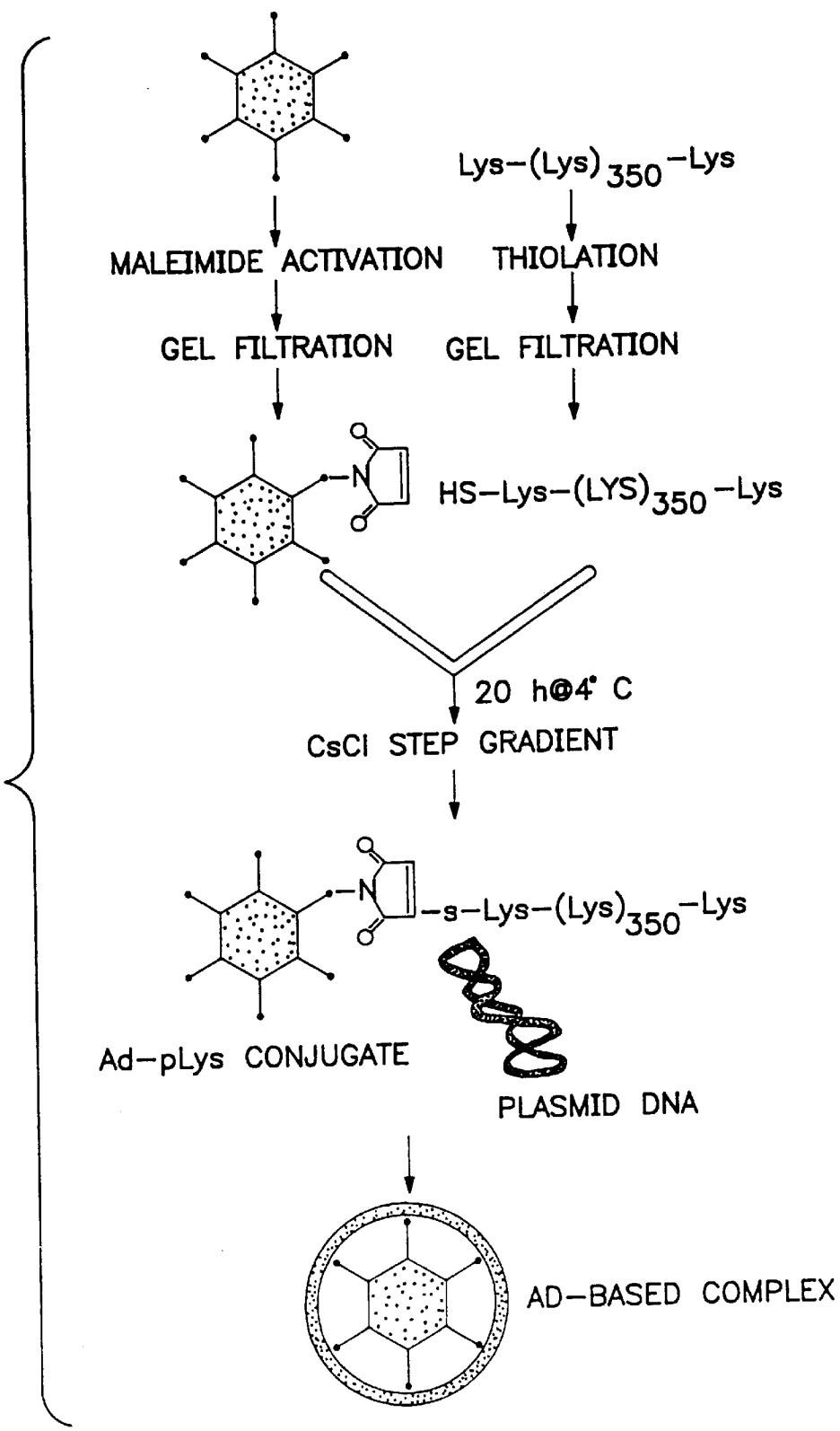
FIG. 10 is a flow diagram summarizing the synthesis of an adenovirus-based polycation helper virus conjugate and its combination with a pAdΔ shuttle vector to result in a novel viral particle complex. CsCl band purified helper adenovirus was reacted with the heterobifunctional crosslinker sulfo-SMCC and the capsid protein fiber is labeled with the nucleophilic maleimide moiety. Free sulfhydryls were introduced onto poly-L-lysine using 2-iminothiolane-HCl and mixed with the labelled adenovirus, resulting in the helper virus conjugate Ad-pLys. A unique adenovirus-based particle is generated by purifying the Ad-pLys conjugate over a CsCl gradient to remove unincorporated poly-L-lysine, followed by extensively dialyzing, adding shuttle plasmid DNAs to Ad-pLys and allowing the complex formed by the shuttle plasmid wrapped around Ad-pLys to develop.

Generation of a poly-L-lysine conjugate helper virus was demonstrated essentially as described in detail in Example 5 below and FIG. 10 by coupling poly-L-lysine to the Ad.CB-hpAP virion capsid. Alternatively, the same procedure may be employed with the PAC sequence modified helper viruses of this invention.

C. Recombinant AdΔ Virus

As stated above, a pAdΔ shuttle vector in the presence of helper virus and/or a packaging cell line permits the adenovirus-transgene sequences in the shuttle vector to be replicated and packaged into virion capsids, resulting in the recombinant AdΔ virus. The current method for producing such AdΔ virus is transfection-based and described in detail in Example 3. Briefly, helper virus is used to infect cells, such as the packaging cell line human HEK 293, which are then subsequently transfected with an pAdΔ shuttle vector containing a selected transgene by conventional methods. About 30 or more hours post-transfection, the cells are harvested, and an extract prepared. The AdΔ viral genome is packaged into virions that sediment at a lower density than the helper virus in cesium gradients. Thus, the recombinant AdΔ virus containing a selected transgene is separated from the bulk of the helper virus by purification via buoyant density ultracentrifugation in a CsCl gradient.

The yield of AdΔ transducing virus is largely dependent on the number of cells that are transfected with the pAdΔ shuttle plasmid, making it desirable to use a transfection protocol with high efficiency. One such method involves use of a poly-L-lysinylated helper adenovirus as described above. A pAdΔ shuttle plasmid containing the desired transgene under the control of a suitable promoter, as described above, is then complexed directly to the positively charged helper virus capsid, resulting in the formation of a single transfection particle containing the pAdΔ shuttle vector and the helper functions of the helper virus.

The underlying principle is that the helper adenovirus coated with plasmid pAdΔ DNA will co-transport the attached nucleic acid across the cell membrane and into the cytoplasm according to its normal mechanism of cell entry. Therefore, the poly-L-lysine modified helper adenovirus assumes multiple roles in the context of an AdΔ-based complex. First, it is the structural foundation upon which plasmid DNA can bind increasing the effective concentration. Second, receptor mediated endocytosis of the virus provides the vehicle for cell uptake of the plasmid DNA. Third, the endosomalytic activity associated with adenoviral infection facilitates the release of internalized plasmid into the cytoplasm. And the adenovirus contributes trans helper functions on which the recombinant AdΔ virus is dependent for replication and packaging of transducing viral particles. The Ad-based transfection procedure using an pAdΔ shuttle vector and a polycation-helper conjugate is detailed in Example 6. Additionally, as described previously, the helper virus-plasmid conjugate may be another form of helper virus delivery of the omitted adenovirus genes not present in the pAdΔ vector. Such a structure enables the rest of the required adenovirus genes to be divided between the plasmid and the helper virus, thus reducing the self-replication efficiency of the helper virus.

A presently preferred method of producing the recombinant AdΔ virus of this invention involves performing the above-described transfection with the crippled helper virus or crippled helper virus conjugate, as described above. A "crippled" helper virus of this invention is unable to package itself efficiently, and therefor permits ready separation of the helper virus from the newly packaged AdΔ vector of this invention by use of buoyant density ultracentrifugation in a CsCl gradient, as described in the examples below.

IV. Function of the Recombinant AdΔ Virus

Once the AdΔ virus of this invention is produced by cooperation of the shuttle vector and helper virus, the AdΔ virus can be targeted to, and taken up by, a selected target cell. The selection of the target cell also depends upon the use of the recombinant virus, i.e., whether or not the transgene is to be replicated in vitro or ex vivo for production in a desired cell type for redelivery into a patient, or in vivo for delivery to a particular cell type or tissue. Target cells may be any mammalian cell (preferably a human cell). For example, in in vivo use, the recombinant virus can target to any cell type normally infected by adenovirus, depending upon the route of administration, i.e., it can target, without limitation, neurons, hepatocytes, epithelial cells and the like. The helper adenovirus sequences supply the sequences necessary to permit uptake of the virus by the AdΔ.

Once the recombinant virus is taken up by a cell, the adenovirus flanked transgene is rescued from the parental adenovirus backbone by the machinery of the infected cell, as with other recombinant adenoviruses. Once uncoupled (rescued) from the genome of the AdΔ virus, the recombinant minigene seeks an integration site in the host chromatin and becomes integrated therein, either transiently or stably, providing expression of the accompanying transgene in the host cell.

V. Use of the AdΔ Viruses in Gone Therapy

The novel recombinant viruses and viral conjugates of this invention provide efficient gene transfer vehicles for somatic gene therapy. These viruses are prepared to contain a therapeutic gene in place of the LacZ reporter transgene illustrated in the exemplary viruses and vectors. By use of the AdΔ viruses containing therapeutic transgenes, these transgenes can be delivered to a patient in vivo or ex vivo to provide for integration of the desired gene into a target cell. Thus, these viruses can be employed to correct genetic deficiencies or defects. An example of the generation of an AdΔ gene transfer vehicle for the treatment of cystic fibrosis is described in Example 4 below. One of skill in the art can generate any number of other gene transfer vehicles by including a selected transgene for the treatment of other disorders.

The recombinant viruses of the present invention may be administered to a patient, preferably suspended in a biologically compatible solution or pharmaceutically acceptable delivery vehicle. A suitable vehicle includes sterile saline. Other aqueous and non-aqueous isotonic sterile injection solutions and aqueous and non-aqueous sterile suspensions known to be pharmaceutically acceptable carriers and well known to those of skill in the art may be employed for this purpose.

The recombinant viruses of this invention may be administered in sufficient amounts to transfect the desired cells and provide sufficient levels of integration and expression of the selected transgene to provide a therapeutic benefit without undue adverse effects or with medically acceptable physiological effects which can be determined by those skilled in the medical arts. Conventional and pharmaceutically acceptable parenteral routes of administration include direct delivery to the target organ, tissue or site, intranasal, intravenous, intramuscular, subcutaneous, intradermal and oral administration. Routes of administration may be combined, if desired.

Dosages of the recombinant virus will depend primarily on factors such as the condition being treated, the selected gene, the age, weight and health of the patient, and may thus vary among patients. A therapeutically effective human dosage of the viruses of the present invention is believed to be in the range of from about 20 to about 50 ml of saline solution containing concentrations of from about $1 \times 10^7$ to $1 \times 10^{10}$ pfu/ml virus of the present invention. A preferred human dosage is about 20 ml saline solution at the above concentrations. The dosage will be adjusted to balance the therapeutic benefit against any side effects. The levels of expression of the selected gene can be monitored to determine the selection, adjustment or frequency of dosage administration.

The following examples illustrate the construction of the pAdΔ shuttle vectors, helper viruses and recombinant AdΔ viruses of the present invention and the use thereof in gene therapy. These examples are illustrative only, and do not limit the scope of the present invention.

EXAMPLE 1

Production of pAdΔ.CMVLacZ and pAdΔc.CMVLacZ Shuttle Vectors

A. pAdΔ.CMVLacZ

A human adenovirus Ad5 sequence was modified to contain a deletion in the E1a region [map units 1 to 9.2], which immediately follows the Ad 5' region (bp 1–360) (illustrated in FIGS. 1A). Thus, the plasmid contains the 5' ITR sequence (bp 1–103), the native packaging/enhancer sequences and the TATA box for the E1a region (bp 104–360). A minigene containing the CMV immediate early enhancer/promoter, an SD/SA sequence, a cytoplasmic lacZ gene, and SV40 poly A (pA), was introduced at the site of the E1a deletion. This construct was further modified so that the minigene is followed by the 3' ITR sequences (bp 35,353-end). The DNA sequences for these components are provided in FIG. 3 and SEQ ID NO: 1 (see, also the brief description of this figure).

This construct was then cloned by conventional techniques into a pSP72 vector (Promega) backbone to make the circular shuttle vector pAdΔCMVLacZ. See the schematic of FIG. 2A. This construct was engineered with EcoRI sites flanking the 5' and 3' Ad5 ITR sequences. pAdΔ.CMVLacZ was then subjected to enzymatic digestion with EcoRI, releasing a linear fragment of the vector spanning the terminal end of the Ad 5'ITR sequence through the terminal end of the 3'ITR sequence from the plasmid backbone. See FIG. 2B.

B. pAdΔc.CMVLacZ

The shuttle vector pAdΔc.CMVLacZ (FIGS. 4A and 5) was constructed using a pSP72 (Promega) backbone so that the Ad5 5' ITR and 3' ITR were positioned head-to-tail. The organization of the Ad5 ITRs was based on reports that suggest circular Ad genomes that have the terminal ends fused together head-to-tail are infectious to levels comparable to linear Ad genomes. A minigene encoding the CMV enhancer, an SD/SA sequence, the LacZ gene, and the poly A sequence was inserted immediately following the 5' ITR. The DNA sequence of the resulting plasmid and the sequences for the individual components are reported in FIG. 5 and SEQ ID NO: 2 (see also, brief description of FIG. 5). This plasmid does not require enzymatic digestion prior to its use to produce the viral particle (see Example 3). This vector was designed to enable restriction-independent production of LacZ AdΔ vectors.

EXAMPLE 2

Construction of a Helper Virus

The Ad.CBhpAP helper virus [K. Kozarsky et al, *Som. Cell Mol. Genet.*, 19(5):449–458 (1993)] is a replication deficient adenovirus containing an alkaline phosphatase minigene. Its construction involved conventional cloning and homologous recombination techniques. The adenovirus DNA substrate was extracted from CsCl purified dl7001 virions, an Ad5 (serotype subgroup C) variant that carries a 3 kb deletion between mu 78.4 through 86 in the nonessential E3 region (provided by Dr. William Wold, Washington University, St. Louis, Mo.). Viral DNA was prepared for co-transfection by digestion with ClaI (adenovirus genomic bp position 917) which removes the left arm of the genome encompassing adenovirus map units 0–2.5. See lower diagram of FIG. 1B.

A parental cloning vector, pAd.BglII was designed. It contains two segments of wild-type Ad5 genome (i.e., map units 0–1 and 9–16.1) separated by a unique BglII cloning site for insertion of heterologous sequences. The missing Ad5 sequences between the two domains (adenovirus genome bp 361–3327) results in the deletion of E1a and the majority of E1b following recombination with viral DNA.

A recombinant hpAP minigene was designed and inserted into the BglII site of pAd.BglII to generate the complementing plasmid, pAdCBhpAP. The linear arrangement of this minigene includes:

(a) the chicken cytoplasmic β-actin promoter [nucleotides +1 to +275 as described in T. A. Kost et al, *Nucl. Acids Res.*, 11(23):8287 (1983); nucleotides 9241–8684 of FIG. 7];

(b) an SV40 intron (e.g., nucleotides 1579–1711 of SEQ ID NO: 2), (c) the sequence for human placental alkaline phosphatase (available from Genbank) and (d) an SV40 polyadenylation signal (a 237 Bam HI-BclI restriction fragment containing the cleavage/poly-A signals from both the early and late transcription units; e.g., nucleotides 837–639 of SEQ ID NO: 1).

The resulting complementing plasmid, pAdCBhpAP contained a single copy of recombinant hpAP minigene flanked by adenovirus coordinates 0–1 on one side and 9.2–16.1 on the other.

Plasmid DNA was linearized using a unique NheI site immediately 5' to adenovirus map unit zero (0) and the above-identified adenovirus substrate and the complementing plasmid DNAs were transfected to 293 cells [ATCC CRL1573] using a standard calcium phosphate transfection procedure [see, e.g., Sambrook et al, cited above]. The end result of homologous recombination involving sequences that map to adenovirus map units 9–16.1 is hybrid Ad.CB-hpAP helper virus which contains adenovirus map units 0–1 and, in place of the E1a and E1b coding regions from the dl7001 adenovirus substrate, is the hpAP minigene from the plasmid, followed by Ad sequences 9 to 100, with a deletion in the E3 (78.4–86 mu) regions.

EXAMPLE 3

Production of Recombinant AdΔ Virus

The recombinant AdΔ virus of this invention are generated by co-transfection of a shuttle vector with the helper virus in a selected packaging or non-packaging cell line.

Figure 2C:
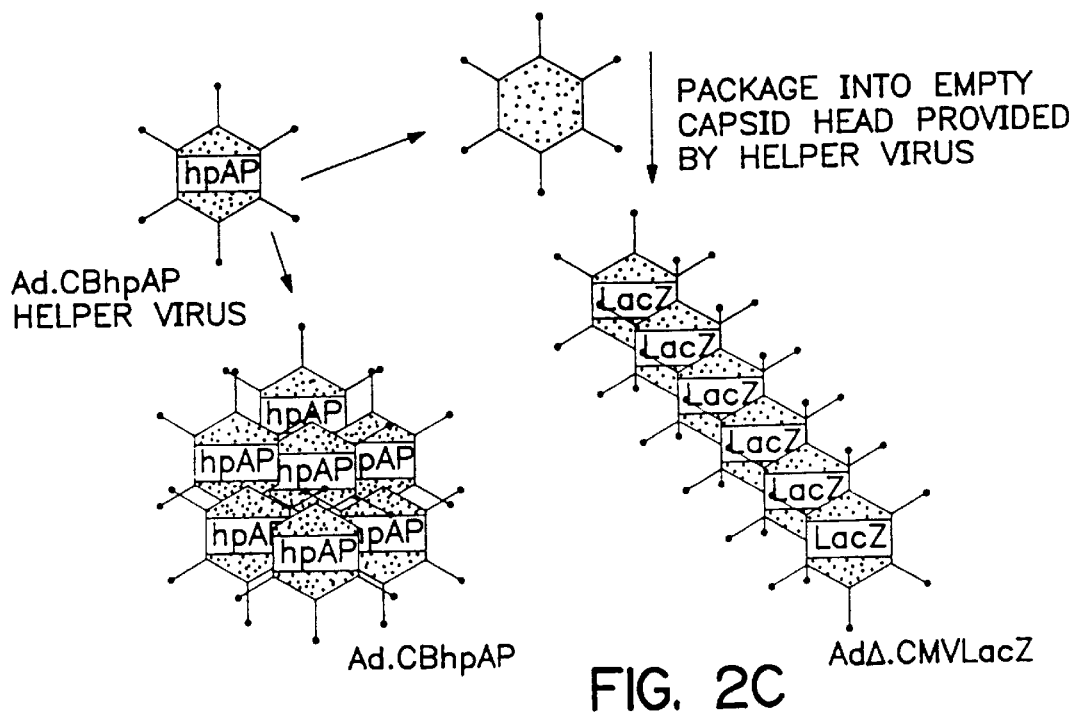
FIG. 2C is a schematic depiction of the function of the vector system. In the presence of an E1-deleted helper virus Ad.CBhpAP which encodes a reporter minigene for human placenta alkaline phosphatase (hpAP), the AdΔ.CMVLacZ genome is packaged into preformed virion capsids, distinguishable from the helper virions by the presence of the LacZ gene.

As described in detail below, the linear fragment provided in Example 1A, or the circular AdΔ genome carrying the LacZ of Example 1B, is packaged into the Ad.CBhpAP helper virus (Example 2) using conventional techniques, which provides an empty capsid head, as illustrated in FIG. 2C. Those virus particles which have successfully taken up the pAd shuttle genome into the capsid head can be distinguished from those containing the hpAP gene by virtue of the differential expression of LacZ and hpAP.

In more detail, 293 cells ($4 \times 10^7$ pfu 293 cells/150 mm dish) were seeded and infected with helper virus Ad.CBhpAP (produced as described in Example 2) at an MOI of 5 in 20 ml DMEM/2% fetal bovine serum (FBS). This helper specific marker is critical for monitoring the level of helper virus contamination in AdΔ preparations before and after purification. The helper virus provides in trans the necessary helper functions for synthesis and packaging of the AdΔCMVLacZ genome.

Two hours post infection, using either the restriction-dependent shuttle vector or the restriction-independent shuttle vector, plasmid pAdΔ.CMVLacZ (digested with EcoRI) or pAdΔc.CMVLacZ DNA, each carrying a LacZ minigene, was added to the cells by a calcium phosphate precipitate (2.5 ml calcium phosphate transfection cocktail containing 50 μg plasmid DNA).

Thirty to forty hours post-transfection, cells were harvested, suspended in 10 mM Tris-Cl (pH 8.0) (0.5 ml/150 mm plate) and frozen at −80° C. Frozen cell suspensions were subjected to three rounds of freeze (ethanol-dry ice)-thaw (37° C.) cycles to release virion capsids. Cell debris was removed by centrifugation (5,000×g for 10 minutes) and the clarified supernatant applied to a CsCl gradients to separate recombinant virus from helper virus as follows.

Supernatants (10 ml) applied to the discontinuous CsCl gradient (composed of equal volumes of CsCl at 1.2 g/ml, 1.36 g/ml, and 1.45 g/ml 10 mM Tris-Cl (pH 8.0)) were centrifuged for 8 hours at 72,128×g, resulting in separation of infectious helper virus from incompletely formed virions. Fractions were collected from the interfacing zone between the helper and top components and analyzed by Southern blot hybridization or for the presence of LacZ transducing particles. For functional analysis, aliquots (2.0 ml from each sample) from the same fractions were added to monolayers of 293 cells (in 35 mm wells) and expression of recombinant β-galactosidase determined 24 hours later. More specifically, monolayers were harvested, suspended in 0.3 ml 10 mM Tris-Cl (pH 8.0) buffer and an extract prepared by three rounds of freeze-thaw cycles. cell debris was removed by centrifugation and the supernatant tested for β-galactosidase (LacZ) activity according to the procedure described in J. Price et al, *Proc. Natl. Acad. Sci., USA*, 84:156–160 (1987). The specific activity (milliunits β-galactosidase/mg protein or reporter enzymes was measured from indicator cells. For the recombinant virus, specific activity was 116.

Fractions with β-galactosidase activity from the discontinuous gradient were sedimented through an equilibrium cesium gradient to further enrich the preparation for AdΔ virus. A linear gradient was generated in the area of the recombinant virus spanning densities 1.29 to 1.34 gm/ml. A sharp peak of the recombinant virus, detected as the appearance of the β-gal activity in infected 293 cells, eluted between 1.31 and 1.33 gm/dl. This peak of recombinant virus was located between two major $A_{260}$ nm absorbing peaks and in an area of the gradient with the helper virus was precipitously dropping off. The equilibrium sedimentation gradient accomplished another 102 to 103 fold purification of recombinant virus from helper virus. The yield of recombinant AdΔ.CMVLacZ virus recovered from a 50 plate prep after 2 sedimentations ranged from 107 to 108 transducing particles.

Analysis of lysates of cells transfected with the recombinant vector and infected with helper revealed virions capable of transducing the recombinant minigene contained within the vector. Subjecting aliquots of the fractions to Southern analysis using probes specific to the recombinant virus or helper virus revealed packaging of multiple molecular forms of vector derived sequence. The predominant form of the deleted viral genome was the size (~5.5 kb) of the corresponding double stranded DNA monomer (AdΔ.CMVLacZ) with less abundant but discrete higher molecular weight species (~10 kb and ~15 kb) also present. Full-length helper virus is 35 kb. Importantly, the peak of vector transduction activity corresponds with the highest molecular weight form of the deleted virus. These results confirm the hypothesis that ITRs and contiguous packaging sequence are the only elements necessary for incorporation into virions. An apparently ordered or preferred rearrangement of the recombinant Ad monomer genome leads to a more biologically active molecule. The fact that larger molecular species of the deleted genome are 2× and 3× fold larger than the monomer deleted virus genome suggests that the rearrangements may involve sequential duplication of the original genome.

These same procedures may be adapted for production of a recombinant AdΔ virus using a crippled helper virus or helper virus conjugate as described previously.

EXAMPLE 4

Recombinant AdΔ Virus Containing a Therapeutic Minigene

To test the versatility of the recombinant AdΔ virus system, the reporter LacZ minigene obtained from pAdΔCMVLacZ was cassette replaced with a therapeutic minigene encoding CFTR.

The minigene contained human CFTR cDNA [Riordan et al, *Science*, 245:1066–1073 (1989); nucleotides 8622–4065 of SEQ ID NO: 3] under the transcriptional control of a chimeric CMV enhancer/chicken β-actin promotor element (nucleotides +1 to +275 as described in T. A. Kost et al, *Nucl. Acids Res.*, 11(23):8287 (1983); nucleotides 9241–8684 of SEQ ID NO: 3, FIG. 7); and followed by an SV-40 poly-A sequence (nucleotides 3887–3684 of SEQ ID NO: 3, FIG. 7).

The CFTR minigene was inserted into the E1 deletion site of an Ad5 virus (called pAd.E1Δ) which contains a deletion in E1a from mu 1–9.2 and a deletion in E3 from mu 78.4–86.

Figure 6:
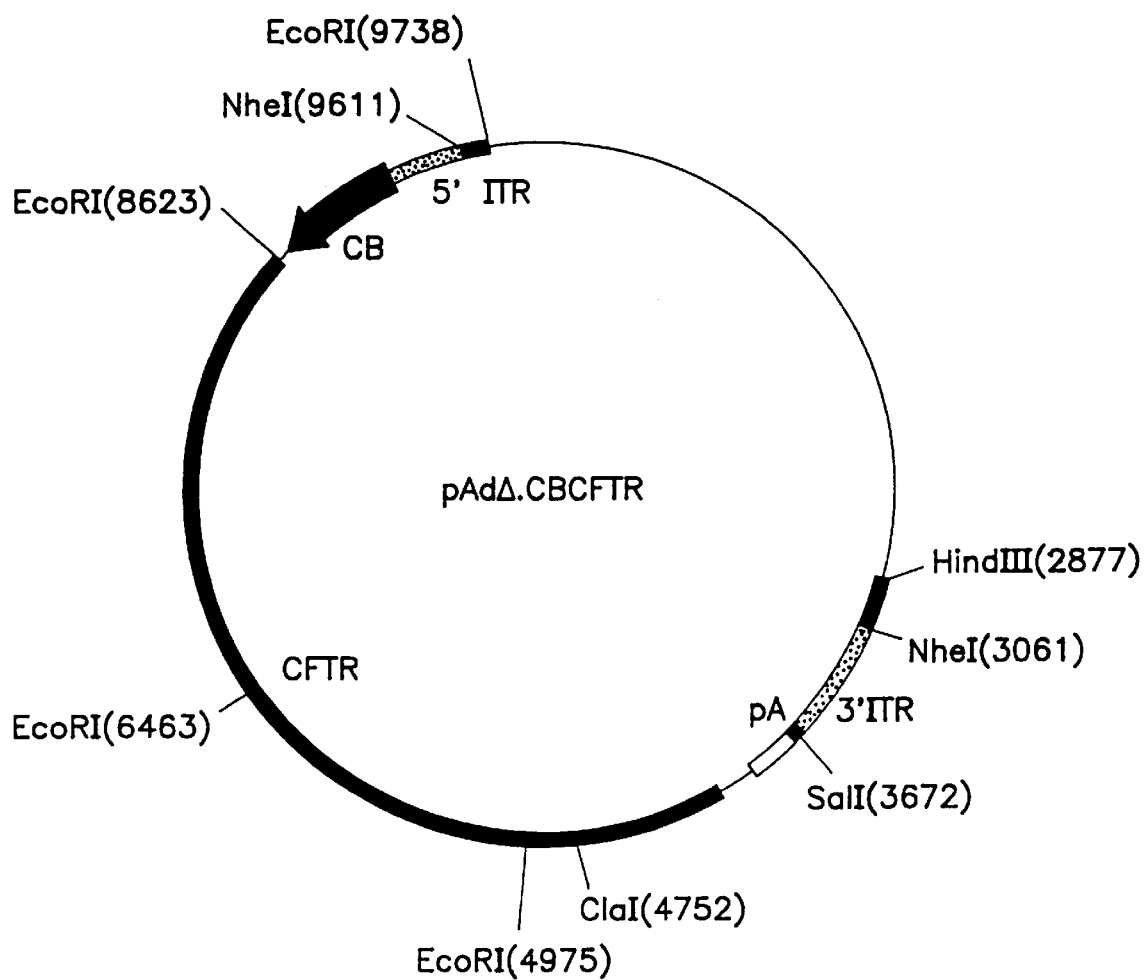
FIG. 6 is a schematic of shuttle vector pAdΔ.CBCFTR containing 5' ITR from Ad5, followed by a chimeric CMV enhancer/β actin promoter enhancer, a CFTR gene, a poly-A sequence, a 3' ITR from Ad5, and remaining plasmid sequence from plasmid pSL1180 (Pharmacia) backbone. Restriction endonuclease enzymes are represented by conventional designations in the plasmid constructs.

The resulting shuttle vector called pAdΔ.CBCFTR (see FIGS. 6 and the DNA sequence of FIG. 7 [SEQ ID NO: 3]) used the same Ad ITRs of pAdΔCMVLacZ, but the AdS sequences terminated with NheI sites instead of EcoRI. Therefore release of the minigene from the plasmid was accomplished by digestion with NheI.

The vector production system described in Example 3 was employed, using the helper virus Ad.CBhpAP (Example 2). Monolayers of 293 cells grown to 80–90% confluency in 150 mm culture dishes were infected with the helper virus at an MOI of 5. Infections were done in DMEM supplemented with 2% FBS at 20 ml media/150 mm plate. Two hours post-infection, 50 μg plasmid DNA in 2.5 ml transfection cocktail was added to each plate and evenly distributed.

Delivery of the pAdΔ.CBCFTR plasmid to 293 cells was mediated by formation of a calcium phosphate precipitate and AdΔ.CBCFTR virus resolved from Ad.CBhpAP helper virus by CsCl buoyant density ultracentrifugation as follows:

Cells were left in this condition for 10–14 h, afterwhich the infection/transfection media was replaced with 20 ml fresh DMEM/2% FBS. Approximately 30 h post-transfection, cells were harvested, suspended in 10 mM Tris-Cl (pH 8.0) buffer (0.5 ml/150 mm plate), and stored at −80° C.

Frozen cell suspensions were lysed by three sequential rounds of freeze (ethanol-dry ice)-thaw (37° C.). Cell debris was removed by centrifugation (5,000×g for 10 min) and 10 ml clarified extract layered onto a CsCl step gradient composed of three 9.0 ml tiers with densities 1.45 g/ml, 1.36 g/ml, and 1.20 g/ml CsCl in 10 mM Tris-Cl (pH 8.0) buffer. Centrifugation was performed at 20,000 rpm in a Beckman SW-28 rotor for 8 h at 4° C. Fractions (1.0 ml) were collected from the bottom of the centrifuge tube and analyzed for rAAd transducing vectors. Peak fractions were combined and banded to equilibrium. Fractions containing transducing virions were dialyzed against 20 mM HEPES (pH 7.8)/150 mM NaCl (HBS) and stored frozen at −80° C. in the presence of 10% glycerol or as a liquid stock at −20° C. (HBS+40% glycerol).

Fractions collected after ultracentrifugation were analyzed for transgene expression and vector DNA. For lacZ ΔrAd vectors, 2 μl aliquots were added to 293 cell monolayers seeded in 35 mm culture wells. Twenty-four hours later cells were harvested, suspended in 0.3 ml 10 mM Tris-Cl (pH 8.0) buffer, and lysed by three rounds of freeze-thaw. Cell debris was removed by centrifugation (15,000×g for 10 min) and assayed for total protein [Bradford, (1976)] and β-galactosidase activity [Sambrook et al, (1989)] using ONPG (o-Nitrophenyl β-D-galactopyranoside) as substrate.

Expression of CFTR protein from the AdΔ.CBCFTR vector was determined by immunofluorescence localization. Aliquots of AdΔ.CBCFTR, enriched by two-rounds of ultracentrifugation and exchanged to HBS storage buffer, were added to primary cultures of airway epithelial cells obtained from the lungs of CF transplant recipients. Twenty-four hours after the addition of vector, cells were harvested and affixed to glass slides using centrifugal force (Cytospin 3, Shandon Scientific Limited). Cells were fixed with freshly prepared 3% paraformaldehyde in PBS (1.4 mM $KH_2PO_4$, 4.3 mM $Na_2HPO_4$, 2.7 mM KCl, and 137 mM NaCl) for 15 min at room temperature (RT), washed twice in PBS, and permeabilized with 0.05% NP-40 for 10 min at RT. The immunofluorescence procedure began with a blocking step in 10% goat serum (PBS/GS) for 1 h at RT, followed by binding of the primary monoclonal mouse anti-human CFTR (R-domain specific) antibody (Genzyme) diluted 1:500 in PBS/GS for 2 h at RT. Cells were washed extensively in PBS/GS and incubated for 1 h at RT with a donkey anti-mouse IgG (H+L) FITC conjugated antibody (Jackson ImmunoResearch Laboratories) diluted 1:100 in PBS/GS.

For Southern analysis of vector DNA, 5 μl aliquots were taken directly from CsCl fractions and incubated with 20 μl capsid digestion buffer (50 mM Tris-Cl, pH 8.0; 1.0 mM EDTA, pH 8.0; 0.5% SDS, and 1.0 mg/ml Proteinase K) at 50° C. for 1 h. The reactions were allowed to cool to RT, loading dye was added, and electrophoresed through a 1.2% agarose gel. Resolved DNAs were electroblotted onto a nylon membrane (Hybond-N) and hybridized with a 32-P labeled restriction fragment. Blots were analyzed by autoradiography or scanned on a Phosphorimager 445 SI (Molecular Dynamics).

The results that were obtained from Southern blot analysis of gradient fractions revealed a distinct viral band that migrated faster than the helper Ad.CBhpAP DNA. The highest viral titers mapped to fractions 3 and 4. Quantitation of the bands in fraction 4 indicated the titer of Ad.CBhpAP was approximately 1.5× greater than AdΔCBCFTR. However, if the size difference between the two viruses is factored in (Ad.CBhpAP=35 kb; AdΔCBCFTR=6.2 kb), the viral titer (where 1 particle=1 DNA molecule) of AdΔCB.CFTR is at least 4-fold greater than the viral titer of Ad.CBhpAP.

While Southern blot analysis of gradient fractions was useful for showing the production of AdΔ viral particles, it also demonstrated the utility of ultracentrifugation for purifying AdΔ viruses. Considering the latter of these, both LacZ and CFTR transducing viruses banded in CsCl to an intermediate density between infectious adenovirus helper virions (1.34 g/ml) and incompletely formed capsids (1.31 g/ml). The lighter density relative to helper virus likely results from the smaller genome carried by the AdΔ viruses. This further suggests changes in virus size influences the density and purification of AdΔ virus. Regardless, the ability to separate AdΔ virus from the helper virus is an important observation and suggests further purification may be achieved by successive rounds of banding through CsCl.

This recombinant virus is useful in gene therapy alone, or preferably, in the form of a conjugate prepared as described herein.

EXAMPLE 5

Correction of Genetic Defect in CF airway Epithelial Cells with AdΔCB.CFTR

Treatment of cystic fibrosis, utilizing the recombinant virus provided above, is particularly suited for in vivo, lung-directed, gene therapy. Airway epithelial cells are the most desirable targets for gene transfer because the pulmonary complications of CF are usually its most morbid and life-limiting.

The recombinant AdΔCB.CFTR virus was fractionated on sequential CsCl gradients and fractions containing CFTR sequences, migrating between the adenovirus and top components fractions described above were used to infect primary cultures of human airway epithelial cells derived from the lungs of a CF patient. The cultures were subsequently analyzed for expression of CFTR protein by immunocytochemistry. Immunofluorescent detection with mouse anti-human CFTR (R domain specific) antibody was performed 24 hours after the addition of the recombinant virus. Analysis of mock infected CF cells failed to reveal significant binding to the R domain specific CFTR antibody. Primary airway epithelium cultures exposed to the recombinant virus demonstrated high levels of CFTR protein in 10–20% of the cells.

Thus, the recombinant virus of the invention, containing the CFTR gene, may be delivered directly into the airway, e.g. by a formulating the virus above, into a preparation which can be inhaled. For example, the recombinant virus or conjugate of the invention containing the CFTR gene, is suspended in 0.25 molar sodium chloride. The virus or conjugate is taken up by respiratory airway cells and the gene is expressed.

Alternatively, the virus or conjugates of the invention may be delivered by other suitable means, including site-directed injection of the virus bearing the CFTR gene. In the case of CFTR gene delivery, preferred solutions for bronchial instillation are sterile saline solutions containing in the range of from about $1 \times 10^7$ to $1 \times 10^{10}$ pfu/ml, more particularly, in the range of from about $1 \times 10^8$ to $1 \times 10^9$ pfu/ml of the virus of the present invention.

Other suitable methods for the treatment of cystic fibrosis by use of gene therapy recombinant viruses of this invention may be obtained from the art discussions of other types of gene therapy vectors for CF. See, for example, U.S. Pat. No. 5,240,846, incorporated by reference herein.

EXAMPLE 6

Synthesis of Polycation Helper Virus Conjugate

Another version of the helper virus of this invention is a polylysine conjugate which enables the pAdΔ shuttle plasmid to complex directly with the helper virus capsid. This conjugate permits efficient delivery of shuttle plasmid pAdΔ shuttle vector in tandem with the helper virus, thereby removing the need for a separate transfection step. See, FIG. 10 for a diagrammatic outline of this construction. Alternatively, such a conjugate with a plasmid supplying some Ad genes and the helper supplying the remaining necessary genes for production of the AdΔ viral vector provides a novel way to reduce contamination of the helper virus, as discussed above.

Purified stocks of a large-scale expansion of Ad.CBhpAP were modified by coupling poly-L-lysine to the virion capsid essentially as described by K. J. Fisher and J. M. Wilson, Biochem. J., 299:49–58 (1994), resulting in an Ad.CBhpAP-(Lys)$_n$ conjugate. The procedure involves three steps.

First, CsCl band purified helper virus Ad.CBhpAP was reacted with the heterobifunctional crosslinker sulfo-SMCC [sulfo-(N-succinimidyl-4-(N-maleimidomethyl) cyclohexane-l-carboxylate] (Pierce). The conjugation reaction, which contained 0.5 mg (375 nmol) of sulpho-SMCC and $6 \times 10^{12}$ A$_{260}$ helper virus particles in 3.0 ml of HBS, was incubated at 30° C. for 45 minutes with constant gentle shaking. This step involved formation of a peptide bond between the active N-hydroxysuccinimide (NHS) ester of sulpho-SMCC and a free amine (e.g. lysine) contributed by an adenovirus protein sequence (capsid protein) in the vector, yielding a maleimide-activated viral particle. The activated adenovirus is shown in FIG. 10 having the capsid protein fiber labeled with the nucleophilic maleimide moiety. In practice, other capsid polypeptides including hexon and penton base are also targeted.

Unincorporated, unreacted cross-linker was removed by gel filtration on a 1 cm×15 cm Bio-Gel P-6DG (Bio-Rad Laboratories) column equilibrated with 50 mM Tris/HCl buffer, pH 7.0, and 150 mM NaCl. Peak A$_{260}$ fractions containing maleimide-activated helper virus were combined and placed on ice.

Second, poly-L-lysine having a molecular mass of 58 kDa at 10 mg/ml in 50 mM triethanolamine buffer (pH 8.0), 150 mM NaCl and 1 mM EDTA was thiolated with 2-imminothiolane/HCl (Traut's Reagent; Pierce) to a molar ratio of 2 moles-SH/mole polylysine under N$_2$; the cyclic thioimidate reacts with the poly(L-lysine) primary amines resulting in a thiolated polycation. After a 45 minute incubation at room temperature the reaction was applied to a 1 cm×15 cm Bio-Gel P6DG column equilibrated with 50 mM Tris/HCl buffer (pH 7.0), 150 mM NaCl and 2 mM EDTA to remove unincorporated Traut's Reagent.

Quantification of free thiol groups was accomplished with Ellman's reagent [5,5'-dithio-bis-(2-nitrobenzoic acid)], revealing approximately 3–4 mol of -SH/mol of poly(L-lysine). The coupling reaction was initiated by adding $1 \times 10^{12}$ A$_{260}$ particles of maleimide-activated helper virus/mg of thiolated poly(L-lysine) and incubating the mixture on ice at 4° C. for 15 hours under argon. 2-mercaptoethylamine was added at the completion of the reaction and incubation carried out at room temperature for 20 minutes to block unreacted maleimide sites.

Virus-polylysine conjugates, Ad.CPAP-p(Lys)$_n$, were purified away from unconjugated poly(L-lysine) by ultracentrifugation through a CsCl step gradient with an initial composition of equal volumes of 1.45 g/ml (bottom step) and 1.2 g/ml (top step) CsCl in 10 mM Tris/HCl buffer (pH 8.0). Centrifugation was at 90,000 g for 2 hours at 5° C. The final product was dialyzed against 20 mM Hepes buffer (pH 7.8) containing 150 mM NaCl (HBS).

EXAMPLE 7

Formation of AdΔ/helper-pLys Viral Particle

The formation of Ad.CBhpAP-pLys/pAdΔ.CMVLacZ particle is initiated by adding 20 μg plasmid pAdΔ.CMVLacZ DNAs to $1.2 \times 10^{12}$ A$_{260}$ particles Ad.CBhpAP-pLys in a final volume of 0.2 ml DMEM and allowing the complex to develop at room temperature for between 10–15 minutes. This ratio typically represents the plasmid DNA binding capacity of a standard lot of adenovirus-pLys conjugate and gives the highest levels of plasmid transgene expression.

The resulting trans-infection particle is transfected onto 293 cells ($4 \times 10^7$ cells seeded on a 150 mm dish). Thirty hours after transfection, the particles are recovered and subjected to a freeze/thaw technique to obtain an extract. The extract is purified on a CsCl step gradient with gradients at 1.20 g/ml, 1.36 g/ml and 1.45 g/ml. After centrifugation at 90,000×g for 8 hours, the AdΔ vectors were obtained from a fraction under the top components as identified by the presence of LacZ, and the helper virus was obtained from a smaller, denser fraction, as identified by the presence of hpAP.

EXAMPLE 8

Construction of Modified Helper Viruses with Crippled Packaging (PAC) Sequences

This example refers to FIGS. 9A through 9C, 10A and 10B in the design of modified helper viruses of this invention.

Figure 8A:
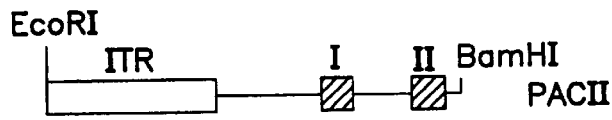
FIG. 8A illustrates the generation of 5' adenovirus terminal sequence that contained PAC domains I and II by PCR. See, arrows indicating righthand and lefthand (PAC II) PCR probes in FIG. 1B.
Figure 8B:
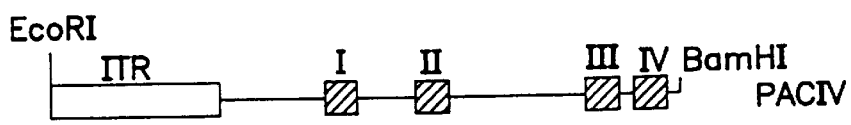
FIG. 8B illustrates the generation of 5' terminal sequence that contained PAC domains I, II, III and IV by PCR. See, arrows indicating righthand and lefthand (PAC IV) PCR probes in FIG. 1B.

Ad5 5' terminal sequences that contained PAC domains I and II (FIG. 8A) or PAC domains I, II, III, and IV (FIG. 8B) were generated by PCR from the wild type Ad5 5' genome depicted in FIG. 1B using PCR clones indicated by the arrows in FIG. 1B. The resulting amplification products (FIG. 8A and 8B) sequences differed from the wild-type Ad5 genome in the number of A-repeats carried by the left (5') end.

Figure 8C:
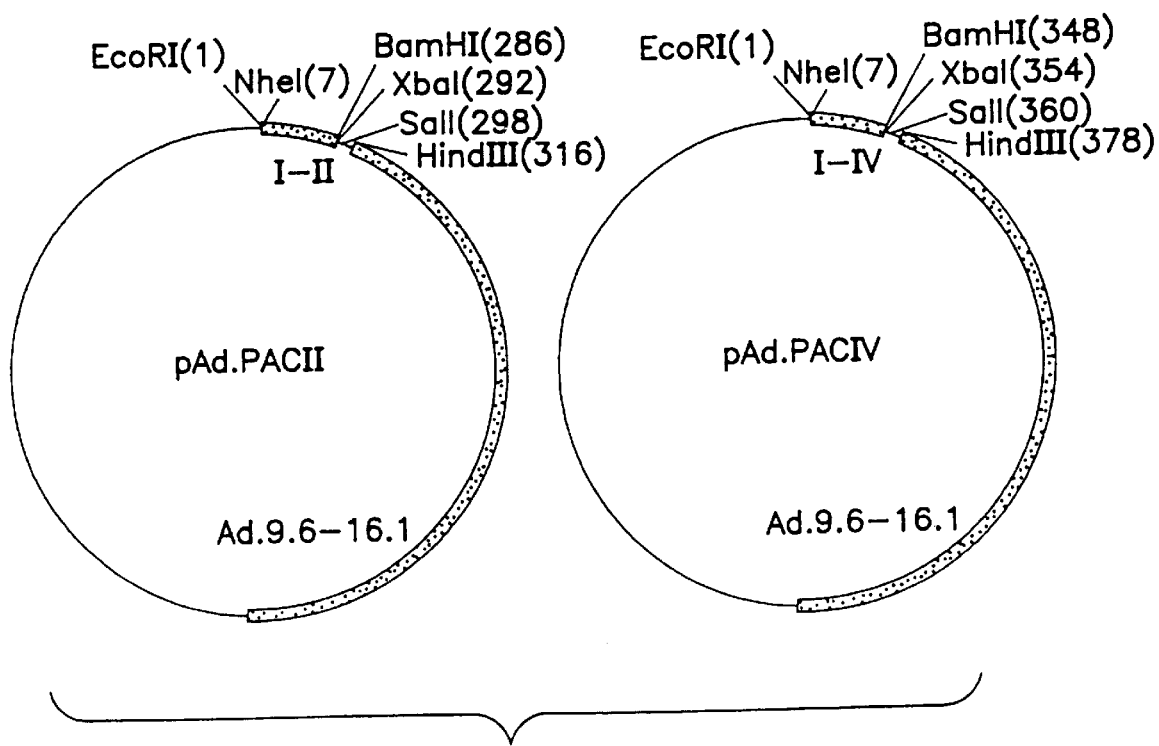
FIG. 8C depicts the amplification products subcloned into the multiple cloning site of pAd.Link.1 (IHGT Vector Core) generating pAd.PACII (domains I and II) and pAd.PACIV (domains I, II, III, and IV) resulting in crippled helper viruses, Ad.PACII and Ad.PACIV with modified packaging (PAC) signals.
Figure 9A:
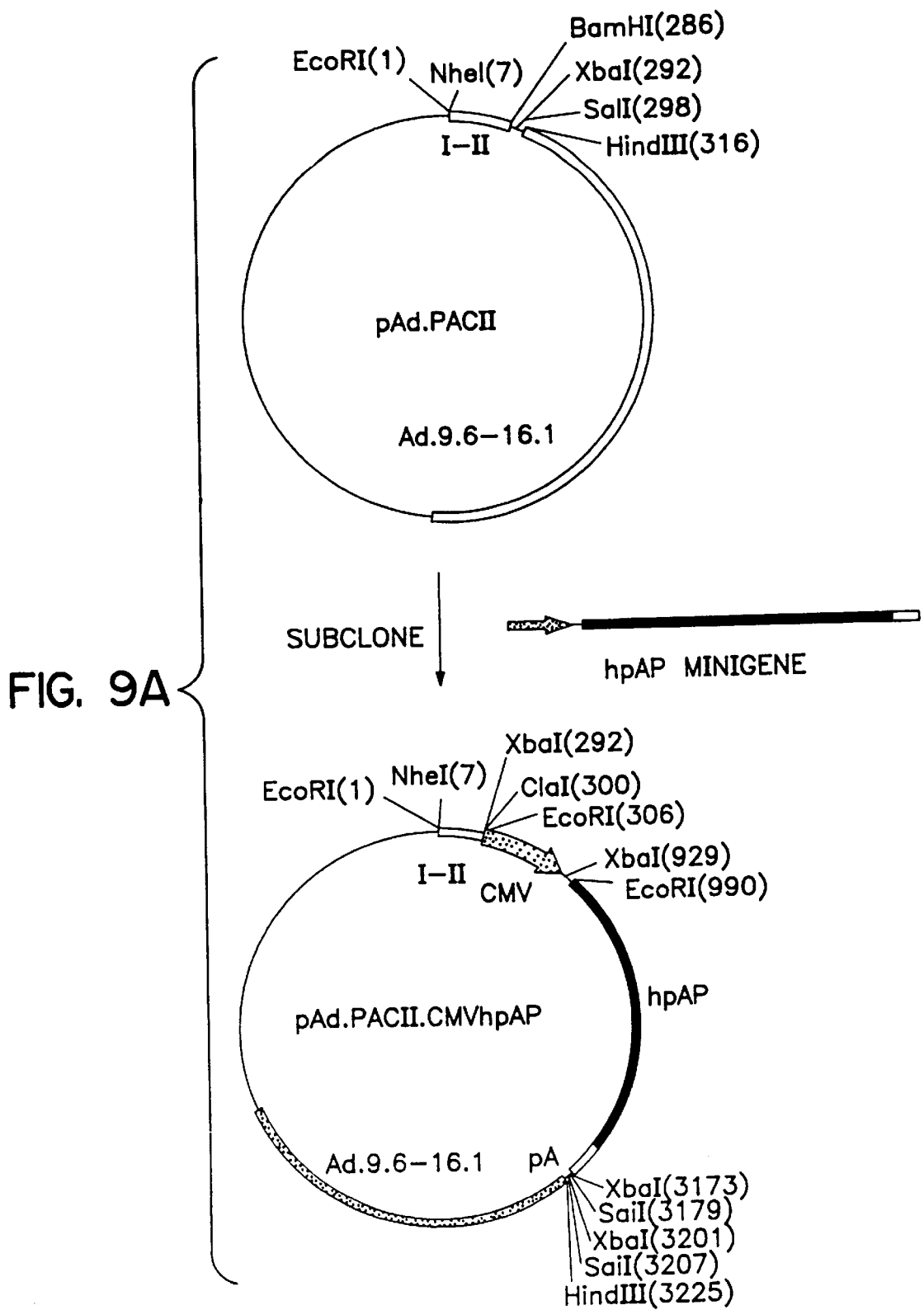
FIG. 9A is a schematic representation of the subcloning of a human placenta alkaline phosphatase reporter minigene containing the immediate early CMV enhancer/promoter (CMV), human placenta alkaline phosphatase cDNA (hpAP), and SV40 polyadenylation signal (pA) into pAd-.PACII to result in crippled helper virus vector pAdΔ.PACII.CMVhpAP. Restriction endonuclease enzymes are represented by conventional designations in the plasmid constructs.
Figure 9B:
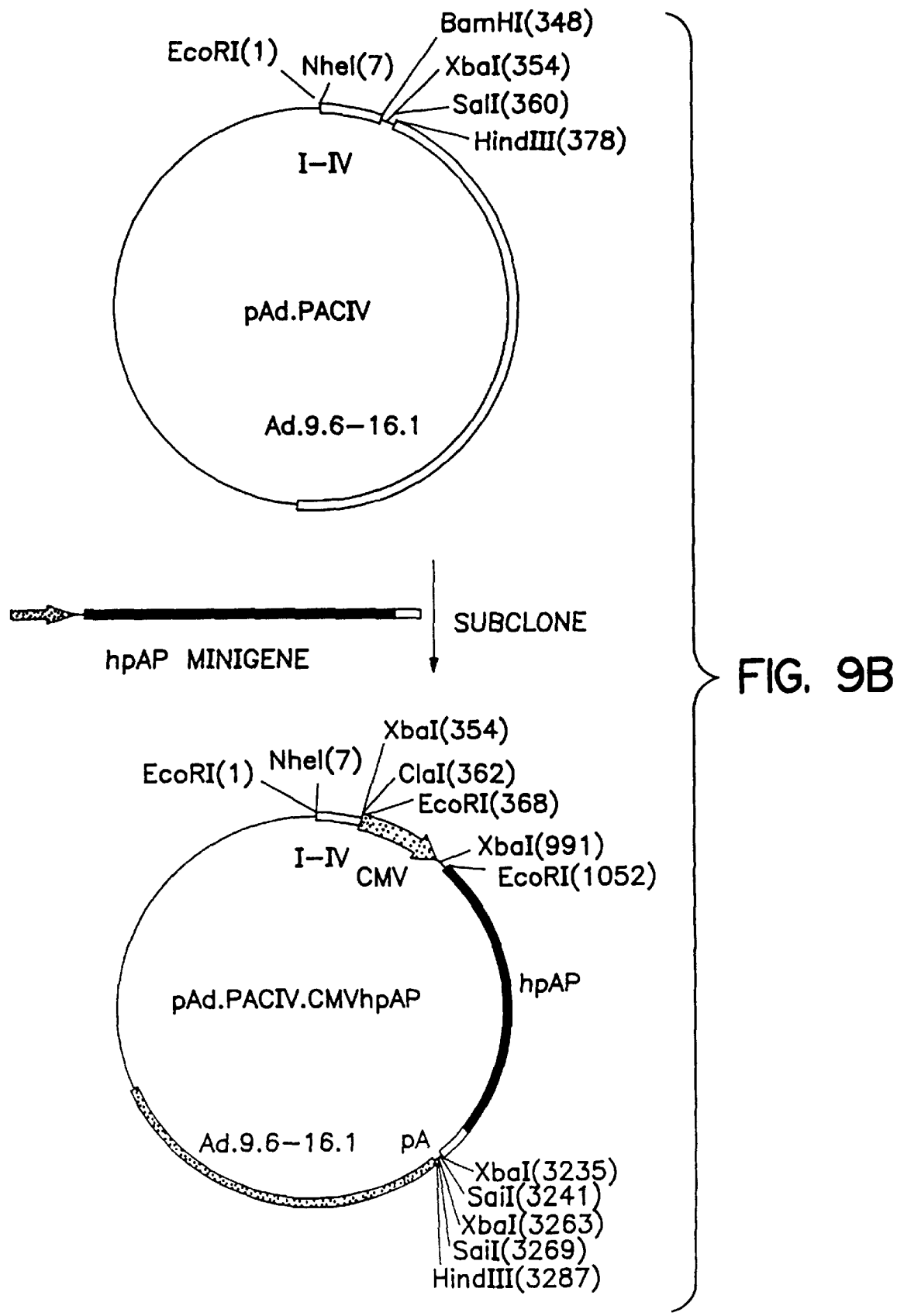
FIG. 9B is a schematic representation of the subcloning of the same minigene of FIG. 9A into pAd.PACIV to result in crippled helper virus vector pAd.PACIV.CMV.hpAP.

As depicted in FIG. 8C, these amplification products were subcloned into the multiple cloning site of pAd.Link.1 (IHGT Vector Core). pAd.Link.1 is a adenovirus based plasmid containing adenovirus m.u. 9.6 through 16.1. The insertion of the modified PAC regions into pAd.Link.1 generated two vectors pAd.PACII (containing PAC domains I and II) and pAd.PACIV (containing PAC domains I, II, III, and IV).

Thereafter, as depicted in FIGS. 10A and 10B, for each of these plasmids, a human placenta alkaline phosphatase reporter minigene containing the immediate early CMV enhancer/promoter (CMV), human placenta alkaline phosphatase cDNA (hpAP), and SV40 polyadenylation signal (pA), was subcloned into each PAC vector, generating pAd.PACII.CMVhpAP and pAd.PACIV.CMVhpAP, respectively.

These plasmids were then used as substrates for homologous recombination with dl7001 virus, described above, by co-transfection into 293 cells. Homologous recombination occurred between the adenovirus map units 9–16 of the plasmid and the crippled Ad5 virus. The results of homologous recombination were helper viruses containing Ad5 5' terminal sequences that contained PAC domains I and II or PAC domains I, II, III, and IV, followed by the minigene, and Ad5 3' sequences 9.6–78.3 and 87–100. Thus, these crippled viruses are deleted of the E1 gene and the E3 gene.

The plaque formation characteristics of the PAC helper viruses gave an immediate indication that the PAC modifications diminished the rate and extent of growth. Specifically, PAC helper virus plaques did not develop until day 14–21 post-transfection, and on maturation remained small. From previous experience, a standard first generation Ad.CBhpAP helper virus with a complete left terminal sequence would begin to develop by day 7 and mature by day 10.

Viral plaques were picked and suspended in 0.5 ml of DMEM media. A small aliquot of the virus stock was used to infect a fresh monolayer of 293 cells and histochemically stained for recombinant alkaline phosphatase activity 24 hours post-infection. Six of eight Ad.PACIV.CMVhpAP (encodes A-repeats I–IV) clones that were screened for transgene expression were positive, while all three Ad.PACII.CMVhpAP clones that were selected scored positive. The clones have been taken through two rounds of plaque purification and are currently being expanded to generate a working stock.

These crippled helper viruses are useful in the production of the AdΔ virus particles according to the procedures described in Example 3. They are characterized by containing sufficient adenovirus genes to permit the packaging of the shuttle vector genome, but their crippled PAC sequences reduce their efficiency for self-encapsidation. Thus less helper viruses are produced in favor of more AdΔ recombinant viruses. Purification of AdΔ virus particles from helper viruses is facilitated in the CsCl gradient, which is based on the weight of the respective viral particles. This facility in purification is a decided advantage of the AdΔ vectors of this invention in contrast to adenovirus vectors having only E1 or smaller deletions. The AdΔ vectors even with minigenes of up to about 15 kb are significantly different in weight than wild type or other adenovirus helpers containing many adenovirus genes.

EXAMPLE 9

AdΔ Vector Containing a full-length dystrophin transgene

Duchenne muscular dystrophy (DMD) is a common x-linked genetic disease caused by the absence of dystrophin, a 427K protein encoded by a 14 kilobase transcript. Lack of this important sarcolemmal protein leads to progressive muscle wasting, weakness, and death. One current approach for treating this lethal disease is to transfer a functional copy of the dystrophin gene into the affected muscles. For skeletal muscle, a replication-defective adenovirus represents an efficient delivery system.

According to the present invention, a recombinant plasmid pAdΔ.CMVmdys was created which contains only the Ad5 cis-elements (i.e., ITRs and contiguous packaging sequences) and harbors the full-length murine dystrophin gene driven by the CMV promoter. This plasmid was generated as follows.

pSL1180 [Pharmacia Biotech] was cut with Not I, filled in by Klenow, and religated thus ablating the Not I site in the plasmid. The resulting plasmid is termed pSL1180NN and carries a bacterial ori and Amp resistance gene. pAdΔ.CMVLacZ of Example 1 was cut with EcoRI, klenowed, and ligated with the ApaI-cut pSL1180NN to form pAdΔ.CMVLacZ (ApaI).

Figure 11:
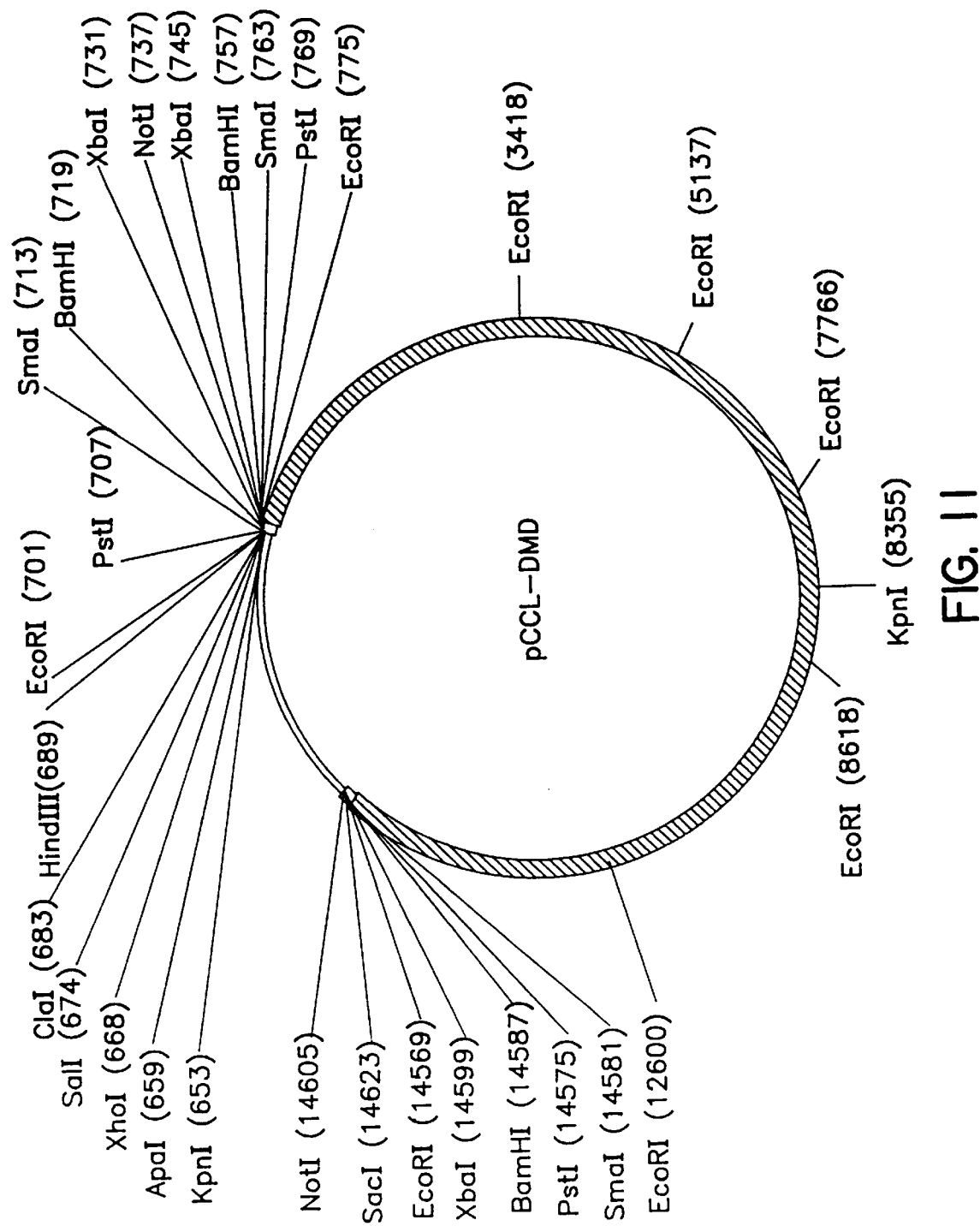
FIG. 11 is a schematic diagram of pCCL-DMD, which is described in detail in Example 9 below.

The 14 kb mouse dystrophin cDNA [sequences provided in C. C. Lee et al, Nature, 349:334–336 (1991)] was cloned in two large fragments using a lambda ZAP cloning vector (Stratagene) and subsequently cloned into the bluescript vector pSK- giving rise to the plasmid pCCL-DMD. A schematic diagram of this vector is provided in FIG. 11, which illustrates the restriction enzyme sites.

pAdΔ.CMVLacZ (ApaI) was cut with NotI and the large fragment gel isolated away from the lacZ cDNA. pCCL-DMD was also cut with NotI, gel isolated and subseqently ligated to the large NotI fragment of NotI digested pAdΔ.CMVLacZ (ApaI). The sequences of resulting vector, pAdΔ.CMVmdys, are provided in FIG. 12A–12P [SEQ ID NO:10].

This plasmid contains sequences form the left-end of the Ad5 encompassing bp 1–360 (5' ITR), a mouse dystrophin minigene under the control of the CMV promoter, and sequence from the right end of Ad5 spanning bp 35353 to the end of the genome (3' ITR). The minigene is followed by an SV-40 poly-A sequence similar to that described for the plasmids described above.

The vector production system described herein is employed. Ten 150 mm 293 plates are infected at about 90% confluency with a reporter recombinant E1-deleted virus Ad.CBhpAP at an MOI of 5 for 60 minutes at 37° C. These cells are transfected with pAdΔ.CMVmDys by calcium phosphate co-precipitation using 50 μg linearized DNA/dish for about 12–16 hours at 37° C. Media is replaced with DMEM+10% fetal bovine serum.

Full cytopathic effect is observed and a cell lysate is made by subjecting the cell pellet to freeze-thaw procedures three times. The cells are subjected to an SW41 three tier CsCl gradient for 2 hours and a band migrating between the helper adenovirus and incomplete virus is detected.

Fractions are assayed on a 6 well plate containing 293 cells infected with 5λ of fraction for 16–20 hours in DMEM+2% FBS. Cells are collected, washed with phosphate buffered saline, and resuspended in 2 ml PBS. 200λ of the 2 ml cell fractions is cytospun onto a slide.

The cells were subjected to immunofluorescence for dystrophin as follows. Cells were fixed in 10N MeOH at –20° C. The cells were exposed to a monoclonal antibody specific for the carboxy terminus of human dystrophin [NCL-DYS2; Novocastra Laboratories Ltd., UK]. Cells were then washed three times and exposed to a secondary antibody, i.e. 1:200 goat anti-mouse IgG in FITC.

The titer/fraction for seven fractions revealed in the immunofluorescent stains were calculated by the following formula and reported in Table 2 below. DFU/field=(DFU/200λ cells)×10=DFU/$10^6$ cells=(DFU/5λ viral fraction)×20=DFU/100λ fraction.

TABLE 2

| Fraction | DFU/100λ |
|---|---|
| 1 | — |
| 2 | — |
| 3 | $6 \times 10^3$ |
| 4 | $1.8 \times 10^4$ |
| 5 | $9.6 \times 10^3$ |
| 6 | 200 |
| 7 | 200 |

A virus capable of transducing the dystrophin minigene is detected as a "positive" (i.e., green fluorescent) cell. The results of the IF illustrate that heat-treated fractions do not show positive immunofluorescence. Southern blot data suggest one species on the same size as the input DNA, with helper virus contamination.

The recombinant virus can be subsequently separated from the majority of helper virus by sedimentation through cesium gradients. Initial studies demonstrate that the functional AdCMVΔmDys virions are produced, but are contaminated with helper virus. Successful purification would render AdΔ virions that are incapable of encoding viral proteins but are capable of transducing murine skeletal muscle.

EXAMPLE 10

Pseudotyping

The following experiment provides a method for preparing a recombinant AdΔ according to the invention, utilizing helper viruses from serotypes which differ from that of the pAdΔ in the transfection/infection protocol. It is unexpected that the ITRs and packaging sequence of Ad5 could be incorporated into a virion of another serotype.

A. Protocol

The basic approach is to transfect the AdΔ.CMVlacZ recombinant virus (Ad5) into 293 cells and subsequently infect the cell with the helper virus derived from a variety of Ad serotypes (2, 3, 4, 5, 7, 8, 12, and 40). When CPE is achieved, the lysate is harvested and banded through two cesium gradients.

More particularly, the Ad5-based plasmid pAdΔ.CMVlacZ of Example 1 was linearized with EcoRI. The linearized plasmids were then transfected into ten 150 mm dishes of 293 cells using calcium phosphate co-precipitation. At 10–15 hours post transfection, wild type adenoviruses (of one of the following serotypes: 2, 3, 4, 5, 7, 12, 40) were used to infect cells at an MOI of 5. The cells were then harvested at full CPE and lysed by three rounds of freeze-thawing. Pellet is resuspended in 4 mL Tris-HCl. Cell debris was removed by centrifugation and partial purification of Ad5Δ.CMVlacZ from helper virus was achieved with 2 rounds of CsCl gradient centrifugation (SW41 column, 35,000 rpm, 2 hours). Fractions were collected from the bottom of the tube (fraction #1) and analysed for lacZ transducing viruses on 293 target cells by histochemical staining (at 20h PI). Contaminating helper viruses were quantitated by plaque assay.

Except for adenovirus type 3, infection with Ad serotypes 2, 4, 5, 7, 12 and 40 were able to produce lacZ transducing viruses. The peak of β-galactosidase activity was detected between the two major $A_{260}$ absorbing peaks, where most of the helper viruses banded (data not shown). The quantity of lacZ virus recovered from 10 plates ranged from $10^4$ to $10^8$ transducing particles depending on the serotype of the helper. As expected Ad2 and Ad5 produced the highest titer of lacZ transducing viruses (Table 3). Wild type contamination was in general $10^2$–$10^3$ log higher than corresponding lacZ titer except in the case of Ad40.

B. Results

Table 3 summarizes the growth characteristics of the wild type adenoviruses as evaluated on propagation in 293 cells. This demonstrated the feasibility of utilizing these helper viruses to infect the cell line which has been transfected with the Ad5 deleted virus.

TABLE 3

| Adenovirus serotypes | p/ml | pfu/ml | p:pfu |
|---|---|---|---|
| 2 | $5 \times 10^{12}$ | $2.5 \times 10^{11}$ | 20:01 |
| 3 | $1 \times 10^{12}$ | $6.25 \times 10^9$ | 160:1 |
| 4 | $3 \times 10^{12}$ | $2 \times 10^9$ | 150:1 |
| 5 | $1 \times 10^{12}$ | $5 \times 10^{10}$ | 20:01 |
| 7a | $5 \times 10^{12}$ | $1 \times 10^{11}$ | 50:1 |
| 12 | $6 \times 10^{11}$ | $4 \times 10^9$ | 150:1 |
| 35 | $1.2 \times 10^{12}$ | | |
| 40 | $2.2 \times 10^{12}$ | $4.4 \times 10^8$ | 5000:1 |

Table 4 summarizes the results of the final purified fractions. The middle column, labeled LFU/μl quantifies the production of lacZ forming units, which is a direct measure of the packaging and propagation of pseudotyped recombinant AdΔ virus. The pfu/μl titer is an estimate of the contaminating wild type virus. AdΔ virus pseudotyped with all adenoviral strains was generated except for Ad3. The titers range between $10^7$–$10^4$.

TABLE 4

| Serotypes | LFU/ml | PFU/ml |
|---|---|---|
| 2 | $4.6 \times 10^7$ | $1.8 \times 10^9$ |
| 3 | 0 | NA |
| 4 | $6.7 \times 10^6$ | $9.3 \times 10^7$ |
| 5 | $6.3 \times 10^7$ | $1.9 \times 10^9$ |
| 7a | $3 \times 10^6$ | $1.8 \times 10^8$ |

TABLE 4-continued

| Serotypes | LFU/ml | PFU/ml |
|---|---|---|
| 12 | $1.2 \times 10^5$ | $3.3 \times 10^8$ |
| 40 | $9.5 \times 10^4$ | $1.5 \times 10^3$ |

Table 5A–5D represents a more detailed analysis of the fractions from the second purification for each of the experiments summarized in Table 4. Again, LFU/µl is the recovery of the AdΔ viruses, whereas pfu/µl represents recovery of the helper virus.

TABLE 5A

| Ad2 Fraction # | VOLUME/ul | LFU/ul | PFU/ul |
|---|---|---|---|
| 1 | 120 | 9532 | $8 \times 10^6$ |
| 2 | 100 | $5.8 \times 10^4$ | $3 \times 10^6$ |
| 3 | 100 | $8.24 \times 10^4$ | $6 \times 10^5$ |
| 4 | 100 | $9.47 \times 10^4$ | $1.2 \times 10^5$ |
| 5 | 100 | $6 \times 10^4$ | $8 \times 10^4$ |
| 6 | 100 | $2 \times 10^4$ | $6 \times 10^4$ |
| 7 | 100 | 5434 | $5 \times 10^4$ |
| Total/10 pH | | $3.32 \times 10^7$ | $1.35 \times 10^9$ |

TABLE 5B

| | VOLUME/ul | LFU/ul | PFU/ul |
|---|---|---|---|
| Ad4 Fraction # | | | |
| 1 | 100 | 1000 | $1.75 \times 10^5$ |
| 2 | 100 | $1.79 \times 10^4$ | $2.8 \times 10^5$ |
| 3 | 100 | $1.8 \times 10^4$ | $5.5 \times 10^4$ |
| 4 | 100 | 2909 | $1.25 \times 10^4$ |
| 5 | 100 | 920 | $4 \times 10^4$ |
| 6 | 100 | 153 | $3 \times 10^3$ |
| Total/10 pH | | $4 \times 10^6$ | $5.6 \times 10^7$ |
| Ad5 Fraction # | | | |
| 1 | 120 | $1.98 \times 10^4$ | $6 \times 10^6$ |
| 2 | 100 | $5.8 \times 10^4$ | $3 \times 10^6$ |
| 3 | 100 | $1.2 \times 10^5$ | $1.5 \times 10^6$ |
| 4 | 100 | $1 \times 10^5$ | $1.4 \times 10^5$ |
| 5 | 100 | $7.96 \times 10^4$ | $8 \times 10^4$ |
| 6 | 100 | 6860 | $6 \times 10^4$ |
| Total/10 pH | | $3.88 \times 10^7$ | $1.2 \times 10^9$ |

TABLE 5C

| | VOLUME/ul | LFU/ul | PFU/ul |
|---|---|---|---|
| Ad7 Fraction # | | | |
| 1 | 100 | 1225 | $5 \times 10^5$ |
| 2 | 100 | 5550 | $4 \times 10^5$ |
| 3 | 100 | 4938 | $2 \times 10^5$ |
| 4 | 100 | 3866 | $8 \times 10^4$ |
| 5 | 100 | 4134 | $6 \times 10^4$ |
| 6 | 100 | 995 | $7 \times 10^4$ |
| 7 | 100 | 230 | $6 \times 10^3$ |
| Total/10 pH | | $2.09 \times 10^6$ | $1.3 \times 10^8$ |
| Ad12 Fraction # | | | |
| 1 | 100 | 31 | $5 \times 10^5$ |
| 2 | 80 | 169 | $8.5 \times 10^5$ |
| 3 | 80 | 245 | $1.8 \times 10^5$ |
| 4 | 110 | 161 | $1.1 \times 10^5$ |
| 5 | 120 | 62 | $7 \times 10^3$ |
| Total/10 pH | | $6.14 \times 10^4$ | $1.65 \times 10^8$ |

TABLE 5D

| Ad40 Fraction # | VOLUME/ul | LFU/ul | PFU/ul |
|---|---|---|---|
| 1 | 80 | 61 | 5 |
| 2 | 80 | 184 | 3 |
| 3 | 80 | 199 | 3 |
| 4 | 80 | 168 | 1 |
| 5 | 80 | 122 | |
| 6 | 100 | 46 | |
| 7 | 100 | 32 | |
| Total/10 pH | | $6.65 \times 10^4$ | $1.1 \times 10^3$ |

C. Characterization of the Structure of Packaged Viruses

Aliquots of serial fractions were analysed by Southern blots using lacZ as a probe. In the case of Ad2 and 5, not only the linearized monomer was packaged but multiple forms of recombinant virus with distinct sizes were found. These forms correlated well with the sizes of dimers, trimers and other higher molecular weight concatamers. The linearized monomers peaked closer to the top of tube (the defective adenovirus band) than other forms. When these forms were correlated with lacz activity, a better correlation was found between the higher molecular weight forms than the monomers. With pseudotyping of Ad4 and Ad7, no linearized monomers were packaged and only higher molecular weight forms were found.

These data definitively demonstrate the production and characterization of the Δ virus and the different pseudotypes. This example illustrates a very simple way of generating pseudotype viruses.

EXAMPLE 11

AdΔ Vector Containing a FH Gene

Familial hypercholesterolemia (FH) is an autosomal dominant disorder caused by abnormalities (deficiencies) in the function or expression of LDL receptors [M. S. Brown and J. L. Goldstein, *Science*, 232(4746):34–37 (1986); J. L. Goldstein and M. S. Brown, "Familial hypercholesterolemia" in *Metabolic Basis of Inherited Disease.*, ed. C. R. Scriver et al, McGraw Hill, New York, pp1215–1250 (1989).] Patients who inherit one abnormal allele have moderate elevations in plasma LDL and suffer premature life-threatening coronary artery disease (CAD). Homozygous patients have severe hypercholesterolemia and life-threatening CAD in childhood. An FH-containing vector of the invention is constructed by replacing the lacZ minigene in the pAdΔc.CMVlacZ vector with a minigene containing the LDL receptor gene [T. Yamamoto et al, *Cell*, 39:27–38 (1984)] using known techniques and as described analogously for the dystrophin gene and CFTR in the preceding examples. Vectors bearing the LDL receptor gene can be readily constructed according to this invention. The resulting plasmid is termed pAdΔc.CMV-LDL.

This plasmid is useful in gene therapy of FH alone, or preferably, in the form of a conjugate prepared as described herein to substitute a normal LDL gene for the abnormal allele responsible for the gene.

A. Ex Vivo Gene Therapy

Ex vivo gene therapy can be performed by harvesting and establishing a primary culture of hepatocytes from a patient. Known techniques may be used to isolate and transduce the hepatocytes with the above vector(s) bearing the LDL receptor gene(s). For example, techniques of collagenase perfusion developed for rabbit liver can be adapted for human tissue and used in transduction. Following transduction, the hepatocytes are removed from the tissue culture plates and reinfused into the patient using known techniques, e.g. via a catheter placed into the inferior mesenteric vein.

B. In Vivo Gene Therapy

Desirably, the in vivo approach to gene therapy, e.g. liver-directed, involves the use of the vectors and vector conjugates described above. A preferred treatment involves infusing a vector LDL conjugate of this invention into the peripheral circulation of the patient. The patient is then evaluated for change in serum lipids and liver tissues.

The virus or conjugate can be used to infect hepatocytes in vivo by direct injection into a peripheral or portal vein ($10^7$–$10^8$ pfu/kg) or retrograde into the biliary tract (same dose). This effects gene transfer into the majority of hepatocytes.

Treatments are repeated as necessary, e.g. weekly. Administration of a dose of virus equivalent to an MOI of approximately 20 (i.e. 20 pfu/hepatocyte) is anticipated to lead to high level gene expression in the majority of hepatocytes.

All references recited above are incorporated herein by reference. Numerous modifications and variations of the present invention are included in the above-identified specification and are expected to be obvious to one of skill in the art. Such modifications and alternations to the compositions and processes of the present invention, such as various modifications to the PAC sequences or the shuttle vectors, or to other sequences of the vector, helper virus and minigene components, are believed to be encompassed in the scope of the claims appended hereto.

What is claimed is:

1. A polycation conjugate comprising:
   (a) a crippled adenovirus helper virus comprising a modified adenovirus nucleic acid sequence in place of native adenovirus nucleic acid sequence map units 0–1', which modification reduces the packaging efficiency of said virus, said virus also containing selected adenovirus nucleic acid sequences necessary to direct a productive viral infection; and
   (b) a recombinant shuttle vector comprising adenovirus nucleic acid sequences and a minigene, wherein said adenovirus nucleic acid sequences consist of adenovirus 5' and 3' cis-elements necessary for replication and virion encapsidation and said cis-elements flank said minigene; and wherein said minigene comprises a selected gene and regulatory sequences which direct expression of said selected gene in a target cell,
   wherein said helper virus is conjugated via a polycation sequence to the recombinant shuttle vector.

2. The polycation conjugate according to claim 1, wherein said 5' cis-elements in said recombinant shuttle vector comprise the native adenovirus 5' inverted terminal repeats and packaging sequences.

3. The polycation conjugate according to claim 1 wherein said 3' cis-elements in said recombinant shuttle vector comprise the native adenovirus 3' inverted terminal repeat sequences.

4. The polycation conjugate according to claim 1 wherein said selected gene in the minigene of said recombinant shuttle vector is a reporter gene.

5. The polycation conjugate according to claim 1 wherein said selected gene in the minigene of said recombinant shuttle vector is a therapeutic gene.

6. The polycation conjugate according to claim 1 wherein said modified sequence in said crippled helper virus is selected from the group consisting of:
   (i) a fragment of adenovirus nucleic acid sequence map units 0–1;
   (ii) a modified fragment of adenovirus nucleic acid sequence map units 0–1 containing at least one PAC consensus sequence in place of at least one native PAC sequence; and (iii) a modified fragment of adenovirus nucleic acid sequence map units 0–1, wherein said native PAC sequences are mutated to contain modified sequences.

7. The polycation conjugate according to claim 4 wherein said reporter gene is selected from the group consisting of the genes encoding β-galactosidase, alkaline phosphatase and green fluorescent protein.

8. The polycation conjugate according to claim 5 wherein said therapeutic gene is a normal CFTR gene.

9. The polycation conjugate according to claim 5 wherein said therapeutic gene is a normal dystrophin gene.

10. The polycation conjugate according to claim 5 wherein said therapeutic gene is an LDL receptor gene.

11. The polycation conjugate according to claim 6 wherein said modified sequence comprises Ad5 base pairs 1–269.

12. The polycation conjugate according to claim 6 wherein said modified sequence comprises Ad5 base pairs 1–321.

13. The polycation conjugate according to claim 6, wherein said fragment of adenovirus map units 0–1 contains a 5' inverted terminal repeat and one to four selected packaging sequences.

14. A method for producing a recombinant adenovirus, which comprises the steps of:(a) transfecting a selected host cell with
    (i) a recombinant shuttle vector comprising adenovirus nucleic acid sequences and a minigene, wherein said adenovirus nucleic acid sequences consist of adenovirus 5' and 3' cis-elements necessary for replication and virion encapsidation and said cis-elements flank said minigene; and wherein said minigene comprises a selected gene operatively linked to regulatory sequences which direct expression of said selected gene in a target cell; and
    (ii) a helper adenovirus comprising sufficient adenovirus nucleic acid sequences necessary for a productive viral infection,
        wherein said helper adenovirus is associated with said shuttle vector via a polycation sequence, and
    (b) isolating and purifying said recombinant virus from said cell.

15. The method according to claim 14, wherein said helper virus is a crippled helper virus comprising a modified adenovirus sequence in place of native adenovirus sequence map units 0–1, which modification reduces the packaging efficiency of said helper virus.

16. A recombinant adenovirus particle comprising, in an adenovirus capsid:
    a recombinant shuttle vector comprising adenovirus nucleic acid sequences and a minigene, wherein said adenovirus nucleic acid sequences consist of adenovirus 5' and 3' cis-elements necessary for replication and virion encapsidation and said cis-elements flank said minigene; and wherein said minigene comprises a selected gene and regulatory sequences which direct expression of said selected gene in a target cell;
        wherein said vector is conjugated via a poly-cation sequence with a helper adenovirus.

17. The adenoviral particle according to claim 16 wherein said adenovirus capsid is from an adenovirus serotype selected from the group consisting of types 2, 4, 5, 7, 12 and 40.

18. The adenoviral particle according to claim 16 wherein said selected gene is a CFTR gene.

19. The viral particle according to claim 16 wherein said selected gene is a dystrophin gene.

20. The viral particle according to claim 16 wherein said selected gene is an LDL receptor gene.

21. A method of purifying a recombinant adenovirus from a host cell in which it is produced, said method comprising the steps of:
    (a) providing a suspension of host cells containing a recombinant adenovirus comprising adenovirus 5' and 3' cis-elements necessary for replication and virion encapsidation and a minigene operatively linked to regulatory sequences which direct expression of said gene in a host cell, wherein said minigene is located between the 5' and 3' cis-elements;
    (b) lysing the host cells by subjecting the suspension to three rounds of freezing and thawing;
    (c) centrifuging the suspension, thereby obtaining clarified extract containing the recombinant adenovirus;
    (d) subjecting the clarified extract to a CsCl step gradient and centrifugation; and
    (e) collecting fractions from the CsCl gradient containing the purified recombinant adenovirus.

22. The method according to claim 21, wherein the CsCl step gradient is composed of three tiers.

23. The method according to claim 21, wherein the cells were suspended in Tris-Cl buffer prior to freezing.

* * * * *

UNITED STATES PATENT AND TRADEMARK OFFICE
CERTIFICATE OF CORRECTION

PATENT NO. : 6,001,557
DATED : December 14, 1999
INVENTOR(S) : James M. Wilson, et. al.

It is certified that error appears in the above-identified patent and that said Letters Patent is hereby corrected as shown below:

Col. 6, line 63, replace "94.8-100" with -- 98.4-100 --.

Col. 11, line 31, replace "at ecting" with -- affecting --.

Col. 12, line 42, replace "plaguing" with -- plaquing --.

Col. 14, line 64, replace "Gone" with -- Gene --.

Col. 15, line 52, replace "iimit" with -- limit --.

Col. 16, line 42, replace "AdS" with -- Ad5 --.

Col. 19, line 17, replace "AdS" with -- Ad5 --.

Col. 19, line 49, replace "rAAd" with -- rΔAd --.

Col. 24, lines 42 & 54, replace "(Apal)" with -- (ApaI) --.

Col. 28, line 22, replace "lacz" with -- lacZ --.

Col. 77, Claim 1, line 51, replace "0-1'" with -- 0-1 --.

Signed and Sealed this

Sixth Day of February, 2001

Attest:

Q. TODD DICKINSON

Attesting Officer

Director of Patents and Trademarks

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 7897 base pairs
      (B) TYPE: nucleic acid
      (C) STRANDEDNESS: double
      (D) TOPOLOGY: unknown (ii) MOLECULE TYPE: cDNA (xi) SEQUENCE DESCRIPTION: SEQ ID NO:1:

```
GAACTCGAGC AGCTGAAGCT TGAATTCCAT CATCAATAAT ATACCTTATT          50

TTGGATTGAA GCCAATATGA TAATGAGGGG GTGGAGTTTG TGACGTGGCG         100

CGGGGCGTGG GAACGGGGCG GGTGACGTAG GTTTTAGGGC GGAGTAACTT         150

GTATGTGTTG GGAATTGTAG TTTTCTTAAA ATGGGAAGTT ACGTAACGTG         200

GGAAAACGGA AGTGACGATT TGAGGAAGTT GTGGGTTTTT TGGCTTTCGT         250

TTCTGGGCGT AGGTTCGCGT GCGGTTTTCT GGGTGTTTTT TGTGGACTTT         300

AACCGTTACG TCATTTTTTA GTCCTATATA TACTCGCTCT GCACTTGGCC         350

CTTTTTTACA CTGTGACTGA TTGAGCTGGT GCCGTGTCGA GTGGTGTTTT         400

TTTAATAGGT TTTCTTTTTT ACTGGTAAGG CTGACTGTTA GGCTGCCGCT         450

GTGAAGCGCT GTATGTTGTT CTGGAGCGGG AGGGTGCTAT TTTGCCTAGG         500

CAGGAGGGTT TTTCAGGTGT TTATGTGTTT TTCTCTCCTA TTAATTTTGT         550

TATACCTCCT ATGGGGGCTG TAATGTTGTC TCTACGCCTG CGGGTATGTA         600

TTCCCCCCAA GCTTGCATGC CTGCAGGTCG ACTCTAGAGG ATCCGAAAAA         650

ACCTCCCACA CCTCCCCCTG AACCTGAAAC ATAAAATGAA TGCAATTGTT         700

GTTGTTAACT TGTTTATTGC AGCTTATAAT GGTTACAAAT AAAGCAATAG         750

CATCACAAAT TTCACAAATA AAGCATTTTT TTCACTGCAT TCTAGTTGTG         800

GTTTGTCCAA ACTCATCAAT GTATCTTATC ATGTCTGGAT CCCCGCGGCC         850

GCCTAGAGTC GAGGCCGAGT TTGTCAGAAA GCAGACCAAA CAGCGGTTGG         900

AATAATAGCG AGAACAGAGA AATAGCGGCA AAAATAATAC CCGTATCACT         950

TTTGCTGATA TGGTTGATGT CATGTAGCCA AATCGGGAAA AACGGGAAGT        1000

AGGCTCCCAT GATAAAAAAG TAAAAGAAAA AGAATAAACC GAACATCCAA        1050
```

```
AAGTTTGTGT TTTTTAAATA GTACATAATG GATTTCCTTA CGCGAAATAC        1100

GGGCAGACAT GGCCTGCCCG GTTATTATTA TTTTTGACAC CAGACCAACT        1150

GGTAATGGTA GCGACCGGCG CTCAGCTGTA ATTCCGCCGA TACTGACGGG        1200

CTCCAGGAGT CGTCGCCACC AATCCCCATA TGGAAACCGT CGATATTCAG        1250

CCATGTGCCT TCTTCCGCGT GCAGCAGATG GCGATGGCTG CTTTCCATCA        1300

GTTGCTGTTG ACTGTAGCGG CTGATGTTGA ACTGGAAGTC GCCGCGCCAC        1350

TGGTGTGGGC CATAATTCAA TTCGCGCGTC CCGCAGCGCA GACCGTTTTC        1400

GCTCGGGAAG ACGTACGGGG TATACATGTC TGACAATGGC AGATCCCAGC        1450

GGTCAAAACA GGCGGCAGTA AGGCGGTCGG GATAGTTTTC TTGCGGCCCT        1500

AATCCGAGCC AGTTTACCCG CTCTGCTACC TGCGCCAGCT GGCAGTTCAG        1550

GCCAATCCGC GCCGGATGCG GTGTATCGCT CGCCACTTCA ACATCAACGG        1600

TAATCGCCAT TTGACCACTA CCATCAATCC GGTAGGTTTT CCGGCTGATA        1650

AATAAGGTTT TCCCCTGATG CTGCCACGCG TGAGCGGTCG TAATCAGCAC        1700

CGCATCAGCA AGTGTATCTG CCGTGCACTG CAACAACGCT GCTTCGGCCT        1750

GGTAATGGCC CGCCGCCTTC CAGCGTTCGA CCCAGGCGTT AGGGTCAATG        1800

CGGGTCGCTT CACTTACGCC AATGTCGTTA TCCAGCGGTG CACGGGTGAA        1850

CTGATCGCGC AGCGGCGTCA GCAGTTGTTT TTTATCGCCA ATCCACATCT        1900

GTGAAAGAAA GCCTGACTGG CGGTTAAATT GCCAACGCTT ATTACCCAGC        1950

TCGATGCAAA AATCCATTTC GCTGGTGGTC AGATGCGGGA TGGCGTGGGA        2000

CGCGGCGGGG AGCGTCACAC TGAGGTTTTC GCCAGACGC CACTGCTGCC         2050

AGGCGCTGAT GTGCCCGGCT TCTGACCATG CGGTCGCGTT CGGTTGCACT        2100

ACGCGTACTG TGAGCCAGAG TTGCCCGGCG CTCTCCGGCT GCGGTAGTTC        2150

AGGCAGTTCA ATCAACTGTT TACCTTGTGG AGCGACATCC AGAGGCACTT        2200

CACCGCTTGC CAGCGGCTTA CCATCCAGCG CCACCATCCA GTGCAGGAGC        2250

TCGTTATCGC TATGACGGAA CAGGTATTCG CTGGTCACTT CGATGGTTTG        2300

CCCGGATAAA CGGAACTGGA AAAACTGCTG CTGGTGTTTT GCTTCCGTCA        2350

GCGCTGGATG CGGCGTGCGG TCGGCAAAGA CCAGACCGTT CATACAGAAC        2400

TGGCGATCGT TCGGCGTATC GCCAAAATCA CCGCCGTAAG CCGACCACGG        2450

GTTGCCGTTT TCATCATATT TAATCAGCGA CTGATCCACC CAGTCCCAGA        2500

CGAAGCCGCC CTGTAAACGG GGATACTGAC GAAACGCCTG CCAGTATTTA        2550

GCGAAACCGC CAAGACTGTT ACCCATCGCG TGGGCGTATT CGCAAAGGAT        2600

CAGCGGGCGC GTCTCTCCAG GTAGCGAAAG CCATTTTTTG ATGGACCATT        2650

TCGGCACAGC CGGGAAGGGC TGGTCTTCAT CCACGCGCGC GTACATCGGG        2700

CAAATAATAT CGGTGGCCGT GGTGTCGGCT CCGCCGCCTT CATACTGCAC        2750

CGGGCGGGAA GGATCGACAG ATTTGATCCA GCGATACAGC GCGTCGTGAT        2800

TAGCGCCGTG GCCTGATTCA TTCCCCAGCG ACCAGATGAT CACACTCGGG        2850

TGATTACGAT CGCGCTGCAC CATTCGCGTT ACGCGTTCGC TCATCGCCGG        2900

TAGCCAGCGC GGATCATCGG TCAGACGATT CATTGGCACC ATGCCGTGGG        2950

TTTCAATATT GGCTTCATCC ACCACATACA GGCCGTAGCG GTCGCACAGC        3000

GTGTACCACA GCGGATGGTT CGGATAATGC GAACAGCGCA CGGCGTTAAA        3050
```

| | |
|---|---|
| GTTGTTCTGC TTCATCAGCA GGATATCCTG CACCATCGTC TGCTCATCCA | 3100 |
| TGACCTGACC ATGCAGAGGA TGATGCTCGT GACGGTTAAC GCCTCGAATC | 3150 |
| AGCAACGGCT TGCCGTTCAG CAGCAGCAGA CCATTTTCAA TCCGCACCTC | 3200 |
| GCGGAAACCG ACATCGCAGG CTTCTGCTTC AATCAGCGTG CCGTCGGCGG | 3250 |
| TGTGCAGTTC AACCACCGCA CGATAGAGAT TCGGGATTTC GGCGCTCCAC | 3300 |
| AGTTTCGGGT TTTCGACGTT CAGACGTAGT GTGACGCGAT CGGCATAACC | 3350 |
| ACCACGCTCA TCGATAATTT CACCGCCGAA AGGCGCGGTG CCGCTGGCGA | 3400 |
| CCTGCGTTTC ACCCTGCCAT AAAGAAACTG TTACCCGTAG GTAGTCACGC | 3450 |
| AACTCGCCGC ACATCTGAAC TTCAGCCTCC AGTACAGCGC GGCTGAAATC | 3500 |
| ATCATTAAAG CGAGTGGCAA CATGGAAATC GCTGATTTGT GTAGTCGGTT | 3550 |
| TATGCAGCAA CGAGACGTCA CGGAAAATGC CGCTCATCCG CCACATATCC | 3600 |
| TGATCTTCCA GATAACTGCC GTCACTCCAA CGCAGCACCA TCACCGCGAG | 3650 |
| GCGGTTTTCT CCGGCGCGTA AAAATGCGCT CAGGTCAAAT TCAGACGGCA | 3700 |
| AACGACTGTC CTGGCCGTAA CCGACCCAGC GCCCGTTGCA CCACAGATGA | 3750 |
| AACGCCGAGT TAACGCCATC AAAAATAATT CGCGTCTGGC CTTCCTGTAG | 3800 |
| CCAGCTTTCA TCAACATTAA ATGTGAGCGA GTAACAACCC GTCGGATTCT | 3850 |
| CCGTGGGAAC AAACGGCGGA TTGACCGTAA TGGGATAGGT TACGTTGGTG | 3900 |
| TAGATGGGCG CATCGTAACC GTGCATCTGC CAGTTTGAGG GGACGACGAC | 3950 |
| AGTATCGGCC TCAGGAAGAT CGCACTCCAG CCAGCTTTCC GGCACCGCTT | 4000 |
| CTGGTGCCGG AAACCAGGCA AAGCGCCATT CGCCATTCAG GCTGCGCAAC | 4050 |
| TGTTGGGAAG GGCGATCGGT GCGGGCCTCT TCGCTATTAC GCCAGCTGGC | 4100 |
| CAAAGGGGGA TGTGCTGCAA GGCGATTAAG TTGGGTAACG CCAGGGTTTT | 4150 |
| CCCAGTCACG ACGTTGTAAA ACGACGGGAT CGCGCTTGAG CAGCTCCTTG | 4200 |
| CTGGTGTCCA GACCAATGCC TCCCAGACCG GCAACGAAAA TCACGTTCTT | 4250 |
| GTTGGTCAAA GTAAACGACA TGGTGACTTC TTTTTTGCTT TAGCAGGCTC | 4300 |
| TTTCGATCCC CGGGAATTGC GGCCGCGGGT ACAATTCCGC AGCTTTTAGA | 4350 |
| GCAGAAGTAA CACTTCCGTA CAGGCCTAGA AGTAAAGGCA ACATCCACTG | 4400 |
| AGGAGCAGTT CTTTGATTTG CACCACCACC GGATCCGGGA CCTGAAATAA | 4450 |
| AAGACAAAAA GACTAAACTT ACCAGTTAAC TTTCTGGTTT TTCAGTTCCT | 4500 |
| CGAGTACCGG ATCCTCTAGA GTCCGGAGGC TGGATCGGTC CCGGTCTCTT | 4550 |
| CTATGGAGGT CAAAACAGCG TGGATGGCGT CTCCAGGCGA TCTGACGGTT | 4600 |
| CACTAAACGA GCTCTGCTTA TATAGACCTC CCACCGTACA CGCCTACCGC | 4650 |
| CCATTTGCGT CAATGGGGCG GAGTTGTTAC GACATTTTGG AAAGTCCCGT | 4700 |
| TGATTTTGGT GCCAAAACAA ACTCCCATTG ACGTCAATGG GGTGGAGACT | 4750 |
| TGGAAATCCC CGTGAGTCAA ACCGCTATCC ACGCCCATTG ATGTACTGCC | 4800 |
| AAAACCGCAT CACCATGGTA ATAGCGATGA CTAATACGTA GATGTACTGC | 4850 |
| CAAGTAGGAA AGTCCCATAA GGTCATGTAC TGGGCATAAT GCCAGGCGGG | 4900 |
| CCATTTACCG TCATTGACGT CAATAGGGGG CGTACTTGGC ATATGATACA | 4950 |
| CTTGATGTAC TGCCAAGTGG GCAGTTTACC GTAAATACTC CACCCATTGA | 5000 |
| CGTCAATGGA AAGTCCCTAT TGGCGTTACT ATGGGAACAT ACGTCATTAT | 5050 |

```
TGACGTCAAT GGGCGGGGGT CGTTGGGCGG TCAGCCAGGC GGGCCATTTA    5100
CCGTAAGTTA TGTAACGACC TGCAGGTCGA CTCTAGAGGA TCTCCCTAGA    5150
CAAATATTAC GCGCTATGAG TAACACAAAA TTATTCAGAT TTCACTTCCT    5200
CTTATTCAGT TTTCCCGCGA AAATGGCCAA ATCTTACTCG GTTACGCCCA    5250
AATTTACTAC AACATCCGCC TAAAACCGCG CGAAAATTGT CACTTCCTGT    5300
GTACACCGGC GCACACCAAA AACGTCACTT TTGCCACATC CGTCGCTTAC    5350
ATGTGTTCCG CCACACTTGC AACATCACAC TTCCGCCACA CTACTACGTC    5400
ACCCGCCCCG TTCCCACGCC CCGCGCCACG TCACAAACTC CACCCCCTCA    5450
TTATCATATT GGCTTCAATC CAAAATAAGG TATATTATTG ATGATGCTAG    5500
CGAATTCATC GATGATATCA GATCTGCCGG TCTCCCTATA GTGAGTCGTA    5550
TTAATTTCGA TAAGCCAGGT TAACCTGCAT AATGAATCG GCCAACGCGC     5600
GGGGAGAGGC GGTTTGCGTA TTGGGCGCTC TTCCGCTTCC TCGCTCACTG    5650
ACTCGCTGCG CTCGGTCGTT CGGCTGCGGC GAGCGGTATC AGCTCACTCA    5700
AAGGCGGTAA TACGGTTATC CACAGAATCA GGGGATAACG CAGGAAAGAA    5750
CATGTGAGCA AAAGGCCAGC AAAAGGCCAG GAACCGTAAA AAGGCCGCGT    5800
TGCTGGCGTT TTTCCATAGG CTCCGCCCCC CTGACGAGCA TCACAAAAAT    5850
CGACGCTCAA GTCAGAGGTG GCGAAACCCG ACAGGACTAT AAAGATACCA    5900
GGCGTTTCCC CCTGGAAGCT CCCTCGTGCG CTCTCCTGTT CCGACCCTGC    5950
CGCTTACCGG ATACCTGTCC GCCTTTCTCC CTTCGGGAAG CGTGGCGCTT    6000
TCTCAATGCT CACGCTGTAG GTATCTCAGT TCGGTGTAGG TCGTTCGCTC    6050
CAAGCTGGGC TGTGTGCACG AACCCCCCGT TCAGCCCGAC CGCTGCGCCT    6100
TATCCGGTAA CTATCGTCTT GAGTCCAACC CGGTAAGACA CGACTTATCG    6150
CCACTGGCAG CAGCCACTGG TAACAGGATT AGCAGAGCGA GGTATGTAGG    6200
CGGTGCTACA GAGTTCTTGA AGTGGTGGCC TAACTACGGC TACACTAGAA    6250
GGACAGTATT TGGTATCTGC GCTCTGCTGA AGCCAGTTAC CTTCGGAAAA    6300
AGAGTTGGTA GCTCTTGATC CGGCAAACAA ACCACCGCTG CTAGCGGTGG    6350
TTTTTTTGTT TGCAAGCAGC AGATTACGCG CAGAAAAAAA GGATCTCAAG    6400
AAGATCCTTT GATCTTTTCT ACGGGGTCTG ACGCTCAGTG GAACGAAAAC    6450
TCACGTTAAG GGATTTTGGT CATGAGATTA TCAAAAAGGA TCTTCACCTA    6500
GATCCTTTTA AATTAAAAAT GAAGTTTTAA ATCAATCTAA AGTATATATG    6550
AGTAAACTTG GTCTGACAGT TACCAATGCT TAATCAGTGA GGCACCTATC    6600
TCAGCGATCT GTCTATTTCG TTCATCCATA GTTGCCTGAC TCCCCGTCGT    6650
GTAGATAACT ACGATACGGG AGGGCTTACC ATCTGGCCCC AGTGCTGCAA    6700
TGATACCGCG AGACCCACGC TCACCGGCTC CAGATTTATC AGCAATAAAC    6750
CAGCCAGCCG GAAGGGCCGA GCGCAGAAGT GGTCCTGCAA CTTTATCCGC    6800
CTCCATCCAG TCTATTAATT GTTGCCGGGA AGCTAGAGTA AGTAGTTCGC    6850
CAGTTAATAG TTTGCGCAAC GTTGTTGCCA TTGCTACAGG CATCGTGGTG    6900
TCACGCTCGT CGTTTGGTAT GGCTTCATTC AGCTCCGGTT CCCAACGATC    6950
AAGGCGAGTT ACATGATCCC CCATGTTGTG CAAAAAAGCG GTTAGCTCCT    7000
TCGGTCCTCC GATCGTTGTC AGAAGTAAGT TGGCCGCAGT GTTATCACTC    7050
```

```
ATGGTTATGG CAGCACTGCA TAATTCTCTT ACTGTCATGC CATCCGTAAG       7100

ATGCTTTTCT GTGACTGGTG AGTACTCAAC CAAGTCATTC TGAGAATAGT       7150

GTATGCGGCG ACCGAGTTGC TCTTGCCCGG CGTCAATACG GGATAATACC       7200

GCGCCACATA GCAGAACTTT AAAAGTGCTC ATCATTGGAA AACGTTCTTC       7250

GGGGCGAAAA CTCTCAAGGA TCTTACCGCT GTTGAGATCC AGTTCGATGT       7300

AACCCACTCG TGCACCCAAC TGATCTTCAG CATCTTTTAC TTTCACCAGC       7350

GTTTCTGGGT GAGCAAAAAC AGGAAGGCAA AATGCCGCAA AAAAGGGAAT       7400

AAGGGCGACA CGGAAATGTT GAATACTCAT ACTCTTCCTT TTTCAATATT       7450

ATTGAAGCAT TTATCAGGGT TATTGTCTCA TGAGCGGATA CATATTTGAA       7500

TGTATTTAGA AAAATAAACA AATAGGGGTT CCGCGCACAT TTCCCCGAAA       7550

AGTGCCACCT GACGTCTAAG AAACCATTAT TATCATGACA TTAACCTATA       7600

AAAATAGGCG TATCACGAGG CCCTTTCGTC TCGCGCGTTT CGGTGATGAC       7650

GGTGAAAACC TCTGACACAT GCAGCTCCCG GAGACGGTCA CAGCTTGTCT       7700

GTAAGCGGAT GCCGGGAGCA GACAAGCCCG TCAGGGCGCG TCAGCGGGTG       7750

TTGGCGGGTG TCGGGCTGG CTTAACTATG CGGCATCAGA GCAGATTGTA        7800

CTGAGAGTGC ACCATATGGA CATATTGTCG TTAGAACGCG GCTACAATTA       7850

ATACATAACC TTATGTATCA TACACATACG ATTTAGGTGA CACTATA          7897

(2) INFORMATION FOR SEQ ID NO:2:

(i) SEQUENCE CHARACTERISTICS:
        (A) LENGTH: 7852 base pairs
        (B) TYPE: nucleic acid
        (C) STRANDEDNESS: double
        (D) TOPOLOGY: unknown (ii) MOLECULE TYPE: cDNA (xi) SEQUENCE DESCRIPTION: SEQ ID NO:2:

GAATTCGCTA GCTAGCGGGG GAATACATAC CCGCAGGCGT AGAGACAACA       50

TTACAGCCCC CATAGGAGGT ATAACAAAAT TAATAGGAGA GAAAAACACA       100

TAAACACCTG AAAAACCCTC CTGCCTAGGC AAAATAGCAC CCTCCCGCTC       150

CAGAACAACA TACAGCGCTT CACAGCGGCA GCCTAACAGT CAGCCTTACC       200

AGTAAAAAAG AAAACCTATT AAAAAAACAC CACTCGCACG GGCACCAGCT       250

CAATCAGTCA CAGTGTAAAA AAGGGCCAAG TGCAGAGCGA GTATATATAG       300

GACTAAAAAA TGACGTAACG GTTAAAGTCC ACAAAAAACA CCCAGAAAAC       350

CGCACGCGAA CCTACGCCCA GAAACGAAAG CCAAAAAACC CACAACTTCC       400

TCAAATCGTC ACTTCCGTTT TCCCACGTTA CGTAACTTCC CATTTTAAGA       450

AAACTACAAT TCCCAACACA TACAAGTTAC TCCGCCCTAA AACCTACGTC       500

ACCCGCCCCG TTCCCACGCC CCGCGCCACG TCACAAACTC CACCCCCTCA       550

TTATCATATT GGCTTCAATC CAAAATAAGG TATATTATTG ATGATGCTAG       600

CATCATCAAT AATATACCTT ATTTTGGATT GAAGCCAATA TGATAATGAG       650

GGGGTGGAGT TTGTGACGTG GCGCGGGGCG TGGGAACGGG GCGGGTGACG       700

TAGTAGTGTG GCGGAAGTGT GATGTTGCAA GTGTGGCGGA ACACATGTAA       750

GCGACGGATG TGGCAAAAGT GACGTTTTTG GTGTGCGCCG GTGTACACAG       800

GAAGTGACAA TTTTCGCGCG GTTTTAGGCG GATGTTGTAG TAAATTTGGG       850
```

```
CGTAACCGAG TAAGATTTGG CCATTTTCGC GGGAAAACTG AATAAGAGGA       900

AGTGAAATCT GAATAATTTT GTGTTACTCA TAGCGCGTAA TATTTGTCTA       950

GGGAGATCAG CCTGCAGGTC GTTACATAAC TTACGGTAAA TGGCCCGCCT      1000

GGCTGACCGC CCAACGACCC CCGCCCATTG ACGTCAATAA TGACGTATGT      1050

TCCCATAGTA ACGCCAATAG GGACTTTCCA TTGACGTCAA TGGGTGGAGT      1100

ATTTACGGTA AACTGCCCAC TTGGCAGTAC ATCAAGTGTA TCATATGCCA      1150

AGTACGCCCC CTATTGACGT CAATGACGGT AAATGGCCCG CCTGGCATTA      1200

TGCCCAGTAC ATGACCTTAT GGGACTTTCC TACTTGGCAG TACATCTACG      1250

TATTAGTCAT CGCTATTACC ATGGTGATGC GGTTTTGGCA GTACATCAAT      1300

GGGCGTGGAT AGCGGTTTGA CTCACGGGGA TTTCCAAGTC TCCACCCCAT      1350

TGACGTCAAT GGGAGTTTGT TTTGGCACCA AAATCAACGG GACTTTCCAA      1400

AATGTCGTAA CAACTCCGCC CCATTGACGC AAATGGGCGG TAGGCGTGTA      1450

CGGTGGGAGG TCTATATAAG CAGAGCTCGT TTAGTGAACC GTCAGATCGC      1500

CTGGAGACGC CATCCACGCT GTTTTGACCT CCATAGAAGA CACCGGGACC      1550

GATCCAGCCT CCGGACTCTA GAGGATCCGG TACTCGAGGA ACTGAAAAAC      1600

CAGAAAGTTA ACTGGTAAGT TTAGTCTTTT TGTCTTTTAT TCAGGTCCC      1650

GGATCCGGTG GTGGTGCAAA TCAAAGAACT GCTCCTCAGT GGATGTTGCC      1700

TTTACTTCTA GGCCTGTACG GAAGTGTTAC TTCTGCTCTA AAAGCTGCGG      1750

AATTGTACCC GCGGCCGCAA TTCCCGGGGA TCGAAAGAGC CTGCTAAAGC      1800

AAAAAAGAAG TCACCATGTC GTTTACTTTG ACCAACAAGA ACGTGATTTT      1850

CGTTGCCGGT CTGGGAGGCA TTGGTCTGGA CACCAGCAAG GAGCTGCTCA      1900

AGCGCGATCC CGTCGTTTTA CAACGTCGTG ACTGGGAAAA CCCTGGCGTT      1950

ACCCAACTTA ATCGCCTTGC AGCACATCCC CCTTTCGCCA GCTGGCGTAA      2000

TAGCGAAGAG GCCCGCACCG ATCGCCCTTC CCAACAGTTG CGCAGCCTGA      2050

ATGGCGAATG GCGCTTTGCC TGGTTTCCGG CACCAGAAGC GGTGCCGGAA      2100

AGCTGGCTGG AGTGCGATCT TCCTGAGGCC GATACTGTCG TCGTCCCCTC      2150

AAACTGGCAG ATGCACGGTT ACGATGCGCC CATCTACACC AACGTAACCT      2200

ATCCCATTAC GGTCAATCCG CCGTTTGTTC CCACGGAGAA TCCGACGGGT      2250

TGTTACTCGC TCACATTTAA TGTTGATGAA AGCTGGCTAC AGGAAGGCCA      2300

GACGCGAATT ATTTTTGATG GCGTTAACTC GGCGTTTCAT CTCTGGTGCA      2350

ACGGGCGCTG GGTCGGTTAC GGCCAGGACA GTCGTTTGCC GTCTGAATTT      2400

GACCTGAGCG CATTTTTACG CGCCGGAGAA AACCGCCTCG CGGTGATGGT      2450

GCTGCGTTGG AGTGACGGCA GTTATCTGGA AGATCAGGAT ATGTGGCGGA      2500

TGAGCGGCAT TTTCCGTGAC GTCTCGTTGC TGCATAAACC GACTACACAA      2550

ATCAGCGATT TCCATGTTGC CACTCGCTTT AATGATGATT TCAGCCGCGC      2600

TGTACTGGAG GCTGAAGTTC AGATGTGCGG CGAGTTGCGT GACTACCTAC      2650

GGGTAACAGT TTCTTTATGG CAGGGTGAAA CGCAGGTCGC CAGCGGCACC      2700

GCGCCTTTCG GCGGTGAAAT TATCGATGAG CGTGGTGGTT ATGCCGATCG      2750

CGTCACACTA CGTCTGAACG TCGAAAACCC GAAACTGTGG AGCGCCGAAA      2800

TCCCGAATCT CTATCGTGCG GTGGTTGAAC TGCACACCGC CGACGGCACG      2850
```

```
CTGATTGAAG CAGAAGCCTG CGATGTCGGT TTCCGCGAGG TGCGGATTGA    2900

AAATGGTCTG CTGCTGCTGA ACGGCAAGCC GTTGCTGATT CGAGGCGTTA    2950

ACCGTCACGA GCATCATCCT CTGCATGGTC AGGTCATGGA TGAGCAGACC    3000

ATGGTGCAGG ATATCCTGCT GATGAAGCAG AACAACTTTA ACGCCGTGCG    3050

CTGTTCGCAT TATCCGAACC ATCCGCTGTG GTACACGCTG TGCGACCGCT    3100

ACGGCCTGTA TGTGGTGGAT GAAGCCAATA TTGAAACCCA CGGCATGGTG    3150

CCAATGAATC GTCTGACCGA TGATCCGCGC TGGCTACCGG CGATGAGCGA    3200

ACGCGTAACG CGAATGGTGC AGCGCGATCG TAATCACCCG AGTGTGATCA    3250

TCTGCTCGCT GGGGAATGAA TCAGGCCACG GCGCTAATCA CGACGCGCTG    3300

TATCGCTGGA TCAAATCTGT CGATCCTTCC CGCCCGGTGC AGTATGAAGG    3350

CGGCGGAGCC GACACCACGG CCACCGATAT TATTTGCCCG ATGTACGCGC    3400

GCGTGGATGA AGACCAGCCC TTCCCGGCTG TGCCGAAATG GTCCATCAAA    3450

AAATGGCTTT CGCTACCTGG AGAGACGCGC CCGCTGATCC TTTGCGAATA    3500

CGCCCACGCG ATGGGTAACA GTCTTGGCGG TTTCGCTAAA TACTGGCAGG    3550

CGTTTCGTCA GTATCCCCGT TTACAGGGCG GCTTCGTCTG GGACTGGGTG    3600

GATCAGTCGC TGATTAAATA TGATGAAAAC GGCAACCCGT GGTCGGCTTA    3650

CGGCGGTGAT TTTGGCGATA CGCCGAACGA TCGCCAGTTC TGTATGAACG    3700

GTCTGGTCTT TGCCGACCGC ACGCCGCATC CAGCGCTGAC GGAAGCAAAA    3750

CACCAGCAGC AGTTTTTCCA GTTCCGTTTA TCCGGGCAAA CCATCGAAGT    3800

GACCAGCGAA TACCTGTTCC GTCATAGCGA TAACGAGCTC CTGCACTGGA    3850

TGGTGGCGCT GGATGGTAAG CCGCTGGCAA GCGGTGAAGT GCCTCTGGAT    3900

GTCGCTCCAC AAGGTAAACA GTTGATTGAA CTGCCTGAAC TACCGCAGCC    3950

GGAGAGCGCC GGGCAACTCT GGCTCACAGT ACGCGTAGTG CAACCGAACG    4000

CGACCGCATG GTCAGAAGCC GGGCACATCA GCGCCTGGCA GCAGTGGCGT    4050

CTGGCGGAAA ACCTCAGTGT GACGCTCCCC GCCGCGTCCC ACGCCATCCC    4100

GCATCTGACC ACCAGCGAAA TGGATTTTTG CATCGAGCTG GGTAATAAGC    4150

GTTGGCAATT TAACCGCCAG TCAGGCTTTC TTTCACAGAT GTGGATTGGC    4200

GATAAAAAAC AACTGCTGAC GCCGCTGCGC GATCAGTTCA CCCGTGCACC    4250

GCTGGATAAC GACATTGGCG TAAGTGAAGC GACCCGCATT GACCCTAACG    4300

CCTGGGTCGA ACGCTGGAAG GCGGCGGGCC ATTACCAGGC CGAAGCAGCG    4350

TTGTTGCAGT GCACGGCAGA TACACTTGCT GATGCGGTGC TGATTACGAC    4400

CGCTCACGCG TGGCAGCATC AGGGGAAAAC CTTATTTATC AGCCGGAAAA    4450

CCTACCGGAT TGATGGTAGT GGTCAAATGG CGATTACCGT TGATGTTGAA    4500

GTGGCGAGCG ATACACCGCA TCCGGCGCGG ATTGGCCTGA ACTGCCAGCT    4550

GGCGCAGGTA GCAGAGCGGG TAAACTGGCT CGGATTAGGG CCGCAAGAAA    4600

ACTATCCCGA CCGCCTTACT GCCGCCTGTT TGACCGCTG GGATCTGCCA    4650

TTGTCAGACA TGTATACCCC GTACGTCTTC CCGAGCGAAA ACGGTCTGCG    4700

CTGCGGGACG CGCGAATTGA ATTATGGCCC ACACCAGTGG CGCGGCGACT    4750

TCCAGTTCAA CATCAGCCGC TACAGTCAAC AGCAACTGAT GGAAACCAGC    4800

CATCGCCATC TGCTGCACGC GGAAGAAGGC ACATGGCTGA ATATCGACGG    4850
```

```
TTTCCATATG GGGATTGGTG GCGACGACTC CTGGAGCCCG TCAGTATCGG      4900

CGGAATTACA GCTGAGCGCC GGTCGCTACC ATTACCAGTT GGTCTGGTGT      4950

CAAAAATAAT AATAACCGGG CAGGCCATGT CTGCCCGTAT TTCGCGTAAG      5000

GAAATCCATT ATGTACTATT TAAAAAACAC AAACTTTTGG ATGTTCGGTT      5050

TATTCTTTTT CTTTTACTTT TTTATCATGG GAGCCTACTT CCCGTTTTTC      5100

CCGATTTGGC TACATGACAT CAACCATATC AGCAAAAGTG ATACGGGTAT      5150

TATTTTTGCC GCTATTTCTC TGTTCTCGCT ATTATTCCAA CCGCTGTTTG      5200

GTCTGCTTTC TGACAAACTC GGCCTCGACT CTAGGCGGCC GCGGGGATCC      5250

AGACATGATA AGATACATTG ATGAGTTTGG ACAAACCACA ACTAGAATGC      5300

AGTGAAAAAA ATGCTTTATT TGTGAAATTT GTGATGCTAT TGCTTTATTT      5350

GTAACCATTA TAAGCTGCAA TAAACAAGTT AACAACAACA ATTGCATTCA      5400

TTTTATGTTT CAGGTTCAGG GGGAGGTGTG GGAGGTTTTT TCGGATCCTC      5450

TAGAGTCGAC GACGCGAGGC TGGATGGCCT TCCCCATTAT GATTCTTCTC      5500

GCTTCCGGCG GCATCGGGAT GCCCGCGTTG CAGGCCATGC TGTCCAGGCA      5550

GGTAGATGAC GACCATCAGG GACAGCTTCA AGGATCGCTC GCGGCTCTTA      5600

CCAGCCTAAC TTCGATCACT GGACCGCTGA TCGTCACGGC GATTTATGCC      5650

GCCTCGGCGA GCACATGGAA CGGGTTGGCA TGGATTGTAG GCGCCGCCCT      5700

ATACCTTGTC TGCCTCCCCG CGTTGCGTCG CGGTGCATGG AGCCGGGCCA      5750

CCTCGACCTG AATGGAAGCC GGCGGCACCT CGCTAACGGA TTCACCACTC      5800

CAAGAATTGG AGCCAATCAA TTCTTGCGGA GAACTGTGAA TGCGCAAACC      5850

AACCCTTGGC AGAACATATC CATCGCGTCC GCCATCTCCA GCAGCCGCAC      5900

GCGGCGCATC TCGGGCAGCG TTGGGTCCTG GCCACGGGTG CGCATGATCG      5950

TGCTCCTGTC GTTGAGGACC CGGCTAGGCT GGCGGGGTTG CCTTACTGGT      6000

TAGCAGAATG AATCACCGAT ACGCGAGCGA ACGTGAAGCG ACTGCTGCTG      6050

CAAAACGTCT GCGACCTGAG CAACAACATG AATGGTCTTC GGTTTCCGTG      6100

TTTCGTAAAG TCTGGAAACG CGGAAGTCAG CGCCCTGCAC CATTATGTTC      6150

CGGATCTGCA TCGCAGGATG CTGCTGGCTA CCCTGTGGAA CACCTACATC      6200

TGTATTAACG AAGCCTTTCT CAATGCTCAC GCTGTAGGTA TCTCAGTTCG      6250

GTGTAGGTCG TTCGCTCCAA GCTGGGCTGT GTGCACGAAC CCCCCGTTCA      6300

GCCCGACCGC TGCGCCTTAT CCGGTAACTA TCGTCTTGAG TCCAACCCGG      6350

TAAGACACGA CTTATCGCCA CTGGCAGCAG CCACTGGTAA CAGGATTAGC      6400

AGAGCGAGGT ATGTAGGCGG TGCTACAGAG TTCTTGAAGT GGTGGCCTAA      6450

CTACGGCTAC ACTAGAAGGA CAGTATTTGG TATCTGCGCT CTGCTGAAGC      6500

CAGTTACCTT CGGAAAAAGA GTTGGTAGCT CTTGATCCGG CAAACAAACC      6550

ACCGCTGGTA GCGGTGGTTT TTTTGTTTGC AAGCAGCAGA TTACGCGCAG      6600

AAAAAAAGGA TCTCAAGAAG ATCCTTTGAT CTTTTCTACG GGGTCTGACG      6650

CTCAGTGGAA CGAAAACTCA CGTTAAGGGA TTTTGGTCAT GAGATTATCA      6700

AAAAGGATCT TCACCTAGAT CCTTTTAAAT TAAAAATGAA GTTTTAAATC      6750

AATCTAAAGT ATATATGAGT AAACTTGGTC TGACAGTTAC CAATGCTTAA      6800

TCAGTGAGGC ACCTATCTCA GCGATCTGTC TATTTCGTTC ATCCATAGTT      6850
```

```
GCCTGACTCC CCGTCGTGTA GATAACTACG ATACGGAGG  GCTTACCATC         6900

TGGCCCCAGT GCTGCAATGA TACCGCGAGA CCCACGCTCA CCGGCTCCAG         6950

ATTTATCAGC AATAAACCAG CCAGCCGGAA GGGCCGAGCG CAGAAGTGGT         7000

CCTGCAACTT TATCCGCCTC CATCCAGTCT ATTAATTGTT GCCGGGAAGC         7050

TAGAGTAAGT AGTTCGCCAG TTAATAGTTT GCGCAACGTT GTTGCCATTG         7100

CTGCAGGCAT CGTGGTGTCA CGCTCGTCGT TTGGTATGGC TTCATTCAGC         7150

TCCGGTTCCC AACGATCAAG GCGAGTTACA TCATCCCCCA TGTTGTGCAA         7200

AAAAGCGGTT AGCTCCTTCG GTCCTCCGAT CGTTGTCAGA AGTAAGTTGG         7250

CCGCAGTGTT ATCACTCATG GTTATGCCAG CACTGCATAA TTCTCTTACT         7300

GTCATGCCAT CCGTAAGATG CTTTTCTGTG ACTGGTGAGT ACTCAACCAA         7350

GTCATTCTGA GAATAGTGTA TGCGGCGACC GAGTTGCTCT TGCCCGGCGT         7400

CAACACGGGA TAATACCGCG CCACATAGCA CAACTTTAAA AGTGCTCATC         7450

ATTGGAAAAC GTTCTTCGGG GCGAAAACTC TCAAGGATCT TACCGCTGTT         7500

GAGATCCAGT TCGATGTAAC CCACTCGTGC ACCCAACTGA TCTTCAGCAT         7550

CTTTTACTTT CACCAGCGTT TCTGGGTGAG CAAAAACAGG AAGGCAAAAT         7600

GCCGCAAAAA AGGGAATAAG GGCGACACGG AAATGTTGAA TACTCATACT         7650

CTTCCTTTTT CAATATTATT GAAGCATTTA TCAGGGTTAT TGTCTCATGA         7700

GCGGATACAT ATTTGAATGT ATTTAGAAAA ATAAACAAAT AGGGGTTCCG         7750

CGCACATTTC CCCGAAAAGT GCCACCTGAC GTCTAAGAAA CCATTATTAT         7800

CATGACATTA ACCTATAAAA ATAGGCGTAT CACGAGGCCC TTTCGTCTTC         7850

AA                                                            7852

(2) INFORMATION FOR SEQ ID NO:3:

(i) SEQUENCE CHARACTERISTICS:
        (A) LENGTH: 9972 base pairs
        (B) TYPE: nucleic acid
        (C) STRANDEDNESS: double
        (D) TOPOLOGY: unknown (ii) MOLECULE TYPE: cDNA (xi) SEQUENCE DESCRIPTION: SEQ ID NO:3:

TCTTCCGCTT CCTCGCTCAC TGACTCGCTG CGCTCGGTCG TTCGGCTGCG           50

GCGAGCGGTA TCAGCTCACT CAAAGGCGGT AATACGGTTA TCCACAGAAT          100

CAGGGGATAA CGCAGGAAAG AACATGTGAG CAAAAGGCCA GCAAAAGGCC          150

AGGAACCGTA AAAAGGCCGC GTTGCTGGCG TTTTTCCATA GGCTCCGCCC          200

CCCTGACGAG CATCACAAAA ATCGACGCTC AAGTCAGAGG TGGCGAAACC          250

CGACAGGACT ATAAAGATAC CAGGCGTTTC CCCCTGGAAG CTCCCTCGTG          300

CGCTCTCCTG TTCCGACCCT GCCGCTTACC GGATACCTGT CCGCCTTTCT          350

CCCTTCGGGA AGCGTGGCGC TTTCTCATAG CTCACGCTGT AGGTATCTCA          400

GTTCGGTGTA GGTCGTTCGC TCCAAGCTGG GCTGTGTGCA CGAACCCCCC          450

GTTCAGCCCG ACCGCTGCGC CTTATCCGGT AACTATCGTC TTGAGTCCAA          500

CCCGGTAAGA CACGACTTAT CGCCACTGGC AGCAGCCACT GGTAACAGGA          550

TTAGCAGAGC GAGGTATGTA GGCGGTGCTA CAGAGTTCTT GAAGTGGTGG          600
```

| | |
|---|---|
| CCTAACTACG GCTACACTAG AAGAACAGTA TTTGGTATCT GCGCTCTGCT | 650 |
| GAAGCCAGTT ACCTTCGGAA AAAGAGTTGG TAGCTCTTGA TCCGGCAAAC | 700 |
| AAACCACCGC TGGTAGCGGT GGTTTTTTTG TTTGCAAGCA GCAGATTACG | 750 |
| CGCAGAAAAA AAGGATCTCA AGAAGATCCT TTGATCTTTT CTACGGGTC | 800 |
| TGACGCTCAG TGGAACGAAA ACTCACGTTA AGGGATTTTG GTCATGAGAT | 850 |
| TATCAAAAAG GATCTTCACC TAGATCCTTT TAAATTAAAA ATGAAGTTTT | 900 |
| AAATCAATCT AAAGTATATA TGAGTAAACT TGGTCTGACA GTTACCAATG | 950 |
| CTTAATCAGT GAGGCACCTA TCTCAGCGAT CTGTCTATTT CGTTCATCCA | 1000 |
| TAGTTGCCTG ACTCCCCGTC GTGTAGATAA CTACGATACG GGAGGGCTTA | 1050 |
| CCATCTGGCC CCAGTGCTGC AATGATACCG CCAGACCCAC GCTCACCGGC | 1100 |
| TCCAGATTTA TCAGCAATAA ACCAGCCAGC CGGAAGGGCC GAGCGCAGAA | 1150 |
| GTGGTCCTGC AACTTTATCC GCCTCCATCC AGTCTATTAA TTGTTGCCGG | 1200 |
| GAAGCTAGAG TAAGTAGTTC GCCAGTTAAT AGTTTGCGCA ACGTTGTTGC | 1250 |
| CATTGCTACA GGCATCGTGG TGTCACGCTC GTCGTTTGGT ATGGCTTCAT | 1300 |
| TCAGCTCCGC TTCCCAACGA TCAAGGCGAG TTACATGATC CCCCATGTTG | 1350 |
| TGCAAAAAAG CGGTTAGCTC CTTCGGTCCT CCGATCGTTG TCAGAAGTAA | 1400 |
| GTTGGCCGCA GTGTTATCAC TCATGGTTAT GGCAGCACTG CATAATTCTC | 1450 |
| TTACTGTCAT GCCATCCGTA AGATGCTTTT CTGTGACTGG TGAGTACTCA | 1500 |
| ACCAAGTCAT TCTGAGAATA GTGTATGCGG CGACCGAGTT GCTCTTGCCC | 1550 |
| GGCGTCAATA CGGGATAATA CCGCGCCACA TAGCAGAACT TTAAAAGTGC | 1600 |
| TCATCATTGG AAAACGTTCT TCGGGGCGAA AACTCTCAAG GATCTTACCG | 1650 |
| CTGTTGAGAT CCAGTTCGAT GTAACCCACT CGTGCACCCA ACTGATCTTC | 1700 |
| AGCATCTTTT ACTTTCACCA GCGTTTCTGG GTGAGCAAAA ACAGGAAGGC | 1750 |
| AAAATGCCGC AAAAAAGGGA ATAAGGGCGA CACGGAAATG TTGAATACTC | 1800 |
| ATACTCTTCC TTTTTCAATA TTATTGAAGC ATTTATCAGG GTTATTGTCT | 1850 |
| CATGAGCGGA TACATATTTG AATGTATTTA GAAAAATAAA CAAATAGGGG | 1900 |
| TTCCGCGCAC ATTTCCCCGA AAAGTGCCAC CTGACGTCTA AGAAACCATT | 1950 |
| ATTATCATGA CATTAACCTA TAAAAATAGG CGTATCACGA GGCCCTTTCG | 2000 |
| TCTCGCGCGT TTCGGTGATG ACGGTGAAAA CCTCTGACAC ATGCAGCTCC | 2050 |
| CGGAGACGGT CACAGCTTGT CTGTAAGCGG ATGCCGGGAG CAGACAAGCC | 2100 |
| CGTCAGGGCG CGTCAGCGGG TGTTGGCGGG TGTCGGGGCT GGCTTAACTA | 2150 |
| TGCGGCATCA GAGCAGATTG TACTGAGAGT GCACCATAAA ATTGTAAACG | 2200 |
| TTAATATTTT GTTAAAATTC GCGTTAAATT TTTGTTAAAT CAGCTCATTT | 2250 |
| TTTAACCAAT AGGCCGAAAT CGGCAAAATC CCTTATAAAT CAAAAGAATA | 2300 |
| GCCCGAGATA GGGTTGAGTG TTGTTCCAGT TTGGAACAAG AGTCCACTAT | 2350 |
| TAAAGAACGT GGACTCCAAC GTCAAAGGGC GAAAAACCGT CTATCAGGGC | 2400 |
| GATGGCCCAC TACGTGAACC ATCACCCAAA TCAAGTTTTT TGGGGTCGAG | 2450 |
| GTGCCGTAAA GCACTAAATC GGAACCCTAA AGGGAGCCCC CGATTTAGAG | 2500 |
| CTTGACGGGG AAAGCCGGCG AACGTGGCGA GAAAGGAAGG GAAGAAAGCG | 2550 |
| AAAGGAGCGG GCGCTAGGGC GCTGGCAAGT GTAGCGGTCA CGCTGCGCGT | 2600 |

| | |
|---|---|
| AACCACCACA CCCGCCGCGC TTAATGCGCC GCTACAGGGC GCGTACTATG | 2650 |
| GTTGCTTTGA CGTATGCGGT GTGAAATACC GCACAGATGC GTAAGGAGAA | 2700 |
| AATACCGCAT CAGGCGCCAT TCGCCATTCA GGCTGCGCAA CTGTTGGGAA | 2750 |
| GGGCGATCGG TGCGGGCCTC TTCGCTATTA CGCCAGCTGG CGAAAGGGGG | 2800 |
| ATGTGCTGCA AGGCGATTAA GTTGGGTAAC GCCAGGGTTT TCCCAGTCAC | 2850 |
| GACGTTGTAA AACGACGGCC AGTGCCAAGC TTAAGGTGCA CGGCCCACGT | 2900 |
| GGCCACTAGT ACTTCTCGAG CTCTGTACAT GTCCGCGGTC GCGACGTACG | 2950 |
| CGTATCGATG GCGCCAGCTG CAGGCGGCCG CCATATGCAT CCTAGGCCTA | 3000 |
| TTAATATTCC GGAGTATACG TAGCCGGCTA ACGTTAACAA CCGGTACCTC | 3050 |
| TAGAACTATA GCTAGCCAAT TCCATCATCA ATAATATACC TTATTTTGGA | 3100 |
| TTGAAGCCAA TATGATAATG AGGGGGTGGA GTTTGTGACG TGGCGCGGGG | 3150 |
| CGTGGGAACG GGGCGGGTGA CGTAGGTTTT AGGGCGGAGT AACTTGTATG | 3200 |
| TGTTGGGAAT TGTAGTTTTC TTAAAATGGG AAGTTACGTA ACGTGGGAAA | 3250 |
| ACGGAAGTGA CGATTTGAGG AAGTTGTGGG TTTTTTGGCT TTCGTTTCTC | 3300 |
| GGCGTAGGTT CGCGTGCGGT TTTCTGGGTG TTTTTTGTGG ACTTTAACCG | 3350 |
| TTACGTCATT TTTTAGTCCT ATATATACTC GCTCTGCACT TGGCCCTTTT | 3400 |
| TTACACTGTG ACTGATTGAG CTGGTGCCGT GTCGAGTGGT GTTTTTTTAA | 3450 |
| TAGGTTTTCT TTTTTACTGG TAAGGCTGAC TGTTAGGCTG CCGCTGTGAA | 3500 |
| GCGCTGTATG TTGTTCTGGA GCGGGAGGGT GCTATTTTGC CTAGGCAGGA | 3550 |
| GGGTTTTTCA GGTGTTTATG TGTTTTTCTC TCCTATTAAT TTTGTTATAC | 3600 |
| CTCCTATGGG GGCTGTAATG TTGTCTCTAC GCCTGCGGGT ATGTATTCCC | 3650 |
| CCCAAGCTTG CATGCCTGCA GGTCGACTCT AGAGGATCCG AAAAAACCTC | 3700 |
| CCACACCTCC CCCTGAACCT GAAACATAAA ATGAATGCAA TTGTTGTTGT | 3750 |
| TAACTTGTTT ATTGCAGCTT ATAATGGTTA CAAATAAAGC AATAGCATCA | 3800 |
| CAAATTTCAC AAATAAAGCA TTTTTTTCAC TGCATTCTAG TTGTGGTTTG | 3850 |
| TCCAAACTCA TCAATGTATC TTATCATGTC TGGATCCCCC TAGCTTGCCA | 3900 |
| AACCTACAGG TGGGGTCTTT CATTCCCCCC TTTTTCTGGA GACTAAATAA | 3950 |
| AATCTTTTAT TTTATCTATG GCTCGTACTC TATAGGCTTC AGCTGGTGAT | 4000 |
| ATTGTTGAGT CAAAACTAGA GCCTGGACCA CTGATATCCT GTCTTTAACA | 4050 |
| AATTGGACTA ATCGCGGGAT CAGCCAATTC CATGAGCAAA TGTCCCATGT | 4100 |
| CAACATTTAT GCTGCTCTCT AAAGCCTTGT ATCTTGCATC TCTTCTTCTG | 4150 |
| TCTCCTCTTT CAGAGCAGCA ATCTGGGGCT TAGACTTGCA CTTGCTTGAG | 4200 |
| TTCCGGTGGG GAAAGAGCTT CACCCTGTCG GAGGGGCTGA TGGCTTGCCG | 4250 |
| GAAGAGGCTC CTCTCGTTCA GCAGTTTCTG GATGGAATCG TACTGCCGCA | 4300 |
| CTTTGTTCTC TTCTATGACC AAAAATTGTT GGCATTCCAG CATTGCTTCT | 4350 |
| ATCCTGTGTT CACAGAGAAT TACTGTGCAA TCAGCAAATG CTTGTTTTAG | 4400 |
| AGTTCTTCTA ATTATTTGGT ATGTTACTGG ATCCAAATGA GCACTGGGTT | 4450 |
| CATCAAGCAG CAAGATCTTC GCCTTACTGA GAACAGATCT AGCCAAGCAC | 4500 |
| ATCAACTGCT TGTGGCCATG GCTTAGGACA CAGCCCCCAT CCACAAGGAC | 4550 |
| AAAGTCAAGC TTCCCAGGAA ACTGTTCTAT CACAGATCTG AGCCCAACCT | 4600 |

| | |
|---|---|
| CATCTGCAAC TTTCCATATT TCTTGATCAC TCCACTGTTC ATAGGGATCC | 4650 |
| AAGTTTTTTC TAAATGTTCC AGAAAAAATA AATACTTTCT GTGGTATCAC | 4700 |
| TCCAAAGGCT TTCCTCCACT GTTGCAAAGT TATTGAATCC CAAGACACAC | 4750 |
| CATCGATCTG GATTTCTCCT TCAGTGTTCA GTAGTCTCAA AAAAGCTGAT | 4800 |
| AACAAAGTAC TCTTCCCTGA TCCAGTTCTT CCCAAGAGGC CCACCCTCTG | 4850 |
| GCCAGGACTT ATTGAGAAGG AAATGTTCTC TAATATGGCA TTTCCACCTT | 4900 |
| CTGTGTATTT TGCTGTGAGA TCTTTGACAG TCATTTGGCC CCCTGAGGGC | 4950 |
| CAGATGTCAT CTTTCTTCAC GTGTGAATTC TCAATAATCA TAACTTTCGA | 5000 |
| GAGTTGGCCA TTCTTGTATG GTTTGGTTGA CTTGGTAGGT TTACCTTCTG | 5050 |
| TTGGCATGTC AATGAACTTA AAGACTCGGC TCACAGATCG CATCAAGCTA | 5100 |
| TCCACATCTA TGCTGGAGTT TACAGCCCAC TGCAATGTAC TCATGATATT | 5150 |
| CATGGCTAAA GTCAGGATAA TACCAACTCT TCCTTCTCCT TCTCCTGTTG | 5200 |
| TTAAAATGGA AATGAAGGTA ACAGCAATGA AGAAGATGAC AAAAATCATT | 5250 |
| TCTATTCTCA TTTGGAACCA GCGCAGTGTT GACAGGTACA AGAACCAGTT | 5300 |
| GGCAGTATGT AAATTCAGAG CTTTGTGGAA CAGAGTTTCA AAGTAAGGCT | 5350 |
| GCCGTCCGAA GGCACGAAGT GTCCATAGTC CTTTTAAGCT TGTAACAAGA | 5400 |
| TGAGTGAAAA TTGGACTCCT GCCTTCAGAT TCCAGTTGTT TGAGTTGCTG | 5450 |
| TGAGGTTTGG AGGAAATATG CTCTCAACAT AATAAAAGCC ACTATCACTG | 5500 |
| GCACTGTTGC AACAAAGATG TAGGGTTGTA AAACTGCGAC AACTGCTATA | 5550 |
| GCTCCAATCA CAATTAATAA CAACTGGATG AAGTCAAATA TGGTAAGAGG | 5600 |
| CAGAAGGTCA TCCAAAATTG CTATATCTTT GGAGAATCTA TTAAGAATCC | 5650 |
| CACCTGCTTT CAACGTGTTG AGGGTTGACA TAGGTGCTTG AAGAACAGAA | 5700 |
| TGTAACATTT TGTGGTGTAA ATTTTCGAC ACTGTGATTA GAGTATGCAC | 5750 |
| CAGTGGTAGA CCTCTGAAGA ATCCCATAGC AAGCAAAGTG TCGGCTACTC | 5800 |
| CCACGTAAAT GTAAAACACA TAATACGAAC TGGTGCTGGT GATAATCACT | 5850 |
| GCATAGCTGT TATTTCTACT ATGAGTACTA TTCCCTTTGT CTTGAAGAGG | 5900 |
| AGTGTTTCCA AGGAGCCACA GCACAACCAA AGAAGCAGCC ACCTCTGCCA | 5950 |
| GAAAAATTAC TAAGCACCAA ATTAGCACAA AAATTAAGCT CTTGTGGACA | 6000 |
| GTAATATATC GAAGGTATGT GTTCCATGTA GTCACTGCTG GTATGCTCTC | 6050 |
| CATATCATCA AAAAAGCACT CCTTTAAGTC TTCTTCGTTA ATTTCTTCAC | 6100 |
| TTATTTCCAA GCCAGTTTCT TGAGATAACC TTCTTGAATA TATATCCAGT | 6150 |
| TCAGTCAAGT TTGCCTGAGG GGCCAGTGAC ACTTTTCGTG TGGATGCTGT | 6200 |
| TGTCTTTCGG TGAATGTTCT GACCTTGGTT AACTGAGTGT GTCATCAGGT | 6250 |
| TCAGGACAGA CTGCCTCCTT CGTGCCTGAA GCGTGGGGCC AGTGCTGATC | 6300 |
| ACGCTGATGC GAGGCAGTAT CGCCTCTCCC TGCTCAGAAT CTGGTACTAA | 6350 |
| GGACAGCCTT CTCTCTAAAG GCTCATCAGA ATCCTCTTCG ATGCCATTCA | 6400 |
| TTTGTAAGGG AGTCTTTTGC ACAATGGAAA ATTTTCGTAT AGAGTTGATT | 6450 |
| GGATTGAGAA TAGAATTCTT CCTTTTTTCC CCAAACTCTC CAGTCTGTTT | 6500 |
| AAAAGATTGT TTTTTTGTTT CTGTCCAGGA GACAGGAGCA TCTCCTTCTA | 6550 |
| ATGAGAAACG GTGTAAGGTC TCAGTTAGGA TTGAATTTCT TCTTTCTGCA | 6600 |

```
CTAAATTGGT CGAAAGAATC ACATCCCATG AGTTTTGAGC TAAAGTCTGG      6650

CTGTAGATTT TGGAGTTCTG AAAATGTCCC ATAAAAATAG CTGCTACCTT      6700

CATGCAAAAT TAATATTTTG TCAGCTTTCT TTAAATGTTC CATTTTAGAA      6750

GTGACCAAAA TCCTAGTTTT GTTAGCCATC AGTTTACAGA CACAGCTTTC      6800

AAATATTTCT TTTTCTGTTA AAACATCTAG GTATCCAAAA GGAGAGTCTA      6850

ATAAATACAA ATCAGCATCT TTGTATACTG CTCTTGCTAA AGAAATTCTT      6900

GCTCGTTGAC CTCCACTCAG TGTGATTCCA CCTTCTCCAA GAACTATATT      6950

GTCTTTCTCT GCAAACTTGG AGATGTCCTC TTCTAGTTGG CATGCTTTGA      7000

TGACGCTTCT GTATCTATAT TCATCATAGG AAACACCAAA GATGATATTT      7050

TCTTTAATGG TGCCAGGCAT AATCCAGGAA AACTGAGAAC AGAATGAAAT      7100

TCTTCCACTG TGCTTAATTT TACCCTCTGA AGGCTCCAGT TCTCCCATAA      7150

TCATCATTAG AAGTGAAGTC TTGCCTGCTC CAGTGGATCA AGCAACCGCC      7200

AACAACTGTC CTCTTTCTAT CTTGAAATTA ATATCTTTCA GGACAGGAGT      7250

ACCAAGAAGT GAGAAATTAC TGAAGAAGAG GCTGTCATCA CCATTAGAAG      7300

TTTTTCTATT GTTATTGTTT TGTTTTGCTT TCTCAAATAA TTCCCCAAAT      7350

CCCTCCTCCC AGAAGGCTGT TACATTCTCC ATCACTACTT CTGTAGTCGT      7400

TAAGTTATAT TCCAATGTCT TATATTCTTG CTTTTGTAAG AAATCCTGTA      7450

TTTTGTTTAT TGCTCCAAGA GAGTCATACC ATGTTTGTAC AGCCCAGGGA      7500

AATTGCCGAG TGACCGCCAT GCGCAGAACA ATGCAGAATG AGATGGTGGT      7550

GAATATTTTC CGGAGGATGA TTCCTTTGAT TAGTGCATAG GGAAGCACAG      7600

ATAAAAACAC CACAAAGAAC CCTGAGAAGA AGAAGGCTGA GCTATTGAAG      7650

TATCTCACAT AGGCTGCCTT CCGAGTCAGT TTCAGTTCTG TTTGTCTTAA      7700

GTTTTCAATC ATTTTTTCCA TTGCTTCTTC CCAGCAGTAT GCCTTAACAG      7750

ATTGGATGTT CTCGATCATT TCTGAGGTAA TCACAAGTCT TTCACTGATC      7800

TTCCCAGCTC TCTGATCTCT GTACTTCATC ATCATTCTCC CTAGCCCAGC      7850

CTGAAAAAGG GCAAGGACTA TCAGGAAACC AAGTCCACAG AAGGCAGACG      7900

CCTGTAACAA CTCCCAGATT AGCCCCATGA GGAGTGCCAC TTGCAAAGGA      7950

GCGATCCACA CGAAATGTGC CAATGCAAGT CCTTCATCAA ATTTGTTCAG      8000

GTTGTTGGAA AGGAGACTAA CAAGTTGTCC AATACTTATT TTATCTAGAA      8050

CACGGCTTGA CAGCTTTAAA GTCTTCTTAT AAATCAAACT AAACATAGCT      8100

ATTCTCATCT GCATTCCAAT GTGATGAAGG CCAAAAATGG CTGGGTGTAG      8150

GAGCAGTGTC CTCACAATAA AGAGAAGGCA TAAGCCTATG CCTAGATAAA      8200

TCGCGATAGA GCGTTCCTCC TTGTTATCCG GGTCATAGGA AGCTATGATT      8250

CTTCCCAGTA AGAGAGGCTG TACTGCTTTG GTGACTTCCC CTAAATATAA      8300

AAAGATTCCA TAGAACATAA ATCTCCAGAA AAAACATCGC CGAAGGGCAT      8350

TAATGAGTTT AGGATTTTTC TTTGAAGCCA GCTCTCTATC CCATTCTCTT      8400

TCCAATTTTT CAGATAGATT GTCAGCAGAA TCAACAGAAG GGATTTGGTA      8450

TATGTCTGAC AATTCCAGGC GCTGTCTGTA TCCTTTCCTC AAAATTGGTC      8500

TGGTCCAGCT GAAAAAAAGT TTGGAGACAA CGCTGGCCTT TTCCAGAGGC      8550

GACCTCTGCA TGGTCTCTCG GGCGCTGGGG TCCCTGCTAG GGCCGTCTGG      8600
```

| | |
|---|---|
| GCTCAAGCTC CTAATGCCAA AGGAATTCCT GCAGCCCGGG GGATCCACTA | 8650 |
| GTTCTAGAGC GGCCGCCACC GCGGTGGCTG ATCCCGCTCC CGCCCGCCGC | 8700 |
| GCGCTTCGCT TTTTATAGGG CCGCCGCCGC CGCCGCCTCG CCATAAAAGG | 8750 |
| AAACTTTCGG AGCGCGCCGC TCTGATTGGC TGCCGCCGCA CCTCTCCGCC | 8800 |
| TCGCCCCGCC CCGCCCCTCG CCCCGCCCCG CCCCGCCTGG CGCGCGCCCC | 8850 |
| CCCCCCCCCC CCGCCCCCAT CGCTGCACAA AATAATTAAA AAATAAATAA | 8900 |
| ATACAAAATT GGGGGTGGGG AGGGGGGGGA GATGGGGAGA GTGAAGCAGA | 8950 |
| ACGTGGCCTC GAGTAGATGT ACTGCCAAGT AGGAAAGTCC CATAAGGTCA | 9000 |
| TGTACTGGGC ATAATGCCAG GCGGGCCATT TACCGTCATT GACGTCAATA | 9050 |
| GGGGGCGTAC TTGGCATATG ATACACTTGA TGTACTGCCA AGTGGGCAGT | 9100 |
| TTACCGTAAA TACTCCACCC ATTGACGTCA ATGGAAAGTC CCTATTGGCG | 9150 |
| TTACTATGGG AACATACGTC ATTATTGACG TCAATGGGCG GGGGTCGTTG | 9200 |
| GGCGGTCAGC CAGGCGGGCC ATTTACCGTA AGTTATGTAA CGACCTGCAG | 9250 |
| GCTGATCTCC CTAGACAAAT ATTACGCGCT ATGAGTAACA CAAAATTATT | 9300 |
| CAGATTTCAC TTCCTCTTAT TCAGTTTTCC CGCGAAAATG GCCAAATCTT | 9350 |
| ACTCGGTTAC GCCCAAATTT ACTACAACAT CCGCCTAAAA CCGCGCGAAA | 9400 |
| ATTGTCACTT CCTGTGTACA CCGGCGCACA CCAAAAACGT CACTTTTGCC | 9450 |
| ACATCCGTCG CTTACATGTG TTCCGCCACA CTTGCAACAT CACACTTCCG | 9500 |
| CCACACTACT ACGTCACCCG CCCCGTTCCC ACGCCCGCG CCACGTCACA | 9550 |
| AACTCCACCC CCTCATTATC ATATTGGCTT CAATCCAAAA TAAGGTATAT | 9600 |
| TATTGATGAT GCTAGCATGC GCAAATTTAA AGCGCTGATA TCGATCGCGC | 9650 |
| GCAGATCTGT CATGATGATC ATTGCAATTG GATCCATATA TAGGGCCCGG | 9700 |
| GTTATAATTA CCTCAGGTCG ACGTCCCATG GCCATTCGAA TTCGTAATCA | 9750 |
| TGGTCATAGC TGTTTCCTGT GTGAAATTGT TATCCGCTCA CAATTCCACA | 9800 |
| CAACATACGA GCCGGAAGCA TAAAGTGTAA AGCCTGGGGT GCCTAATGAG | 9850 |
| TGAGCTAACT CACATTAATT GCGTTGCGCT CACTGCCCGC TTTCCAGTCG | 9900 |
| GGAAACCTGT CGTGCCAGCT GCATTAATGA ATCGGCCAAC GCGCGGGGAG | 9950 |
| AGGCGGTTTG CGTATTGGGC GC | 9972 |

(2) INFORMATION FOR SEQ ID NO:4:

(i) SEQUENCE CHARACTERISTICS:
        (A) LENGTH: 14 base pairs
        (B) TYPE: nucleic acid
        (C) STRANDEDNESS: double
        (D) TOPOLOGY: unknown (ii) MOLECULE TYPE: DNA (genomic)

(xi) SEQUENCE DESCRIPTION: SEQ ID NO:4:

| | |
|---|---|
| TAGTAAATTT GGGC | 14 |

(2) INFORMATION FOR SEQ ID NO:5:

(i) SEQUENCE CHARACTERISTICS:
        (A) LENGTH: 14 base pairs
        (B) TYPE: nucleic acid
        (C) STRANDEDNESS: double
        (D) TOPOLOGY: unknown

```
      (ii) MOLECULE TYPE: DNA (genomic)

(xi) SEQUENCE DESCRIPTION: SEQ ID NO:5:

AGTAAGATTT GGCC                                                          14

(2) INFORMATION FOR SEQ ID NO:6:

(i) SEQUENCE CHARACTERISTICS:
          (A) LENGTH: 14 base pairs
          (B) TYPE: nucleic acid
          (C) STRANDEDNESS: double
          (D) TOPOLOGY: unknown (ii) MOLECULE TYPE: DNA (genomic)

(xi) SEQUENCE DESCRIPTION: SEQ ID NO:6:

AGTGAAATCT GAAT                                                          14

(2) INFORMATION FOR SEQ ID NO:7:

(i) SEQUENCE CHARACTERISTICS:
          (A) LENGTH: 14 base pairs
          (B) TYPE: nucleic acid
          (C) STRANDEDNESS: double
          (D) TOPOLOGY: unknown (ii) MOLECULE TYPE: DNA (genomic)

(xi) SEQUENCE DESCRIPTION: SEQ ID NO:7:

GAATAATTTT GTGT                                                          14

(2) INFORMATION FOR SEQ ID NO:8:

(i) SEQUENCE CHARACTERISTICS:
          (A) LENGTH: 14 base pairs
          (B) TYPE: nucleic acid
          (C) STRANDEDNESS: double
          (D) TOPOLOGY: unknown (ii) MOLECULE TYPE: DNA (genomic)

(xi) SEQUENCE DESCRIPTION: SEQ ID NO:8:

CGTAATATTT GTCT                                                          14

(2) INFORMATION FOR SEQ ID NO:9:

(i) SEQUENCE CHARACTERISTICS:
          (A) LENGTH: 8 base pairs
          (B) TYPE: nucleic acid
          (C) STRANDEDNESS: double
          (D) TOPOLOGY: unknown (ii) MOLECULE TYPE: DNA (genomic)

(xi) SEQUENCE DESCRIPTION: SEQ ID NO:9:

WANWTTTG                                                                  8

(2) INFORMATION FOR SEQ ID NO:10:

(i) SEQUENCE CHARACTERISTICS:
          (A) LENGTH: 19307 base pairs
          (B) TYPE: nucleic acid
          (C) STRANDEDNESS: double
          (D) TOPOLOGY: unknown (ii) MOLECULE TYPE: cDNA (xi) SEQUENCE DESCRIPTION: SEQ ID NO:10:

CCAATTCCAT CATCAATAAT ATACCTTATT TTGGATTGAA GCCAATATGA                     50
```

```
TAATGAGGGG GTGGAGTTTG TGACGTGGCG CGGGGCGTGG GAACGGGGCG         100

GGTGACGTAG GTTTTAGGGC GGAGTAACTT GTATGTGTTG GGAATTGTAG         150

TTTTCTTAAA ATGGGAAGTT ACGTAACGTG GGAAAACGGA AGTGACGATT         200

TGAGGAAGTT GTGGGTTTTT TGGCTTTCGT TTCTGGGCGT AGGTTCGCGT         250

GCGGTTTTCT GGGTGTTTTT TGTGGACTTT AACCGTTACG TCATTTTTTA         300

GTCCTATATA TACTCGCTCT GCACTTGGCC CTTTTTTACA CTGTGACTGA         350

TTGAGCTGGT GCCGTGTCGA GTGGTGTTTT TTTAATAGGT TTTCTTTTTT         400

ACTGGTAAGG CTGACTGTTA GGCTGCCGCT GTGAAGCGCT GTATGTTGTT         450

CTGGAGCGGG AGGGTGCTAT TTTGCCTAGG CAGGAGGGTT TTTCAGGTGT         500

TTATGTGTTT TTCTCTCCTA TTAATTTTGT TATACCTCCT ATGGGGCTG          550

TAATGTTGTC TCTACGCCTG CGGGTATGTA TTCCCCCCAA GCTTGCATGC         600

CTGCAGGTCG ACTCTAGAGG ATCCGAAAAA ACCTCCCACA CCTCCCCCTG         650

AACCTGAAAC ATAAAATGAA TGCAATTGTT GTTGTTAACT TGTTTATTGC         700

AGCTTATAAT GGTTACAAAT AAAGCAATAG CATCACAAAT TTCACAAATA         750

AAGCATTTTT TTCACTGCAT TCTAGTTGTG GTTTGTCCAA ACTCATCAAT         800

GTATCTTATC ATGTCTGGAT CCCCGCGGCC GCTCTAGAAC TAGTGGATCC         850

CCCGGGCTGC AGGAATTCCG TAACATAACT GCGTGCTTTA TTGAGATACA         900

CAGTAAAGCA GTAATATAAT ACAATAGTAA GGCATATATT TGGTGAAATC         950

TGATATGTTG TGAAAATGCA GTAAAACTGA AGTTTAAAAA AATAATTAGT        1000

AAATGTTACA GTGTTGGTGT TAAAACACAA TCTATTATGA TACTCAAGTA        1050

AGAGTCCAGT ACCTGGAGAC AATGATGATA CATGCCATGT GATGATTATG        1100

CTTCAGTTAC ACTGATTATG ATTTACACTT TAATACTTGA TGGTTATAAA        1150

GAACATGAAA TGATGTCCAA ATTATGCTTA AAATCAGCAA TAAAGCTCTC        1200

AGTTTTTATT CAAATATTTT GATAGATTCA CTCCAGAACT AATATCTAAA        1250

AGATAAAACG AAAAGATTAA AACAAAACTA TGCACTCTAT CTACCTTGGA        1300

TTTTAGAATG AAACTTAAAA CTTCTTAGTA GGAAAGGAAC CCCTTGTTTT        1350

AAATCTTGGT GAAAACAAAT CCTTGGATAA AGAAAATGCC CAGTGCCACA        1400

TAAGGAGAG AGAGAGAGAA AAGCAAGACC AGAACCAAAT TTCAATTTGT         1450

TATCTTAGAG CTTTGGGTTT TCTTTTGAA ATTATAAATG AAAAAAGGAA         1500

ACTGGTGTCC ACACAACAGA CAAGTGGTGA AGTTGTGAAA TTAGGTGTGC        1550

ACAATTACTA GAAACACCCC AAAACCAAAG TGAGGTAGAA ATAGCATGAG        1600

AAGCTGTGTT TGATGTTAAT TACAATTAAT AATGGACAAA ACCCACTCGC        1650

TAGAAGTTAA TTACACTTGA CGTTAGAGGT AACAGATTTG CAAAATGATA        1700

GGACAGTGAT TTCTATTGAG AGAATGCTCT TTAAATGCTA AGAAGAAGAA        1750

ACTGGCATGA GAGGAGTAAA GCTCTTCCTA GCAGTCCTTA GCTTTCTGTT        1800

GCACTTTTTC TCCTGGTTCA ATGACTTGCA TTTGTTTAGA CATTTCAGCC        1850

CGTCAACTAG ACCAGAGAGT TTGGAGACGC TTTTGCTCTC AAAACTTTCC        1900

AACCACTGTG CCTTCTCACC CACAATCCTG TGTGGAGTTA CTTGCAGGGA        1950

AACCAATGCA AAGGAGACAA ATGCAGTTCA TGGGCTTCTG GACTGATATT        2000

CACCAGGGTC ACAATGTGAT TGGGTTACTT TCTTAACAGT AATCCTAAGT        2050
```

```
CTTGCAGCAT TAAAAAAAAA AATCATCACA ATGAAGAAAA AAAAACCCAA      2100

AAAATCTAAA ATCTAAAATT CATCATCATC ATCAACAACA ACAACAACAA      2150

CAACAACAAA ACCACCCACT TCAGGTTGAG TTTATGAAGA GGGCAGAACA      2200

ATTTAGTTGT AATTATAGAG ATGTTTATAT GTATAGTTGT AAATATTCAT      2250

CCATTCTTTT ACAGAGTTGT TGCTCCCCTC ATATAAATTG ACTGAGGAGC      2300

CGCAACCTTT AGCTCCTACC ATCTTCCTCC TACTGTCTGG GAGTTAAAAA      2350

TGTCATCTGA TGTTCTATTG CAGAAACATC ATTAAATATA ACCCAACAGT      2400

AGGAAGTTGA ATATATCAGC CAACAAATTA CTATGATAGT AAGTCCTGTG      2450

TATTCATTCG CATGTTCCTT GAAAAAAATG AATCCTCTAG CTCTCAGTGG      2500

AAAGTTTAAA ACTAGAAACA TCTGGAGCCC TAGACAATAT TTTAGTGTGG      2550

CGGTAGTCTC CTGGCTTTGG GCTCCAGGGA AAATTCACTC TTGCCCAAGC      2600

AGATAAGCCC AGATGACTAG AAGCAATTTC CATTAGGAAG TGGCAAGAAC      2650

ATTTGAAGAA GTAACTTCAT ATCTATTTAT CTATATACCT ATAGTATTTA      2700

TATACTTGTA GACATATAGA TGTATAAAAT GAAAGCCCAT AGCCAGCCCC      2750

ACTCAGTCAA CAATTCTCAA AAGAGCAATA TGAAGCAGTC ATTTGGTGGG      2800

GTTCGTATGC AAGAAAATAA AAAAACGTCA TGAATTCCAT ATGAATACCA      2850

CGCTAAAGTA ATGCAAAACA ATGTGCTGCC TCAGTGTGTG TGTGTGTGTG      2900

TGTGTGTGTG GTGGGTTCGT GCATGTATGT GTGCGTGTGT GTGTGTGTGT      2950

GTGTGTGTGT GTGTGTGTGC GTGTGTGTTT GTTTAGGGGT TTTTATAAAC      3000

AACTTTTTTT ATAAAGCACA CTTTAGTTTA CAATCTCTCT TTATAACTGT      3050

TATAAATTTT TAAACAACCC AAAATGCGTT CCATATAAAG AAATGGCAAG      3100

TTATTTAGCT ATCAAGATTT TACATGTTTT CTTTTAACTT TTTTGTACAA      3150

TTGCATAGAC GTGTAAAACC TGCCATTGTT AACAAAACAA TAACAGACTT      3200

AGAAACTACT GAAATCTACA GTATAGTACC ACTACCCTTC ACAAAAATAT      3250

AGATTTTATT TCTTGTAAAC TCTTACTGTC TAATCCTCTT TGTTGTACGA      3300

ATATTATAAA AACCATGCGG GAATCAGGAG TTGTAAAACA TTTATTCTGC      3350

TCCTTCTTCA TCTGTCATGA CTGAAACTAA GGACTCCATC GCTCTGCCCA      3400

AATCATCTGC CATGTGGAAA AGGCTTCCTA CATTGTGTCC TCTCTCATTG      3450

GCTTTCCGGG GGCATTTCTT CCTCTTGAAC TAGGGAAGGA GTTGTTGAGT      3500

TGCTCCATCA CTTCTTCTAA CCCTGTGCTT GTGTCCTGGG GAGGACTCAG      3550

AAGATCTTCC TCACCCATAG ATTCTGAAGT TTGACTGCCA ACCACTCGGA      3600

GCAGCATAGG CTGACTGCTA TCTGACCTCT GCAGAGAGGT GGAAGGAGAG      3650

GACACCGTGG TGCCATTCAC CTTAGCTTCA GCCTGGGGCT GCTCCAGGAG      3700

CTGTCTCAGT CTATGTAACT GAGACTCCAG CTGTTTATTG TGGTCTTCCA      3750

GGATTTGCAT CCTGGCTTCC AGGCGTCCTT TGTGTTGGCG CAGTAGCTTA      3800

GCCTCAGCAA TGAGCTCAGC ATCCCTGGGA CTCTGAGGAG AGGTGGGCAT      3850

CATCTCAGGA GGAGATGGCA GTGGAGACAG GCCTTTATGC TCATGCTGCT      3900

GCTTCAGGCG ATCATATTCT GCTTGCAGAT TCCTGTTTTC TTCCTCAAGA      3950

TCTGCTAGGA TTCTCTCTAG CTCCCCTCTT TCCTCACTCT CTAAGGAAAT      4000

CAAGATCTGG GCAGGACTAC GAGGCTGGCT CAGGGGGGAG TCCTGGTTCA      4050
```

```
AACTTTGGCA GTAATGCTGG ATTAACAAAT GTTCATCATC TATGCTCTCA        4100

TTAGGAGAGA TGCTATCATT TAGATAAGAT CCATTGCTGT TTTCCATTTC        4150

TGCTAGCCTG CTAGCATAAT GTTCAATGCG TGAATGAGTA TCATCGTGTG        4200

AAAGCTGGGG GGACGAGGCA GGCGCAGAAT CTACTGGCCA GAAGTTGATC        4250

AGAGTAACGG GAGTTTCCAT GTTGTCCCCC TCTAACACAG TCTGCACTGG        4300

CAGGTAGCCC ATTCGGGGAT GCTTCGCAAA ATACCTTTTG GTTCGAAATT        4350

TGTTTTTTAG TACCTTGGCG AAGTCGCGAA CATCTTCTCC GGATGTAGTC        4400

GGAGTGCAAT ACTCTACCAT GGGGTAGTGC ATTTTATGGC CCTTTGCAAC        4450

TCGGCCAGAA AAAAGCAAC  TTTGGCAGAT GTCATAATTA AAATGCTTTA        4500

GGCTTCTGTA CCTGAATCCA ATGATTGGAC ACTCCTTACA GATGTTACAC        4550

TTGGCTTGAT GCTTGGCAGT TTCAGCAGCA GCCACTCTGT GCAAGACGGG        4600

CAGCCACACC ATAGACTGGG GTTCCAGGCG CATCCAGTCA AGGAAGAGAG        4650

CAGCTTCAAT CTCAGGTTTA TTATTGGCAA ATTGGAAGCA GCTCCTGACA        4700

CTCGGCTCAA TGTTACTGCC CCCAAAGGAA GCAACTTCAC CCAACTGTCT        4750

TGGGATTTGA ATAGAATCAT GCAGAAGAAG ACCCAGCCTA CGCTGGTCAC        4800

AAAAGCCAGT TGAACTTGCC ACTTGCTTGA AAAGGTATCT GTACTTGTCT        4850

TCCAAGTGTG CTTTACACAG AGAAATGATG CCAGTTTTAA AAGACAGGAC        4900

ACGGATCCTC CCTGTTCGTC CCGTATCATA AACATTGAGA AGCCAGTTGA        4950

GACACATATC CACACAGAGA GGGACATTGA CCAGATTGTT GTGCTCTTGC        5000

TCCAGACGAT CATAAATTGT AGTCAAACAG TTAATTATCT GCAGGATATC        5050

CATGGGCTGG TCATTTTGCT TGAGGTTGTG CTGGTCCAGG GCATCACATG        5100

CAGCTGACAG GCTCAAGAGA TCCAAGCAAA GGGCCTTCTG GAGCCTTCTG        5150

AGCTTCATGG CAGTCCTATA CGCGGAGAAC CTGACATTAT TCAGGTCAGC        5200

TAAAGACTGG TAGAGCTCTG TCATTTTGGG GTGGTCCCAA CAAGTGGTTT        5250

GGGTCTCGTG GTTGATATAG TAGGGCACTT TGTTTGGTGA GATGGCTCTC        5300

TCCCAGGGAC CCTGAACTGA AGTGGAAAGG AAGTGCTGGG ATGCAGGACC        5350

AAAGTCCCTG TGGGCTTCAT GCAGCTGTCT GACACGGTCC TCCACAGCCA        5400

CCTGTAGAAG CCTCCATCTG GTATTCAGAT CTTCCAAAGT GCTGAGGTTA        5450

TAAGGTGAGA GCTGAATGCC CAGTGTGGTC AGCTGATGTG CAAGGTCATT        5500

GACACGATTG ACATTCTCTT TAAGAGGTGC AATTTCTCCC CGAAGTGCCT        5550

TGACTTTTTC AAGGTGATCT TGCAGAGAGT CAATGAGGAG ATCCCCCACT        5600

GGCTGCCAGG ATCCCTTGAT CACCTCAGCT TGGCGCAACT TGAGGTCCAG        5650

TTCATCGGCA GCTTCCTGAA GTTCCTGGAG TCTTTCAAGA GCTTCATCTA        5700

TTTTTCTCTG CCAATCAGCT GAGCGCAGGT TCAATTTGTC CCATTCAGCG        5750

TTGACCTCTT CAGCCTGCTT TCGTAGGAGC CGAGTGACAT TCTGAGCTCT        5800

TTCTTCAGGA GGCAGTTCTC TGGGCTCCTG GTAGAGTTTC TCTAGTCCTT        5850

CCAAAGGCTG CTCTGTCAGA AATATTCTCA CAGTCTCCAG AGTACTCATG        5900

ATTACAGGTT CTTTAGTTTT CAATTCCCTC TTGAAGGCCC TATGTATATC        5950

ATTCTGCTTC TGAACTGCTG GGAAATCACC ACCGATGGGT GCCTGACGGC        6000

TCAGTTCATC ATCTTTCAGC TGTAGCCAAA CAAGAAGTTC CTGAAGAGAA        6050
```

| | |
|---|---|
| AGATGCAAAC GCTTCCACTG GTCAGAACTT GCTTCCAAAT GGGACCTAAT | 6100 |
| GTTGAGAGAC TTTTTCTGAA GTTCACTCCA CTTGAAATTC ATGTTATCCA | 6150 |
| AACGTCTTTG TAACAGGGGT GCTTCATCCG AACCTTCCAG GGATCTCAGG | 6200 |
| ATTTTTTGGC CATTTTCATC AAGATTGTGA TAGATATCTG TGTGAGTTTC | 6250 |
| AATTTCTCCT TGGAGATCTT GCCATGGTTT CATCAGCTCT CTGACTCCCC | 6300 |
| TGGAGTCTTC TAGGAGCTTC TCCTTACGGG AAGCGTCCTG TAGGACATTG | 6350 |
| GCAGTTGTTT CTGCTTCCGT AATCCAGGAA AGAAACTTCT CCAGGTCCAG | 6400 |
| AGGGAACTGC TGCAGTAATC TATGAGTTTC TTCCAAAGCA GCCTCTTGCT | 6450 |
| CACTTACTCT TTTATGAATG TTTCCCCAAG AAGTATTGAT ATTCTCTGTT | 6500 |
| ATCATGTGTA CTTTTCTGGT ATCATCAGCA GAATAGTCCC GAAGAAGTTT | 6550 |
| CAGTGCCAAA TCATTTGCCA CGTCTACACT TATCTGCCGT TGACGGAGGT | 6600 |
| CTTTGGCCAA CTGCTTGGTT TCTGTGATCT TCTTTTGGAT TGCATCTACT | 6650 |
| GTGTGAGGAC CTTCTTTCCA TGAGTCAAGC TTGCCTCTGA CCTGTCCTAT | 6700 |
| GACCTGTTCG GCTTCTTCCT TAGCTTCCAG CCATTGTGTT GAATCCTTTA | 6750 |
| ACATTTCATT CAACTGTTGT CTCCTGTTCT GCAGCTGTTC TTGAACCTCA | 6800 |
| TCCCACTGAA TCTGAATTCT TTCAATTCGA TCAGTAATGA TTGTTCTAGC | 6850 |
| TTCTTGATTG CTGGTTTTGT TTTTCAAATT CTGGGCAGCA GTAATGAGTT | 6900 |
| CTTCCAATTG GGGGCGTCTC TGTTCCAAAT CTTGCAGTGT TGCCTTCTGT | 6950 |
| TTGATGATCA TTTCATTGAT GTCTTCCAGA TCACCCACCA TCACTCTCTG | 7000 |
| TGATTTTATA ACTCGATCAA GCAGAGACAG CCAGTCTGTA AGTTCTGTCC | 7050 |
| AAGCTCGGTT GAAGTCTGCC AGTGCAGGTA CCTCCAACAG CAAAGAAGAT | 7100 |
| GGCATTTCTA GTTTGGAGAT GACAGTTTCC TTAGTAACCA CAGATTGTGT | 7150 |
| CACTAGAGTA ACAGTCTGAC TGGCAGAGGC TCCAGTAGTG CTCAGTCCAG | 7200 |
| GGGCACGGTC AGGCTGCTTT GTCCTCAGCT CCCGAAGTAA ATGGTTTACA | 7250 |
| GCCTCCCACT CAGACCTCAG ATCTTCTAAC TTCCTCTTCA CTGGCTGAGT | 7300 |
| GCTTGGTTTT TCCTTATACA AATGCTGCCC TTTCGACAAA AGCCTTTCCA | 7350 |
| CATCCGCTTG TTTACCGTGA ACTGTTACTT CAATCTCCTT TATGTCAAAC | 7400 |
| GGTCCTGCCT GACTTGGTTG GTTATAAATT TCCAACTGGT TTCTAATAGG | 7450 |
| AGAGACCCAC AGAAGCAGGT GATCCAGCTG CTCTTCAAGC TGCCTAAAAT | 7500 |
| CTTTTAAGTG AACCTCAAGC TCTCCTTGTT TCTCAGGTAA AGCTCTGGAG | 7550 |
| ACCTTTATCC ACTGGAGATT TGTCTGTTTG AGCTTCTTTT CAAGTTTATC | 7600 |
| TTGCTCTTCT GGCCTTATGG GAGCACTTAC AAGTACTGCT CCTCCTGTTT | 7650 |
| CATTTAATTG TTTTAGAATT CCCTGGCGCA GGGGCAACTC TTCTGCCAGT | 7700 |
| AACTTGACTT GTTCAAGTTG TTCTTTTAGC TGCTGCTCAT CTCCAAGTGG | 7750 |
| AGTAATAGCA ATGTTATCTG CTTCTTCCAG CCACAAAACA AATTCATTTA | 7800 |
| AATCTCTTTG AAATTCTGAC AAGACATTCT TTTGTTCTTC AATCCTCTTT | 7850 |
| CTCCTTTCTG CCAGCTCTTT GCAGATGTCG TGCCACCGCA GACTCAAGCT | 7900 |
| TCCTAATTTT TCTTGTAGAA TATTGACATC TGTTTTTGAA GACTGTTGAA | 7950 |
| TTATTTCTTC CCCAGTTGCA TTCAGTGTTC TGACAACAGC TTGACGCTGC | 8000 |
| CCAATGCCAT CCTGGAGTTC CTTAAGATAC CATTTGTATT TAGCATGTTC | 8050 |

```
CCAGTTTTCA GGATTTTGTG TCTTTTTGAA AAACTGTTCA ACTTCATTCA      8100

GCCATTGATT AAATACCTTC ATATCATAAT GAAAGTGTCG CCATTTTTCA      8150

ACTGATCTGT CGAATCGCCC TTGTCGTTCC TTGTACATTC TATGAAGTTT      8200

TTCCCCCTGG AAATCCATCT GTGCCACGGC TTCCTGTACT TTCACCTTTT      8250

CCATGGAGGT GGCACTTTGC AAGGCTGCTG TCTTCTTCTT GTGAATAATA      8300

TCAATCCGAC CTGAGATTTG TTGCAAATTG TCTTTTATAT TCTTAAGAGA      8350

CTCCTCTTGC TTAAAAAGAT CTTCAAAATC TTTAGCACAG AGTTCAGGAG      8400

TATTTAGAAG ATGATCAACT TCTGAAAGAG CTTGTAAGAT ATGACTGATC      8450

TCGGTCAAAT AAGTAGAAGG CACATAAGAA ACATCCAAAG GCATATCTTC      8500

AGTCGTCACT ACCATAGTTT CTTCATGGAG AGTGTGAATT TGTGCAAAGT      8550

TGAGTCTTCG AAACTGAGCA AAATTGCTCT CAATTTGCCG CCAGCGCTTG      8600

CTGAGCTGGA TCTGAGTTGG CTCCACTGCC ATTGCGGCCC CATTCTCAGA      8650

CAAGCCCTCA GCTTGCCTGC GCACTGCATT CAGCTCCTCT TTCTTCTTCT      8700

GCAATTCACG ATCAATTTCC TTTAATTTTC TTTCATCTCT GGGTTCAGGT      8750

AGGCTGGCTA ATTTTTTTTC AATTTCATCC AAGCATTTCA GGAGATCATC      8800

AGCCTGCCTC TTGTACTGAT ACCACTGGTG AGAAATTTCT AGGGCCTTTT      8850

TTCTTCTTTG AGACCTCAAA TCCTTGAGAG CATTATGTTT TGTCTGTAAC      8900

AGCTGCTGTT TTATCTTTAT TTCCTCTCGC TTTCTCTCAT CTGTGATTCT      8950

TTGTTGTAAG TTGTCTCCTC TTTGCAACAA TTCATTTACA GTACCCTCAT      9000

TGTCTTCACT CATATCTTTA TTGAAGTCTT CCTCTTTCAG ATTCACCCCC      9050

TGCTGAATTT CAGCCTCCAG TGGTTCAAGC AATTTTTGTA TATCTGAGTT      9100

AAACTGCTCC AATTCCTTCA AAGGAATGGA GGCCTTTCCA GTCTTAATTC      9150

TGTGAGAAAT AGCTGCAAAT CGACGGTTGA GCTCAGAGAT TTGGGGCTCT      9200

ACTACTTTCC TGCAGTGGTC ACCGCGGTTT GCCATCAATT TTGCTGCTTG      9250

GTCACGTGTG GAGTCCACCT TTGGGCGCAT GTCATTCATT TCAGCCTTTA      9300

AACGCTTAAG AATGTCTTCC TTTTGTTGTG GTTTCTTCTT TTCAGACTCA      9350

TCTAAAAGTT CATCTGCATG AATGATCCAC TTTGTGATTT GTTCTATGTT      9400

CTGATCAAAG GTTCCATGT GTTTCTGGTA TTCCAACAAA AGATTTAGCC       9450

ATTCTTCTAC TCTGGAGGTG ACAGCTATCC AGTTACTGTT CAGAAGACTC      9500

AGTTTATCTT CTACCAAGGT TTCTTTCTTG CCCAACACCA TTTTCAAAGA      9550

CTCTCCTAAT TCTGTAACAC TCTTCAAGTG AGCCTTCTGT TTCTCAATCT      9600

CTTTTTGAGT AGCCTTTCCC CAGGCAACTT CAGAATCCAA ATTACTTGGC      9650

ATTCCTTCAA CTGCTGATCT CTTCGTCAAT TCTGTATCTG TTGCTGCCAG      9700

CCATTCTGTT AAGACATTCA TTTCCTTTCT CATCTTACGG GACAACTTCA      9750

AGCATTTCTC CAACTGTTGC TTTCTCTCTG TTACCTTCGC ACCCAACTCA      9800

TTGTAATGCA ATTTCAAAGC TGTTACTCGT TCATCAAGCT CTTTGGGATT      9850

TTCTGTCTGC TTTTTCTGTA CAATTTGACG TCCGGTTTTA ATCACCATTT      9900

CCACTTCAGA CTTGACTTCA CTCAGGCTTT TATACAAGTT CACACAATGA      9950

CTTAGTTGTG ACTGAATTAC TTCCTGTTCA ACACTCTTGG TTTCCAATGC      10000

AGGCAAATGC ATCTTGACTT CATCTAAAAT CATCTTACTT TCCTCTAGAC      10050
```

```
GTTGTTCAAA ATTGGCTGGT TTTTGGAATA ATCGAAATTT CATGGAGACA        10100

TCTTGTAATT TTTTCTGTGC AACATCAATT TGTGAAAGAA CCCTTTGGTT        10150

GGCATCCTTC CCCTGGTTAT GTTTCTTCAT TTCTTCTAAA CTTATCTCAT        10200

GACTTGTCAA ATCTGATTGG ATTTTCTGGG CTTCCTGAGG CATTTGAGCT        10250

GCATCCACCT TGTCAGTGAT ATAAGCTGCC AACTGCTTGT CAATGAATTC        10300

AAGCGACTCC TGAATTAAGT GCAAGGACTT TTCAATTTCC TGGGCAGACT        10350

GGATACTCTG TTCAAGCAAC TTTTGTTTCC TCACAGCCTC TTCATGTAGT        10400

TCCCTCCAAC GAGAATTAAA CGTCTCAAGC TCCTCATTGA TCAGTTCATC        10450

CATGACTCCT CCATCTGTAA GAGTCTGTGC CAATAGACGA ATCTGATTTG        10500

GGTTCTCCTC TGAATGATGC ATCAGATTTT CAAGAGATTC TAGCACTTCA        10550

GTGATTTCCT CAGGTCCTGC AGGAACATTT TCCATGGTTT TAAGTTTCAA        10600

TTCTACTTCA TTGAGCCACT TGTTTGCTTT CTCTAAATAT GACAATAACT        10650

CATGCCAACA TGCCCAAACT TCTTCCAAAG TTTTGCATTT TCCATTCAGC        10700

CTGGTGCACA GCCATTGGTA GTTGGTGGTC AGAGTTTCAA GTTCCTTTTT        10750

TAAGGCCTCT TGTGCTGAGG GTGGAGCGTG AGCTATTACA CTATTTACAG        10800

TCTCAGTAAG GAGTTTCACT TTAGTTTCTT TTTGTAGTGC CTCTTCTTTA        10850

GCTCTCTTCA TTTCTTCAAC AGCAGTCTGT AATTCATCTG GAGTTTTATA        10900

TTCAAAATCT CTCTCTAGAT ATTCTTCTTC AGCTTGTGTC ATCCACTCAT        10950

GCATCTCTGA TAGATCTTTT TGGAGGCTTA CGGTTTTATC CAAACCTGCC        11000

TTTAAGGCTT CCTTTCTGGT GTAGACCTGG CGGCATATGT GATCCCACTG        11050

AGTGTTAAGC TCTCTAAGTT CTGTCTCCAG TCTGGATGCA AACTCAAGTT        11100

CAGCTTCACT CTTTATCTTC TGCCCACCTT CATTAACACT ATTTAAACTG        11150

GGCTGAATTG TTTGAATATC ACCAACTAAA AGTCTGCATT GTTGAGCTG         11200

TTTTTTCAGG ATTTCAGCAT CCCCCAGGGC AGGCCATTCC TCTTTCAGGA        11250

AAACATCAAC TTCAGCCATC CATTTCTGTA AGGTTTTTAT GTGATTCTGA        11300

AATTTTCGAA GTTATTCAT ATGTTCTTCT AGCTTTTGGC AGCTTTCCAC         11350

CAACTGGGAG GAAAGTTTCT TCCAGTGCCC CTCAATCTCT TCAAATTCTG        11400

ACAGATATTT CTGGCATATT TCTGAAGGTG CTTTCTTGGC CATCTCCTTC        11450

ACAGTGTCAC TCAGATAGTT GAAGCCATTT TGTTGCTCTT TCAAAGAACT        11500

TTGCAGAGCC TGTAATTTCC CGAGTCTCTC CTCCATTATT TCATATTCAG        11550

TAACACTAAG ATAAGGTACA GAGAGTTTGC TTTCTGACTG CTGGATCCAC        11600

GTCCTGATGC TACTCATTGT CTCCTGATAG CGCATTGGTG GTAAAGTGTC        11650

AAAAATTGTC TGTAGCTCTT TCTCTTTGGC CCTCACACCA TCAAAGATGT        11700

GGTTAAAATG ATTAGTAAAG GCCACAAAGT CTGCATCCAG AAACATTGGC        11750

CCCTGTCCCT TTTCTTTCAG TTGTAGACTC TGAATTTTTA ATTGCTCAAT        11800

TTGAGGCTGA AGAGCTGACA ATCTGTTGAC TTCATCCTTA CAAATTTTTA        11850

ACTGGCTTTT AATTGCTGTT GGCTCTGATA GGGTGGTAGA CTGGGTTTTC        11900

AACAAGTTTT CGGCAGTAGT TGTCATCTGT TCCAATTGTT GTAGCTGATT        11950

ATAAAAGGTA ATGATGTTGG TTTGATACTC TAGCCAGTTA ACTCTCTCAC        12000

TCAGCAATTG GCAGAATTCT GTCCACCGGC TGTTCAGTTG TTCTGAAGCT        12050
```

```
TGTCTGATAC TTTCAGCATT AACACCCTCA TTTGCCATCT GTTCCACCAG        12100

GGCCTGAGCT GATCTGCTGG CATCTTGCAG TTTTCTGAAC TTCTCTGCTT        12150

TTTCTCGTGC TATGGCATTG ACTTTTTCTT GCAAGTCTGA GATGTTGCCT        12200

TCTTTTCGAT AGACTGCAAA TTCAGAACTC TGTAATACAG CTTCTGAACG        12250

AGTAATCCAA CTGTGAAGTT CAGTTATATC GACATCCAAC CTTTTCCTGA        12300

GTTCAGAATC CACAGTTATC TGCCTCTTCT TTTGAGGAGG TGGTGGTGGA        12350

AGTTCCTCTT GGGCATGTTT TACCATGATT TGTTCCCTTG TGGTCACCAT        12400

AGTTACCGTT TCCATTACAG TTGTCTGTGT TAGGGATGGT TGAGTGGTGG        12450

TGACAGCCTG TGAAATTTGT GCTGAACTCT TTTCAAGTTT TTGGGTTAAA        12500

TTGTCCCAAC GTTGTGCAAA GTTTTCCATC CAGATTTCCA TCTTTTGAGT        12550

CACTGACTTA TTTTTCAGTG CCGAAAGTAG ATCTTGATTG AGTGAACTTA        12600

GTTTTTCCAT GGTTGGCTTT TTCTTTTCTA GATCTATTTT TAAAGTAGAT        12650

ATTTGTGAA GACTTGACAT CATTTCATTT TGATCTTTAA AGCCACTTGT         12700

CTGAATGTTC TTCATTGCAT CTTCTTTTTC TGAAAGCCAT GTACTAAAAA        12750

GGCACTGTTC TTCAGTAAAA TGCTGCCATT TTAGAAGAAT ATCTTGTAAA        12800

ACAATCCAGC GGTCTTCAGT CCATCTGCAG ATATTTGCCC ATCGATCTCC        12850

CAGTACCTTA AGTTGTTCTT CCAAAGCAGC TGTTGCATGA TCACCGCTGG       12900

ATTCATCAAC CACTACTACC ATGTGAGTGA GCGAGTTGAC CCTGACCTGC        12950

TCCTGTTCTA GATCTTCTTG AAGCACCTTA TGTTGTTGTA CTTGGCATTT        13000

TAGATCTTCA AGATCAGGTC CAAAGGGCTC TTCCTCCATT TTCTTAGTTC        13050

TCTCTTCAGT TTTTGTTAAC CAGTCATCTA GTTCTTTTAA TTTCTGATTC        13100

TGGAGATCCA TTAGAACTTT GTGTAATTTG CTTTGTTTTT CCATGCTAGC        13150

TACCCTGAGA CATTCCCATC TTGAATTTAG GAGATTCATT TGTTCTTGCA        13200

CTTCAGCTTC TTCATCTTCT GATAATTTCC CTTTTCCAAC TAGTTGACTT        13250

CCTAACTGTA GAACATTACC AACAAGTCCT TGATGAGATG TCAGATCCAT        13300

CATGAATCCC TCATGAGCAT GAAACTGTTC TTTCACTTCT TCAACATCAT        13350

TTGAAATCTC TCCTTGTGCT CGCAATGTAT CCTCGGCAGA AAGAAGCCAT        13400

GAAAGTACTT CTTCTAAAGC AGTTTGGTAA CTATCCAGAT TTACTTCCGT        13450

CTCCATCAAT GAACTGTCAA GTGACTTGTC TCTGGGAGCT TCCAAATGCT        13500

GTGAAGGATA GGGGCTCTGT GTGGAATCAG AGGTGGCAAC ATAAGCAGCC        13550

TGTGTGAAGG CATAACTCTT GAATCGAGGC TTAGGAGATG AAGAAGTTTG        13600

TTCATAGCCC TGTGCTAGAC TGACTGTGAT CTGTTGAGAG TAATGCATCT        13650

GGTGATGTAA TTGAAAATGT TCTTCTCTAG TTACTTTTGA AGATGTCCTG        13700

GGCAACATTT CCACTTCTTG AATGGCTTCA ATGCTCACTT GTTGTGGCAA        13750

AACTTGAAAG AGTGATGTGA TGTACATTAA GATGGACTTC TTGTCTGGAT        13800

AAGTGGTAGC AACATCTTCA GGATCAAGAA GTTTTTCTAT GCCTAACTGG        13850

CATTTTGCAA TGTTGAAGGC ATGTTCCAGT CTTTGGGTGG CTGAGTGCTG        13900

TGAAACCACA CTATTCCAAT CAAACAGGTC GGGCCTGTGA CTATGGATAA        13950

GAGCATTCAA AGCCAACCCG TCGGACCAGC TAGAGGTGAA GTTGATGACG        14000

TTAACCTGTG GATAATTACG TGTTGACTGT CGAACCCAGC TCAGAAGAAT        14050
```

```
CTTTTCACTG TTGGTTTGCT GCAATCCAGC CATGATAGTT TTCATCACAT         14100

TTTTGACCTG CCAGTGGAGG ATTATATTCC AAATCAAACC AAGAGTGAGT         14150

TTATGATTTC CATCCACTAT GTCAGTGCTT CCTATATTCA CTAAATCAAC         14200

ATTATTTTTC TGTAAGACCC GCAGTGCCTT GTTGACATTG TTCAGGGCAT         14250

GAACTCTTGT AGATCCCTTT TCTTTTGGCA GTTTTTGCCC TGTAAGGCCT         14300

TCCAAGAGGT CTAGGAGGCG TTTTCCATCC TGCAGGTCAC TGAAGAGGTT         14350

GTCTATGTGT TGCTTTCCAA ACTTAGAAAA TTGTGCATTT ATCCATTTTG         14400

TGAATGTTTT CTTTTGAACA TCTTCTCTTT CATAACAGTC CTCTACTTCT         14450

TCCCACCAAA GCATTTGGAA GAAAAAGTAT ATATCAAGGC AGGGATAAAA         14500

ATCTTGGTAA AAGTTTCTCC CAGTTTTATT GCTCCAGGAG GCTTAGGTAC         14550

GATGAGAAGC CAATAAACTT CAGCAGCCTT GACAAAAAAA AAAAAAAAAA         14600

TAGCACTTCA AGTCTTCCTA TTCGTTTTTT CTATAAAGCT ATTGCCTTCA         14650

AGAGCGGAAT TCCTGCAGCC CGGGGGATCC ACTAGTTCTA GAGCGGCCGC         14700

GGGTACAATT CCGCAGCTTT TAGAGCAGAA GTAACACTTC CGTACAGGCC         14750

TAGAAGTAAA GGCAACATCC ACTGAGGAGC AGTTCTTTGA TTTGCACCAC         14800

CACCGGATCC GGGACCTGAA ATAAAAGACA AAAGACTAA ACTTACCAGT          14850

TAACTTTCTG GTTTTTCAGT TCCTCGAGTA CCGGATCCTC TAGAGTCCGG         14900

AGGCTGGATC GGTCCCGGTG TCTTCTATGG AGGTCAAAAC AGCGTGGATG         14950

GCGTCTCCAG GCGATCTGAC GGTTCACTAA ACGAGCTCTG CTTATATAGA         15000

CCTCCCACCG TACACGCCTA CCGCCCATTT GCGTCAATGG GGCGGAGTTG         15050

TTACGACATT TTGGAAAGTC CCGTTGATTT TGGTGCCAAA ACAAACTCCC         15100

ATTGACGTCA ATGGGGTGGA GACTTGGAAA TCCCCGTGAG TCAAACCGCT         15150

ATCCACGCCC ATTGATGTAC TGCCAAAACC GCATCACCAT GGTAATAGCG         15200

ATGACTAATA CGTAGATGTA CTGCCAAGTA GGAAAGTCCC ATAAGGTCAT         15250

GTACTGGGCA TAATGCCAGG CGGGCCATTT ACCGTCATTG ACGTCAATAG         15300

GGGGCGTACT TGGCATATGA TACACTTGAT GTACTGCCAA GTGGGCAGTT         15350

TACCGTAAAT ACTCCACCCA TTGACGTCAA TGGAAAGTCC CTATTGGCGT         15400

TACTATGGGA ACATACGTCA TTATTGACGT CAATGGGCGG GGGTCGTTGG         15450

GCGGTCAGCC AGGCGGGCCA TTTACCGTAA GTTATGTAAC GACCTGCAGG         15500

TCGACTCTAG AGGATCTCCC TAGACAAATA TTACGCGCTA TGAGTAACAC         15550

AAAATTATTC AGATTTCACT TCCTCTTATT CAGTTTTCCC GCGAAAATGG         15600

CCAAATCTTA CTCGGTTACG CCCAAATTTA CTACAACATC CGCCTAAAAC         15650

CGCGCGAAAA TTGTCACTTC CTGTGTACAC CGGCGCACAC CAAAAACGTC         15700

ACTTTTGCCA CATCCGTCGC TTACATGTGT TCCGCCACAC TTGCAACATC         15750

ACACTTCCGC CACACTACTA CGTCACCCGC CCCGTTCCCA CGCCCCGCGC         15800

CACGTCACAA ACTCCACCCC CTCATTATCA TATTGGCTTC AATCCAAAAT         15850

AAGGTATATT ATTGATGATG CTAGCGGGGC CCTATATATG GATCCAATTG         15900

CAATGATCAT CATGACAGAT CTGCGCGCGA TCGATATCAG CGCTTTAAAT         15950

TTGCGCATGC TAGCTATAGT TCTAGAGGTA CCGGTTGTTA ACGTTAGCCG         16000

GCTACGTATA CTCCGGAATA TTAATAGGCC TAGGATGCAT ATGGCGGCCG         16050
```

```
GCCGCCTGCA GCTGGCGCCA TCGATACGCG TACGTCGCGA CCGCGGACAT        16100

GTACAGAGCT CGAGAAGTAC TAGTGGCCAC GTGGGCCGTG CACCTTAAGC        16150

TTGGCACTGG CCGTCGTTTT ACAACGTCGT GACTGGGAAA ACCCTGGCGT        16200

TACCCAACTT AATCGCCTTG CAGCACATCC CCCTTTCGCC AGCTGGCGTA        16250

ATAGCGAAGA GGCCCGCACC GATCGCCCTT CCCAACAGTT GCGCAGCCTG        16300

AATGGCGAAT GGCGCCTGAT GCGGTATTTT CTCCTTACGC ATCTGTGCGG        16350

TATTTCACAC CGCATACGTC AAAGCAACCA TAGTACGCGC CCTGTAGCGG        16400

CGCATTAAGC GCGGCGGGTG TGGTGGTTAC GCGCAGCGTG ACCGCTACAC        16450

TTGCCAGCGC CCTAGCGCCC GCTCCTTTCG CTTTCTTCCC TTCCTTTCTC        16500

GCCACGTTCG CCGGCTTTCC CCGTCAAGCT CTAAATCGGG GGCTCCCTTT        16550

AGGGTTCCGA TTTAGTGCTT TACGGCACCT CGACCCCAAA AAACTTGATT        16600

TGGGTGATGG TTCACGTAGT GGGCCATCGC CCTGATAGAC GGTTTTTCGC        16650

CCTTTGACGT TGGAGTCCAC GTTCTTTAAT AGTGGACTCT TGTTCCAAAC        16700

TGGAACAACA CTCAACCCTA TCTCGGGCTA TTCTTTTGAT TTATAAGGGA        16750

TTTTGCCGAT TTCGGCCTAT TGGTTAAAAA ATGAGCTGAT TTAACAAAAA        16800

TTTAACGCGA ATTTTAACAA AATATTAACG TTTACAATTT TATGGTGCAC        16850

TCTCAGTACA ATCTGCTCTG ATGCCGCATA GTTAAGCCAG CCCCGACACC        16900

CGCCAACACC CGCTGACGCG CCCTGACGGG CTTGTCTGCT CCCGGCATCC        16950

GCTTACAGAC AAGCTGTGAC CGTCTCCGGG AGCTGCATGT GTCAGAGGTT        17000

TTCACCGTCA TCACCGAAAC GCGCGAGACG AAAGGGCCTC GTGATACGCC        17050

TATTTTTATA GGTTAATGTC ATGATAATAA TGGTTTCTTA GACGTCAGGT        17100

GGCACTTTTC GGGGAAATGT GCGCGGAACC CCTATTTGTT TATTTTTCTA        17150

AATACATTCA AATATGTATC CGCTCATGAG ACAATAACCC TGATAAATGC        17200

TTCAATAATA TTGAAAAAGG AAGAGTATGA GTATTCAACA TTTCCGTGTC        17250

GCCCTTATTC CCTTTTTTGC GGCATTTTGC CTTCCTGTTT TTGCTCACCC        17300

AGAAACGCTG GTGAAAGTAA AAGATGCTGA AGATCAGTTG GGTGCACGAG        17350

TGGGTTACAT CGAACTGGAT CTCAACAGCG GTAAGATCCT TGAGAGTTTT        17400

CGCCCCGAAG AACGTTTTCC AATGATGAGC ACTTTTAAAG TTCTGCTATG        17450

TGGCGCGGTA TTATCCCGTA TTGACGCCGG GCAAGAGCAA CTCGGTCGCC        17500

GCATACACTA TTCTCAGAAT GACTTGGTTG AGTACTCACC AGTCACAGAA        17550

AAGCATCTTA CGGATGGCAT GACAGTAAGA GAATTATGCA GTGCTGCCAT        17600

AACCATGAGT GATAACACTG CGGCCAACTT ACTTCTGACA ACGATCGGAG        17650

GACCGAAGGA GCTAACCGCT TTTTTGCACA ACATGGGGGA TCATGTAACT        17700

CGCCTTGATC GTTGGGAACC GGAGCTGAAT GAAGCCATAC CAAACGACGA        17750

GCGTGACACC ACGATGCCTG TAGCAATGGC AACAACGTTG CGCAAACTAT        17800

TAACTGGCGA ACTACTTACT CTAGCTTCCC GGCAACAATT AATAGACTGG        17850

ATGGAGGCGG ATAAAGTTGC AGGACCACTT CTGCGCTCGG CCCTTCCGGC        17900

TGGCTGGTTT ATTGCTGATA AATCTGGAGC CGGTGAGCGT GGGTCTCGCG        17950

GTATCATTGC AGCACTGGGG CCAGATGGTA AGCCCTCCCG TATCGTAGTT        18000

ATCTACACGA CGGGGAGTCA GGCAACTATG GATGAACGAA ATAGACAGAT        18050
```

-continued

```
CGCTGAGATA GGTGCCTCAC TGATTAAGCA TTGGTAACTG TCAGACCAAG            18100

TTTACTCATA TATACTTTAG ATTGATTTAA AACTTCATTT TTAATTTAAA            18150

AGGATCTAGG TGAAGATCCT TTTTGATAAT CTCATGACCA AAATCCCTTA            18200

ACGTGAGTTT TCGTTCCACT GAGCGTCAGA CCCCGTAGAA AAGATCAAAG            18250

GATCTTCTTG AGATCCTTTT TTTCTGCGCG TAATCTGCTG CTTGCAAACA            18300

AAAAAACCAC CGCTACCAGC GGTGGTTTGT TTGCCGGATC AAGAGCTACC            18350

AACTCTTTTT CCGAAGGTAA CTGGCTTCAG CAGAGCGCAG ATACCAAATA            18400

CTGTTCTTCT AGTGTAGCCG TAGTTAGGCC ACCACTTCAA GAACTCTGTA            18450

GCACCGCCTA CATACCTCGC TCTGCTAATC CTGTTACCAG TGGCTGCTGC            18500

CAGTGGCGAT AAGTCGTGTC TTACCGGGTT GGACTCAAGA CGATAGTTAC            18550

CGGATAAGGC GCAGCGGTCG GGCTGAACGG GGGGTTCGTG CACACAGCCC            18600

AGCTTGGAGC GAACGACCTA CACCGAACTG AGATACCTAC AGCGTGAGCT            18650

ATGAGAAAGC GCCACGCTTC CCGAAGGGAG AAAGGCGGAC AGGTATCCGG            18700

TAAGCGGCAG GGTCGGAACA GGAGAGCGCA CGAGGGAGCT TCCAGGGGGA            18750

AACGCCTGGT ATCTTTATAG TCCTGTCGGG TTTCGCCACC TCTGACTTGA            18800

GCGTCGATTT TTGTGATGCT CGTCAGGGGG GCGGAGCCTA TGGAAAAACG            18850

CCAGCAACGC GGCCTTTTTA CGGTTCCTGG CCTTTTGCTG GCCTTTTGCT            18900

CACATGTTCT TTCCTGCGTT ATCCCCTGAT TCTGTGGATA ACCGTATTAC            18950

CGCCTTTGAG TGAGCTGATA CCGCTCGCCG CAGCCGAACG ACCGAGCGCA            19000

GCGAGTCAGT GAGCGAGGAA GCGGAAGAGC GCCCAATACG CAAACCGCCT            19050

CTCCCCGCGC GTTGGCCGAT TCATTAATGC AGCTGGCACG ACAGGTTTCC            19100

CGACTGGAAA GCGGGCAGTG AGCGCAACGC AATTAATGTG AGTTAGCTCA            19150

CTCATTAGGC ACCCCAGGCT TTACACTTTA TGCTTCCGGC TCGTATGTTG            19200

TGTGGAATTG TGAGCGGATA ACAATTTCAC ACAGGAAACA GCTATGACCA            19250

TGATTACGAA TTCGAATGGC CATGGGACGT CGACCTGAGG TAATTATAAC            19300

CCGGGCC                                                          19307
```